(12) United States Patent
Deutsch et al.

(10) Patent No.: US 9,975,118 B2
(45) Date of Patent: May 22, 2018

(54) DEVICE FOR THE STUDY OF LIVING CELLS

(75) Inventors: Mordechai Deutsch, Moshav Olesh-Doar-Na Lev HaSharon (IL); Assaf Deutsch, Tzfaria (IL)

(73) Assignee: Seng Enterprises Ltd., Larnaca (CY)

( * ) Notice: Subject to any disclaimer, the term of this patent is extended or adjusted under 35 U.S.C. 154(b) by 210 days.

(21) Appl. No.: 12/810,868

(22) PCT Filed: Dec. 25, 2008

(86) PCT No.: PCT/IL2008/001678
§ 371 (c)(1),
(2), (4) Date: Oct. 12, 2010

(87) PCT Pub. No.: WO2009/081409
PCT Pub. Date: Jul. 2, 2009

(65) Prior Publication Data
US 2011/0034348 A1    Feb. 10, 2011

Related U.S. Application Data

(63) Continuation-in-part of application No. PCT/IL2008/001492, filed on Nov. 13, 2008, which
(Continued)

(51) Int. Cl.
*B01L 3/00*    (2006.01)
*C12M 1/32*    (2006.01)
*C12M 1/00*    (2006.01)

(52) U.S. Cl.
CPC ........... *B01L 3/5027* (2013.01); *C12M 23/12* (2013.01); *C12M 23/22* (2013.01); *B01L 3/5085* (2013.01);
(Continued)

(58) Field of Classification Search
CPC ................ B01L 3/5027; B01L 3/5085; B01L 2300/041; B01L 2300/0887;
(Continued)

(56) References Cited

U.S. PATENT DOCUMENTS 3,558,387 A    1/1971    Bassemir et al.
4,072,578 A    2/1978    Cady et al.
(Continued)

FOREIGN PATENT DOCUMENTS

DE    4132379    4/1993
EP    0059297    9/1982
(Continued)

OTHER PUBLICATIONS

Restriction Official Action dated Dec. 9, 2011 From the US Patent and Trademark Office Re. U.S. Appl. No. 12/742,730.
(Continued)

*Primary Examiner* — Lore R Jarrett

(57) ABSTRACT

A cell study device, comprising, a base layer, a planar conduit defining layer, including a conduit cut out of the layer; and a planar cover layer which defines a capillary flow channel in said conduit layer, said conduit layer and said cover layer acting as side walls for said capillary flow channel, wherein said layers are formed of materials that do not interfere with cell behavior over a period of at least 5 hours when loaded with aqueous solution.

61 Claims, 28 Drawing Sheets

Related U.S. Application Data is a continuation-in-part of application No. 11/940,996, filed on Nov. 15, 2007, now Pat. No. 7,888,110, application No. 12/810,868, which is a continuation-in-part of application No. 12/712,232, filed on Feb. 25, 2010, now Pat. No. 9,145,540, and a continuation-in-part of application No. PCT/IL2008/001678, filed on Dec. 25, 2008.

(60) Provisional application No. 61/006,130, filed on Dec. 26, 2007, provisional application No. 61/155,186, filed on Feb. 25, 2009.

(52) U.S. Cl.
CPC ... *B01L 3/502715* (2013.01); *B01L 2200/027* (2013.01); *B01L 2200/0668* (2013.01); *B01L 2300/041* (2013.01); *B01L 2300/0809* (2013.01); *B01L 2300/0822* (2013.01); *B01L 2300/0887* (2013.01); *B01L 2300/0893* (2013.01); *B01L 2300/123* (2013.01); *B01L 2400/0406* (2013.01); *Y10T 29/49826* (2015.01)

(58) Field of Classification Search
CPC ....... B01L 2300/123; B01L 2300/0809; B01L 2300/0893; B01L 2200/0668; B01L 2200/027; B01L 3/502715; B01L 2400/0406; B01L 2300/0822; C12M 23/22; C12M 23/12; Y10T 29/49826
See application file for complete search history.

(56) References Cited

U.S. PATENT DOCUMENTS

| | | | |
|---|---|---|---|
| 4,207,554 A | 6/1980 | Resnick et al. | |
| 4,308,351 A | 12/1981 | Leighton et al. | |
| 4,684,538 A | 8/1987 | Klemarczyk | |
| 4,716,101 A | 12/1987 | Thompson | |
| 4,729,949 A | 3/1988 | Weinreb et al. | |
| 4,756,884 A * | 7/1988 | Hillman et al. | 422/73 |
| 4,839,280 A | 6/1989 | Banes | |
| 4,894,343 A | 1/1990 | Tanaka et al. | |
| 4,895,805 A | 1/1990 | Sato et al. | |
| 5,043,082 A | 8/1991 | Hermann, Jr. et al. | |
| 5,059,266 A | 10/1991 | Yamane et al. | |
| 5,153,136 A | 10/1992 | Vandenburgh | |
| 5,204,055 A | 4/1993 | Sachs et al. | |
| 5,272,081 A | 12/1993 | Weinreb | |
| 5,324,591 A | 6/1994 | Georger et al. | |
| 5,395,588 A | 3/1995 | North, Jr. et al. | |
| 5,428,451 A | 6/1995 | Lea et al. | |
| 5,506,141 A | 4/1996 | Weinreb et al. | |
| 5,525,800 A | 6/1996 | Sanghera et al. | |
| 5,612,184 A | 3/1997 | Rosson | |
| 5,627,045 A | 5/1997 | Bochner et al. | |
| 5,650,323 A | 7/1997 | Root et al. | |
| 5,707,869 A | 1/1998 | Wolf et al. | |
| 5,744,366 A | 4/1998 | Kricka et al. | |
| 5,854,684 A | 12/1998 | Stabile et al. | |
| 5,905,031 A | 5/1999 | Kuylen et al. | |
| 5,910,287 A | 6/1999 | Cassin et al. | |
| 6,025,129 A | 2/2000 | Nova et al. | |
| 6,027,695 A | 2/2000 | Oldenburg et al. | |
| 6,037,168 A * | 3/2000 | Brown | 435/288.3 |
| 6,046,426 A | 4/2000 | Jeantette et al. | |
| 6,048,723 A | 4/2000 | Banes | |
| 6,066,285 A | 5/2000 | Kumar | |
| 6,103,479 A | 8/2000 | Taylor | |
| 6,117,612 A | 9/2000 | Halloran et al. | |
| 6,206,672 B1 | 3/2001 | Grenda | |
| 6,228,437 B1 | 5/2001 | Schmidt | |
| 6,238,614 B1 | 5/2001 | Yang et al. | |
| 6,312,888 B1 * | 11/2001 | Wong | G01N 33/525 |
| | | | 435/283.1 |
| 6,315,940 B1 | 11/2001 | Nisch et al. | |
| 6,329,195 B1 | 12/2001 | Pfaller | |
| 6,333,192 B1 | 12/2001 | Petitte et al. | |
| 6,338,964 B1 | 1/2002 | Matanguihan et al. | |
| 6,342,384 B1 | 1/2002 | Chung et al. | |
| 6,344,354 B1 | 2/2002 | Webster et al. | |
| 6,345,115 B1 | 2/2002 | Ramm et al. | |
| 6,372,494 B1 | 4/2002 | Naughton et al. | |
| 6,376,148 B1 | 4/2002 | Liu et al. | |
| 6,377,721 B1 | 4/2002 | Walt et al. | |
| 6,378,527 B1 | 4/2002 | Hungerford et al. | |
| 6,383,810 B2 | 5/2002 | Fike et al. | |
| 6,403,369 B1 | 6/2002 | Wood | |
| 6,410,309 B1 | 6/2002 | Barbera-Guillem et al. | |
| 6,413,680 B1 | 7/2002 | Watanabe et al. | |
| 6,413,744 B1 | 7/2002 | Morris et al. | |
| 6,413,746 B1 | 7/2002 | Field | |
| 6,416,642 B1 | 7/2002 | Alajoki et al. | |
| 6,455,310 B1 | 9/2002 | Barbera-Guillem et al. | |
| 6,465,000 B1 | 10/2002 | Kim | |
| 6,465,205 B2 | 10/2002 | Hicks, Jr. | |
| 6,468,788 B1 | 10/2002 | Marotzki | |
| 6,479,252 B1 | 11/2002 | Barbera-Guillem et al. | |
| 6,485,690 B1 | 11/2002 | Pfost et al. | |
| 6,489,144 B1 | 12/2002 | Lau | |
| 6,492,148 B1 | 12/2002 | van Loon et al. | |
| 6,492,163 B1 | 12/2002 | Yoo et al. | |
| 6,495,340 B2 | 12/2002 | Huberman et al. | |
| 6,506,598 B1 | 1/2003 | Andersen et al. | |
| 6,511,430 B1 | 1/2003 | Sherar et al. | |
| 6,521,182 B1 * | 2/2003 | Shartle et al. | 422/417 |
| 6,528,286 B1 | 3/2003 | Ryll | |
| 6,544,788 B2 | 4/2003 | Singh | |
| 6,555,365 B2 | 4/2003 | Barbera-Guillem et al. | |
| 6,569,422 B1 | 5/2003 | van Loon et al. | |
| 6,588,586 B2 | 7/2003 | Abasolo et al. | |
| 6,589,765 B1 | 7/2003 | Choi et al. | |
| 6,593,101 B2 | 7/2003 | Richards-Kortum et al. | |
| 6,593,140 B1 | 7/2003 | Field | |
| 6,610,516 B1 | 8/2003 | Andersen et al. | |
| 6,613,513 B1 * | 9/2003 | Parce | B01L 3/5027 |
| | | | 435/6.11 |
| 6,627,426 B2 | 9/2003 | Biddle et al. | |
| 6,632,619 B1 | 10/2003 | Harrison et al. | |
| 6,635,448 B2 | 10/2003 | Bucciarelli et al. | |
| 6,642,050 B1 | 11/2003 | Goto et al. | |
| 6,645,757 B1 | 11/2003 | Okandan et al. | |
| 6,649,408 B2 | 11/2003 | Bailey et al. | |
| 6,653,124 B1 * | 11/2003 | Freeman | B01L 3/5027 |
| | | | 435/286.5 |
| 6,660,501 B2 | 12/2003 | Field | |
| 6,667,034 B2 | 12/2003 | Palsson et al. | |
| 6,670,180 B2 | 12/2003 | Block | |
| 6,670,184 B2 | 12/2003 | Chiarello et al. | |
| 6,673,591 B2 | 1/2004 | Lau | |
| 6,686,190 B2 | 2/2004 | Lau | |
| 6,689,594 B1 | 2/2004 | Hänni et al. | |
| 6,692,961 B1 | 2/2004 | Judd et al. | |
| 6,695,765 B1 | 2/2004 | Beebe et al. | |
| 6,699,665 B1 | 3/2004 | Kim et al. | |
| 6,706,519 B1 | 3/2004 | Kellogg et al. | |
| 7,118,910 B2 | 10/2006 | Unger et al. | |
| 7,139,415 B2 | 11/2006 | Finkbeiner | |
| 7,169,578 B2 | 1/2007 | Wang et al. | |
| 7,285,412 B2 | 10/2007 | Casagrande et al. | |
| 7,323,305 B2 | 1/2008 | Leamon et al. | |
| 7,354,733 B2 | 4/2008 | Bukshpan et al. | |
| 7,403,647 B2 | 7/2008 | Deutsch et al. | |
| 7,405,071 B2 | 7/2008 | Deutsch | |
| 7,888,110 B2 | 2/2011 | Deutsch et al. | |
| 8,003,377 B2 | 8/2011 | Deutsch et al. | |
| 9,200,245 B2 | 12/2015 | Deutsch et al. | |
| 2002/0001856 A1 | 1/2002 | Chow et al. | |
| 2002/0052003 A1 | 5/2002 | Alberte et al. | |
| 2002/0064885 A1 | 5/2002 | Bedingham et al. | |
| 2002/0106715 A1 | 8/2002 | Huberman et al. | |
| 2002/0127604 A1 | 9/2002 | Allbritton et al. | |

(56) References Cited

U.S. PATENT DOCUMENTS

| | | |
|---|---|---|
| 2002/0150909 A1 | 10/2002 | Stuelpnagel et al. |
| 2002/0173033 A1* | 11/2002 | Hammerick ......... C12N 5/0062 435/305.2 |
| 2002/0182627 A1 | 12/2002 | Wang et al. |
| 2002/0187074 A1 | 12/2002 | O'Connor et al. |
| 2002/0189374 A1 | 12/2002 | DeSilets et al. |
| 2003/0017079 A1 | 1/2003 | Hahn et al. |
| 2003/0030184 A1 | 2/2003 | Kim et al. |
| 2003/0032048 A1 | 2/2003 | Kim et al. |
| 2003/0032204 A1 | 2/2003 | Walt et al. |
| 2003/0036188 A1 | 2/2003 | Kim et al. |
| 2003/0059764 A1 | 3/2003 | Ravkin et al. |
| 2003/0082632 A1 | 5/2003 | Shumate |
| 2003/0082818 A1 | 5/2003 | Bahnson et al. |
| 2003/0087292 A1* | 5/2003 | Chen et al. ................. 435/6 |
| 2003/0104494 A1* | 6/2003 | Ravkin et al. ............. 435/7.9 |
| 2003/0113833 A1 | 6/2003 | Oka et al. |
| 2003/0124716 A1 | 7/2003 | Hess et al. |
| 2003/0162284 A1 | 8/2003 | Dordick et al. |
| 2003/0189850 A1 | 10/2003 | Sasaki et al. |
| 2003/0211458 A1 | 11/2003 | Sunray et al. |
| 2004/0053354 A1 | 3/2004 | Ikawa et al. |
| 2004/0091397 A1 | 5/2004 | Picard |
| 2004/0118757 A1 | 6/2004 | Terstappen et al. |
| 2004/0216835 A1 | 11/2004 | Tanner et al. |
| 2004/0235143 A1 | 11/2004 | Sasaki et al. |
| 2004/0241783 A1 | 12/2004 | Papkovsky et al. |
| 2004/0262210 A1 | 12/2004 | Westervelt et al. |
| 2005/0014201 A1 | 1/2005 | Deutsch |
| 2005/0026299 A1 | 2/2005 | Bhattacharjee et al. |
| 2005/0064524 A1 | 3/2005 | Deutsch et al. |
| 2005/0074869 A1 | 4/2005 | Yoshida et al. |
| 2005/0089993 A1 | 4/2005 | Boccazzi et al. |
| 2005/0105077 A1 | 5/2005 | Padmanabhan et al. |
| 2005/0106714 A1 | 5/2005 | Zarur et al. |
| 2005/0158845 A1 | 7/2005 | Wikswo et al. |
| 2005/0170498 A1 | 8/2005 | Dolley et al. |
| 2005/0230272 A1 | 10/2005 | Lee et al. |
| 2005/0277125 A1 | 12/2005 | Benn et al. |
| 2006/0041384 A1 | 2/2006 | Kermani et al. |
| 2006/0057557 A1 | 3/2006 | Deutsch et al. |
| 2006/0154233 A1 | 7/2006 | Deutsch |
| 2006/0173394 A1* | 8/2006 | Stroock ............... A61F 2/30756 602/41 |
| 2006/0240548 A1 | 10/2006 | Deutsch et al. |
| 2007/0105089 A1 | 5/2007 | Deutsch |
| 2007/0141555 A1 | 6/2007 | Deutsch |
| 2007/0154357 A1 | 7/2007 | Szlosek |
| 2007/0178607 A1 | 8/2007 | Prober et al. |
| 2007/0292312 A1 | 12/2007 | Bachman et al. |
| 2007/0292457 A1 | 12/2007 | Deutsch et al. |
| 2008/0003142 A1 | 1/2008 | Link et al. |
| 2008/0009051 A1 | 1/2008 | Deutsch et al. |
| 2008/0063251 A1 | 3/2008 | Deutsch |
| 2008/0063572 A1 | 3/2008 | Deutsch et al. |
| 2008/0241874 A1 | 10/2008 | Deutsch |
| 2009/0105095 A1 | 4/2009 | Deutsch |
| 2009/0111141 A1 | 4/2009 | Deutsch |
| 2011/0014688 A1 | 1/2011 | Deutsch et al. |
| 2011/0018972 A1 | 1/2011 | Pan |
| 2013/0071914 A1 | 3/2013 | Deutsch |

FOREIGN PATENT DOCUMENTS

| | | |
|---|---|---|
| EP | 0094193 | 11/1983 |
| EP | 0602416 | 6/1994 |
| EP | 1262764 | 12/2002 |
| EP | 1566635 | 8/2005 |
| EP | 1691196 | 8/2006 |
| FR | 2890975 | 3/2007 |
| JP | 62-171687 | 7/1987 |
| JP | 06-221988 | 8/1994 |
| JP | 06-237753 | 8/1994 |
| JP | 10-276763 | 10/1998 |
| JP | 11-507724 | 7/1999 |
| JP | 2005-102628 | 4/2005 |
| WO | WO 96/31548 | 10/1996 |
| WO | WO 96/41153 | 12/1996 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 99/66329 | 12/1999 |
| WO | WO 00/20554 | 4/2000 |
| WO | WO 01/02539 | 1/2001 |
| WO | WO 01/35071 | 5/2001 |
| WO | WO 01/49824 | 7/2001 |
| WO | WO 01/88176 | 11/2001 |
| WO | WO 01/88185 | 11/2001 |
| WO | WO 02/08748 | 1/2002 |
| WO | WO 02/26114 | 4/2002 |
| WO | WO 02/48676 | 6/2002 |
| WO | WO 02/055653 | 7/2002 |
| WO | WO 02/058847 | 8/2002 |
| WO | WO 02/063034 | 8/2002 |
| WO | WO 02/064728 | 8/2002 |
| WO | WO 02/081662 | 10/2002 |
| WO | WO 02/097398 | 12/2002 |
| WO | WO 03/002750 | 1/2003 |
| WO | WO 03/011451 | 2/2003 |
| WO | WO 03/020871 | 3/2003 |
| WO | WO 03/035824 | 5/2003 |
| WO | WO 03/046508 | 6/2003 |
| WO | WO 03/052375 | 6/2003 |
| WO | WO 03/056330 | 7/2003 |
| WO | WO 03/056345 | 7/2003 |
| WO | WO 2004/077009 | 9/2004 |
| WO | WO 2004/113492 | 12/2004 |
| WO | WO 2005/007796 | 1/2005 |
| WO | WO 2005/069001 | 7/2005 |
| WO | WO 2005/103691 | 11/2005 |
| WO | WO 06/003664 | 1/2006 |
| WO | WO 2006/003664 | 1/2006 |
| WO | WO 2006/021959 | 3/2006 |
| WO | WO 2006/043267 | 4/2006 |
| WO | WO 2006/080000 | 8/2006 |
| WO | WO 2007/052245 | 5/2007 |
| WO | WO 2007/074449 | 7/2007 |
| WO | WO 2009/063462 | 5/2009 |
| WO | WO 2009/081409 | 7/2009 |

OTHER PUBLICATIONS

Restriction Official Action dated Dec. 12, 2011 From the US Patent and Trademark Office Re. U.S. Appl. No. 13/184,631.
Translation of Office Action dated Sep. 20, 2012 From the Israel Patent Office Re. Application No. 138314.
Response dated Dec. 21, 2011 to Communication Pursuant to Article 94(3) EPC dated Aug. 29, 2011 From the European Patent Office Re. Application No. 04745001.0.
Official Action dated Dec. 19, 2011 From the US Patent and Trademark Office Re.: U.S. Appl. No. 10/492,531.
Official Action dated Dec. 23, 2011 From the US Patent and Trademark Office Re. U.S. Appl. No. 10/565,240.
Applicant-Initiated Interview Summary dated Dec. 19, 2012 From the US Patent and Trademark Office Re. U.S. Appl. No. 12/742,730.
Applicant-Initiated Interview Summary dated Dec. 20, 2012 From the US Patent and Trademark Office Re. U.S. Appl. No. 13/184,631.
Office Action dated Dec. 17, 2012 From the Israel Patent Office Re. Application No. 205769 and Its Translation Into English.
Official Action dated Nov. 1, 2010 From the US Patent and Trademark Office Re.: U.S. Appl. No. 11/883,028.
Official Action dated Dec. 9, 2010 From the US Patent and Trademark Office Re. U.S. Appl. No. 10/565,240.
Official Action dated Dec. 22, 2010 From the US Patent and Trademark Office Re.: U.S. Appl. No. 11/883,028.
Proceeding Further With the European Patent Application Pursuant to Rule 70(2) EPC dated Nov. 10, 2009 From the European Patent Office Re. Application No. 04745001.0.

(56) References Cited

OTHER PUBLICATIONS

Response dated Jan. 2, 2011 to Proceeding Further With the European Patent Application Pursuant to Rule 70(2) EPC of Nov. 10, 2009 From the European Patent Office Re. Application No. 04745001.0.
Response dated Nov. 8, 2010 to Official Action dated Sep. 10, 2010 From the US Patent and Trademark Office Re.: U.S. Appl. No. 11/646,317.
Response dated Nov. 15, 2010 to Official Action dated Sep. 14, 2010 From the US Patent and Trademark Office Re.: U.S. Appl. No. 11/631,737.
Response dated Nov. 15, 2010 to Official Action dated Nov. 1, 2010 From the US Patent and Trademark Office Re.: U.S. Appl. No. 11/883,028.
Response dated Dec. 16, 2010 to Official Action dated Aug. 17, 2010 From the US Patent and Trademark Office Re.: U.S. Appl. No. 10/561,839.
Response dated Dec. 20, 2010 to Official Action dated Sep. 23, 2010 From the US Patent and Trademark Office Re.: U.S. Appl. No. 10/492,531.
Response dated Nov. 30, 2010 to Communication Pursuant to Article 94(3) EPC dated Aug. 5, 2010 From the European Patent Office Re. Application No. 05757567.2.
Communication Pursuant to Rule 58 EPC or Rule 159 EPC dated Nov. 24, 2010 From the European Patent Office Re. Application No. 10183774.8.
Response dated Jan. 3, 2011 to Communication Pursuant to Rule 58 EPC dated Rule 159 EPC of Nov. 24, 2010 From the European Patent Office Re. Application No. 10183774.8.
Office Action dated Dec. 31, 2012 From the Israel Patent Office Re. Application No. 206588 and Its Translation Into English.
Interview Summary dated Jan. 23, 2012 From the US Patent and Trademark Office Re.: U.S. Appl. No. 12/084,462.
Restriction Official Action dated Jan. 19, 2012 From the US Patent and Trademark Office Re. U.S. Appl. No. 13/019,320.
Official Action dated Jan. 19, 2011 From the US Patent and Trademark Office Re.: U.S. Appl. No. 11/646,317.
Response dated Jan. 24, 2011 to Official Action dated Sep. 23, 2010 From the US Patent and Trademark Office Re.: U.S. Appl. No. 11/646,294.
Response dated Jan. 12, 2011 to Office Action dated Oct. 5, 2010 From the Israel Patent Office Re. Application No. 184818.
Official Action dated Feb. 1, 2011 From the US Patent and Trademark Office Re.: U.S. Appl. No. 11/631,737.
Office Action dated Feb. 2, 2012 From the Israel Patent Office Re.: Application No. 173170 and Its Translation Into English.
Interview Summary dated Feb. 11, 2011 From the US Patent and Trademark Office Re.: U.S. Appl. No. 11/883,028.
Response dated Jan. 20, 2011 to Official Action dated Oct. 27, 2010 From the US Patent and Trademark Office Re.: U.S. Appl. No. 12/890,668.
Official Action dated Mar. 1, 2012 From the US Patent and Trademark Office Re.: U.S. Appl. No. 12/084,462.
Official Action dated Mar. 6, 2012 From the US Patent and Trademark Office Re. U.S. Appl. No. 12/155,643.
Response dated Feb. 7, 2011 to Communication Pursuant to Article 94(3) EPC dated Aug. 6, 2010 From the European Patent Office Re.: Application No. 04714873.9.
Office Action dated Feb. 28, 2011 From the Israel Patent Office Re. Application No. 180568 and Its Translation Into English.
Official Action dated Mar. 9, 2011 From the US Patent and Trademark Office Re.: U.S. Appl. No. 11/660,783.
Response dated Mar. 22, 2011 to Official Action dated Dec. 22, 2010 From the US Patent and Trademark Office Re.: U.S. Appl. No. 11/883,028.
European Search Report and the European Search Opinion dated Mar. 13, 2012 From the European Patent Office Re. Application No. 11170000.1.
Official Action dated Mar. 16, 2011 From the US Patent and Trademark Office Re. U.S. Appl. No. 10/561,839.
Response dated Feb. 17, 2011 to Communication Pursuant to Article 94(3) EPC of Aug. 9, 2010 From the European Patent Office Re. Application No. 01982673.4.
Cornell University "All About Birds: Optical Quality", Cornell University, 2 P., Oct. 3, 2010.
Response dated Feb. 23, 2011 to Official Action dated Jan. 19, 2011 From the US Patent and Trademark Office Re.: U.S. Appl. No. 11/646,317.
Invitation Pursuant to Article 94(3) and Rule 71(1) EPC dated Apr. 8, 2011 From the European Patent Office Re. Application No. 01982673.4.
Notice of Allowance dated Mar. 31, 2011 From the US Patent and Trademark Office Re.: U.S. Appl. No. 12/890,668.
Official Action dated Mar. 31, 2011 From the US Patent and Trademark Office Re.: U.S. Appl. No. 10/492,531.
Communication Pursuant to Rules 70(2) and 70a(2) EPC and Reference to Rule 39(1) EPC dated Apr. 16, 2012 From the European Patent Office Re. Application No. 11170000.1.
Communication Pursuant to Article 94(3) EPC dated Apr. 11, 2012 From the European Patent Office Re. Application No. 10183774.8.
Invitation Pursuant to Rule 63(1) EPC dated May 3, 2011 From the European Patent Office Re. Application No. 10183774.8.
Official Action dated Apr. 15, 2011 From the US Patent and Trademark Office Re.: U.S. Appl. No. 12/084,462.
Official Action dated Apr. 22, 2011 From the US Patent and Trademark Office Re.: U.S. Appl. No. 11/646,294.
Communication Pursuant to Article 94(3) EPC dated May 22, 2012 From the European Patent Office Re.: Application No. 04714873.9.
Notification of European Publication Number and Information on the Applicaiton of Article 67(3) EPC dated May 18, 2011 From the European Patent Office Re. Application No. 10183774.8.
Official Action dated May 23, 2011 From the US Patent and Trademark Office Re.: U.S. Appl. No. 11/646,317.
Response dated May 31, 2011 to Invitation Pursuant to Article 94(3) and Rule 71(1) EPC of Apr. 8, 2011 From the European Patent Office Re. Application No. 01982673.4.
Notice of Allowance dated Jun. 9, 2011 From the US Patent and Trademark Office Re.: U.S. Appl. No. 11/883,028.
Official Action dated Feb. 5, 2007 From the US Patent and Trademark Office Re.: U.S. Appl. No. 10/916,380.
Official Action dated Feb. 19, 2008 From the US Patent and Trademark Office Re.: U.S. Appl. No. 10/492,531.
Official Action dated Sep. 20, 2007 From the US Patent and Trademark Office Re.: U.S. Appl. No. 10/492,531.
Official Action dated Jan. 25, 2007 From the US Patent and Trademark Office Re.: U.S. Appl. No. 10/492,531.
Communication Pursuant to Article 94(3) EPC dated Feb. 13, 2009 From the European Patent Office Re.: Application No. 05763452.9.
Communication Pursuant to Article 94(3) EPC Dated Jun. 16, 2009 From the European Patent Office Re.: Application No. 04714873.9.
Communication Pursuant to Article 94(3) EPC dated Feb. 29, 2008 From the European Patent Office Re.: 05763452.9.
International Preliminary Report on Patentability dated Feb. 2, 2006 From the International Bureau of WIPO Re.: Application No. PCT/IL2004/000661.
International Preliminary Report on Patentability dated May 3, 2007 From the International Bureau of WIPO Re.: Application No. PCT/IL2005/001078.
International Preliminary Report on Patentability dated Mar. 8, 2007 From the International Bureau of WIPO Re.: Application No. PCT/IL2005/000914.
International Preliminary Report on Patentability dated Aug. 9, 2007 From the International Bureau of WIPO Re.: Application No. PCT/IL2005/000801.
International Preliminary Report on Patentability dated Jul. 10, 2008 From the International Bureau of WIPO Re.: Application No. PCT/IL2006/001487.
International Preliminary Report on Patentability dated Jan. 18, 2007 From the International Bureau of WIPO Re.: Application No. PCT/IL2005/000719.
International Preliminary Report on Patentability dated May 27, 2010 From the International Bureau of WIPO Re.: Application No. PCT/IL2008/001492.

(56) References Cited

OTHER PUBLICATIONS

International Preliminary Report on Patentability dated May 27, 2010 From the International Preliminary Examining Authority Re.: Application No. PCT/IL2008/001678.
International Preliminary Report on Patentability dated Nov. 28, 2007 From the International Bureau of WIPO Re.: Application No. PCT/IL2006/000483.
International Search Report dated Mar. 2, 2005 From the International Searching Authority Re.: Application No. PCT/IL04/00661.
International Search Report dated Feb. 7, 2006 From the International Searching Authority Re.: Application No. PCT/IL2005/001078.
International Search Report dated Nov. 7, 2005 From the International Searching Authority Re.: PCT/IL2005/000801.
International Search Report dated Nov. 9, 2004 From the International Searching Authority Re.: Application No. PCT/IL04/00571.
International Search Report Dated Sep. 10, 2009 From the International Searching Authority Re.: Application No. PCT/IL2008/001678.
International Search Report dated Sep. 11, 2006 From the International Seaching Authority Re.: Application No. PCT/IL2006/000483.
International Search Report dated May 13, 2009 From the International Searching Authority Re.: Application No. PCT/IL08/01492.
International Search Report dated Nov. 15, 2005 From the International Searching Authority Re.: PCT/IL2005/000719.
International Search Report dated Feb. 16, 2005 From the International Searching Authority Re.: PCT/IL04/00194.
International Search Report dated Jan. 17, 2003 From the International Searching Authority Re.: Application No. PCT/IL01/00992.
International Search Report dated Feb. 21, 2006 From the International Searching Authority Re.: Application No. PCT/IL2005/000914.
International Search Report dated Sep. 21, 2007 From the International Searching Authority Re.: PCT/IL2006/001487.
International Search Report dated Dec. 27, 2001 From the International Searching Authority Re.: Application No. PCT/IL01/00443.
Invitation to Pay Additional Fees dated Mar. 3, 2009 From the International Searching Authority Re.: Application No. PCT/IL08/01492.
Notice of Allowance dated Mar. 4, 2008 From the US Patent and Trademark Office Re.: U.S. Appl. No. 10/546,784.
Notice of Allowance dated Jan. 7, 2008 From the US Patent and Trademark Office Re.: U.S. Appl. No. 10/938,951.
Office Action dated Mar. 8, 2006 From the Israeli Patent Office Re.: Application No. 138314.
Office Action dated Apr. 12, 2007 From the Israeli Patent Office Re.: Application No. 138314.
Office Action dated Jul. 14, 2009 From the Israeli Patent Office Re.: Application No. 172724 and Its Translation Into English.
Office Action dated May 15, 2008 From the Israeli Patent Office Re.: U.S. Appl. No. 10/916,380.
Office Action dated Jul. 19, 2006 From the Israeli Patent Office Re.: Application No. 138314.
Office Action dated Mar. 22, 2009 From the Israeli Patent Office Re.: Application No. 170492 and Its Translation Into English.
Office Action dated Sep. 29, 2003 From the Israeli Patent Office Re.: Application No. 136232.
Official Action dated Mar. 5, 2010 From the US Patent and Trademark Office Re.: U.S. Appl. No. 10/561,839.
Official Action dated Jul. 13, 2009 From the US Patent and Trademark Office Re.: U.S. Appl. No. 11/660,783.
Official Action dated Dec. 14, 2007 From the US Patent and Trademark Office Re.: U.S. Appl. No. 10/916,380.
Official Action dated Nov. 14, 2008 From the US Patent and Trademark Office Re.: U.S. Appl. No. 10/492,531.
Official Action dated Oct. 16, 2006 From the US Patent and Trademark Office Re.: U.S. Appl. No. 10/492,531.
Official Action dated Dec. 18, 2006 From the US Patent and Trademark Office Re.: U.S. Appl. No. 10/276,080.
Official Action dated Oct. 22, 2007 From the US Patent and Trademark Office Re.: U.S. Appl. No. 11/492,531.
Official Action dated Feb. 23, 2010 From the US Patent and Trademark Office Re.: U.S. Appl. No. 12/084,462.
Official Action dated Mar. 23, 2005 From the US Patent and Trademark Office Re.: U.S. Appl. No. 10/276,080.
Official Action dated Aug. 25, 2006 From the US Patent and Trademark Office Re.: U.S. Appl. No. 10/276,080.
Official Action dated Jan. 25, 2007 From the US Patent and Trademark Office Re.: U.S. App. No. 10/492,531.
Official Action dated Aug. 28, 2007 From the US Patent and Trademark Office Re.: U.S. Appl. No. 10/916,380.
Official Action dated Jan. 28, 2010 From the US Patent and Trademark Office Re.: U.S. Appl. No. 10/492,531.
Official Action dated Jun. 29, 2009 From the US Patent and Trademark Office Re.: U.S. Appl. No. 10/492,531.
Response dated Dec. 14, 2009 to Office Action dated Jul. 14, 2009 From the Israel Patent Office Re.: Application No. 172724.
Response dated Jun. 15, 2010 to Notice of Reason for Rejection dated Mar. 30, 2010 From the Japanese Patent Office Re. Application No. 2006-502647.
Response dated May 25, 2010 to Official Action dated Jan. 28, 2010 From the US Patent and Trademark Office Re.: U.S. Appl. No. 10/492,531.
Response dated Apr. 29, 2005 to Communication Pursuant to Article 96(2) EPC of Dec. 23, 2004 From the European Patent Office Re.: Application No. 01934272.4.
Response dated Dec. 29, 2009 to Office Action dated Sep. 2, 2009 From the Israel Patent Office Re.: Application No. 200559.
Supplementary European Search Report dated Feb. 20, 2006 From the European Patent Office Re.: Application No. 04714873.9.
Supplementary European Search Report dated Oct. 22, 2009 From the European Patent Office Re.: Application No. 04744911.1.
Supplementary European Search Report dated Oct. 22, 2009 From the European Patent Office Re.: Application No. 04745001.0.
Supplementary European Search Report dated Oct. 26, 2004 From the European Patent Office Re.: Application No. EP 01934272.
Translation of Notice of Reason for Rejection dated Nov. 27, 2007 From Japanes Patent Office Re.: Application No. 2003-538325.
Translation of Notice of Reason for Rejection dated Mar. 30, 2010 From the Japanese Patent Office Re.: Application No. 2006-502647.
Written Opinion dated Sep. 10, 2009 From the International Searching Authority Re.: Application No. PCT/IL2008/001678.
Written Opinion dated May 13, 2009 From the International Searching Authority Re.: Application No. PCT/IL08/01492.
Written Opinion dated Nov. 15, 2005 From the International Searching Authority Re.: Application No. PCT/IL2005/000719.
Aplin et al. "Protein-Derivatised Glass Coverslips for the Study of Cell-to-Substratum Adhesion", Analytical Biochemistry, 113: 144-148, 1981.
Arikawa et al. "Microbial Biosensors Based on Respiratory Inhibition", Methos in Biotechnology, 6(Chap.16): 225-235, 1998.
Baruch et al. "Enzyme Activity—It's All About Image", Trends in Cell Biology, 14(1): 29-35, 2004.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4—col. 2, §1, p. 8, col. 2, §2.
Burlage et al. "Living Biosensors for the Management and Manipulation of Microbial Consortia", Annual Reviews in Microbiology, 48: 291-309, 1994.
Craighead et al. "Textured Surfaces: Optical Storage and Other Applications", Journal of Vacuum Science and Technology 20 (3): 316, 1982. Abstract.
Darzynkiewicz et al. "Laser-Scanning Cytometry: A New Instrumentation With Many Applications", Experimental Cell Research, 249(1): 1-12, 1999. Abstract, p. 2, col. 2, §4—p. 4, col. 2, §2, p. 8, col. 1, §1—col. 2, §2.
Deutsch et al. "Apparatus for High-Precision Repetitive Sequential Optical Measurement of Living Cells", Cytometry, 16: 214-226, 1994.

(56) References Cited

OTHER PUBLICATIONS

Deutsch et al. "Microplate Cell-Retaining Methodology for High-Content Analysis of Individual Non-Adherent Unanchored Cells in a Population", Biomedical Microdevices, 8: 361-374, 2006.
Dive et al. "Improved Methodology for Intracellular Enzyme Reaction and Inhibition Kinetics by Flow Cytometry", Cytometry Journal of Society for Analytical Cytology, 8(6): 552-561, 1987.
Dolbeare "Fluorescent Staining of Enzymes for Flow Cytometry", Methods in Cell Biology, 33(Chap.8): 81-88, 1990.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3Fls%3D3%26nr%3D133&h=299&w=429&.
Eisenthal et al. "Infection of K562 Cells With Influenza A Virus Increases Their Susceptibility to Natural Killer Lysis", Pathobiology, 65: 331-340, 1997.
Hansen et al. "Quantification of Bioavailable Chlortetracycline in Pig Feces Using a Bacterial Whole-Cell Biosensor", Veterinary Microbiology, 87: 51-57, 2002.
Kiguchi et al. "Induction of Urokinase-Type Plasminogen Activator by the Anthracycline Antibiotic in Human RC-K8 Lymphoma and H69 Lung-Carcinoma Cells", International Journal of Cancer, 93: 792-797, 2001.
Klingel et al. "Flow Cytometric Determination of Serine Proteinase Activities in Living Cells With Rhodamine 110 Substrates", Methods in Cell Biology, 41(Chap.29): 449-460, 1994.
Koh et al. "Poly(Ethylene Glycol) Hydrogel Microstructures Encapsulating Living Cells", Langmuir, 18(7): 2459-2462, 2002. p. 2459-2462, Fig.3.
Kovacic et al. "Mechanisms of Carcinogenesis: Focus on Oxidative Stress and Electron Transfer", Current Medicinal Chemistry, 8: 773-796, 2001.
Lansing Taylor et al. "Real-Time Molecular and Cellular Analysis: The New Frontier of Drug Discovery", Current Opinion in Biotechnology, 12: 75-81, 2001.
Malin-Berdel et al. "Flow Cytometric Determination of Esterase and Phosphatase Activities and Kinetics in Hematopoietic Cells With Fluorogenic Substrates", Cytometry, 1(3): 222-228, 1980.
Mrksich et al. "Using Self-Assembled Monolayers to Understand the Interactions of Man-Made Surfaces With Proteins and Cells", Annual Reviews in Biophysics and Biomolecular Structure, 25: 55-78, 1996.
Nooter et al. "On-Line Flow Cytometry. A Versatile Method for Kinetic Measurement", Methods in Cell Biology, 41(Chap.32): 509-526, 1994.
Riedel et al. "Arxula Adeninivorans Based Sensor for the Estimation of Bod", Analytical Letters, 31(1): 1-12, 1998.
Schroeder et al. "Coordination of Cell Growth in Cocultures by a Genetic Proliferation Control System", Biotechnology and Bioengineering, 78(3): 346-352, 2002.
Seahorse Bioscience "Designed for Scientists by Scienctists. How the XF24 Extracellular Flux Analyzer Works", Product Description, Seahorse Bioscience, 4 P., 2008.
Seahorse Bioscience "XF24 Extracellular Flux Analyzer", Product Description, Seahorse Bioscience, 3 P., 2008.
Simonian et al. "Microbial Biosensors Based on Potentiometric Detection", Methods in Biotechnology, 6(Chap.17): 237-248, 1998.
Singhvi et al. "Engineering Cell Shape and Function", Science, 264: 696-698, 1994.
Stevens et al. "Quorum Sensing in Vibrio Fischeri: Essential Elements for Activation of the Luminescence Genes", Journal of Bacteriology, 179(2): 557-562, Jan. 1997.
Suehiro et al. "The Dielectrophoretic Movement and Positioning of a Biological Cell Using a Three-Dimensional Grid Electrode System", J. Phys. D. Appl. Phys, vol. 31 p. 3298-3305, 1998.
Sunray et al. "Cell Activation Influences Cell Staining Kinetics", Spectrochimica Part A, 53: 1645-1653, 1997.
Sunray et al. "Determination of Individual Cell Michaelis-Menten Constants", Cytometry, 47(1): 8-16, 2002.
Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.
Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7—p. 714, col. 2, §1.
Tixier et al. Catching and Attaching Cells Using an Array of Microholes, 2nd Conference of the Society for Chemistry and Micro Systems, p. 60, 2000. Abstract.
Turek et al. "Leucine Aminopeptidase Activity by Flow Cytometry", Methods in Cell Biology, 41(Chap.30): 461-468, 1994.
Watson et al. "Enzyme Kinetics", Methods in Cell Biology, 41: 469-508, 1994.
Yamamura et al. "Single-Cell Microarray for Analyzing Cellular Response", Analytical Chemistry, 77(24): 8050-8056, 2005.
Communication Pursuant to Article 94(3) EPC dated Jun. 25, 2012 From the European Patent Office Re. Application No. 04745001.0.
Official Action dated Jun. 21, 2012 From the US Patent and Trademark Office Re.: U.S. Appl. No. 10/492,531.
Response dated Jun. 1, 2011 to Official Action dated Feb. 1, 2011 From the US Patent and Trademark Office Re.: U.S. Appl. No. 11/631,737.
Response dated Jun. 9, 2011 to Official Action dated Mar. 9, 2011 From the US Patent and Trademark Office Re.: U.S. Appl. No. 11/660,783.
Communication Pursuant to Article 94(3) EPC dated Jun. 25, 2012 From the European Patent Office Re. Application No. 04744911.1.
Official Action dated Jun. 22, 2012 From the US Patent and Trademark Office Re. U.S. Appl. No. 13/019,320.
Lee et al. "An Equibiaxial Strain System for Cultured Cells", The American Journal of Physiology, XP008152868, 271(4): C1400-C1408, Oct. 1996.
Tschumperlin et al. "Equibiaxial Deformation-Induced Injury of Alveolar Epithelial Cells In Vitro", American Journal of Physiology, 275(6/Pt.1): L1173-L1183, Jan. 1, 1998.
Response dated Jun. 9, 2011 to Official Action dated 9 Dec. 9, 2010 From the US Patent and Trademark Office Re. U.S. Appl. No. 10/565,240.
Communication Relating to the Results of the Partial International Search dated May 20, 2009 From the International Searching Authority Re.: Application No. PCT/IL2008/001678.
Response dated Jun. 7, 2010 to Official Action dated Mar. 5, 2010 From the US Patent and Trademark Office Re.: U.S. Appl. No. 10/561,839.
Response dated Jun. 29, 2011 to Official Action dated Mar. 31, 2011 From the US Patent and Trademark Office Re.: U.S. Appl. No. 10/492,531.
Response dated Jul. 12, 2011 to Official Action dated Mar. 16, 2011 From the US Patent and Trademark Office Re. U.S. Appl. No. 10/561,839.
Response dated Jun. 28, 2011 to Invitation Pursuant to Rule 63(1) EPC of May 3, 2011 From the European Patent Office Re. Application No. 10183774.8.
European Search Report and the European Search Opinion dated Aug. 1, 2011 From the European Patent Office Re. Application No. 10183774.8.
Office Action dated Apr. 12, 2011 From the Israel Patent Office Re.: Application No. 173170 and Its Translation Into English.
Gonzalez et al. "Cell-Based Assays and Instrumentation for Screening Ion-Channels Targets", Drug Discovery Today, DDT, XP001026838, 4(9): 431-439, Sep. 1, 1999.
Official Action dated Jul. 30, 2012 From the US Patent and Trademark Office Re. U.S. Appl. No. 12/155,643.
Official Action dated Aug. 2, 2012 From the US Patent and Trademark Office Re. U.S. Appl. No. 12/712,232.

(56) References Cited

OTHER PUBLICATIONS

Communication Pursuant to Article 94(3) EPC dated Aug. 9, 2010 From the European Patent Office Re. Application No. 01982673.4.
Official Action dated Jul. 21, 2011 From the US Patent and Trademark Office Re. U.S. Appl. No. 12/712,232.
Communication Pursuant to Article 94(3) EPC dated Aug. 4, 2011 From the European Patent Office Re. Application No. 08865081.7.
Communication Pursuant to Article 94(3) EPC dated Aug. 6, 2010 From the European Patent Office Re.: Application No. 04714873.9.
Office Action dated Jul. 1, 2010 From the Israeli Patent Office Re.: Application No. 172724 and Its Translation Into English.
Official Action dated Aug. 17, 2010 From the US Patent and Trademark Office Re.: U.S. Appl. No. 10/561,839.
Notice of Non-Compliant Amendment dated Aug. 18, 2011 From the US Patent and Trademark Office Re.: U.S. Appl. No. 12/084,462.
Notice of Non-Compliant Amendment dated Aug. 24, 2011 From the US Patent and Trademark Office Re. U.S. Appl. No. 10/565,240.
Reponse dated Aug. 4, 2011 to Official Action dated Apr. 15, 2011 From the US Patent and Trademark Office Re.: U.S. Appl. No. 12/084,462.
Response dated Aug. 4, 2011 to Official Action dated May 23, 2011 From the US Patent and Trademark Office Re.: U.S. Appl. No. 11/646,317.
Response dated Aug. 17, 2011 to Office Action dated Apr. 12, 2011 From the Israel Patent Office Re.: Application No. 173170.
Response dated Aug. 22, 2011 to Official Action dated Apr. 22, 2011 From the US Patent and Trademark Office Re.: U.S. Appl. No. 11/646,294.
Communication Pursuant to Article 94(3) EPC dated Aug. 5, 2010 From the European Patent Office Re. Application No. 05757567.2.
Notice of Allowance dated Jun. 15, 2010 From the US Patent and Trademark Office Re. U.S. Appl. No. 11/940,996.
Translation of Notice of Reason for Rejection dated Jul. 23, 2010 From the Japanese Patent Office Re.: Application No. 2006-502647.
Communication Pursuant to Article 94(3) EPC dated Aug. 29, 2011 From the European Patent Office Re. Application No. 04745001.0.
Communication Pursuant to Rules 70(2) and 70a(2) EPC dated Aug. 20, 2012 From the European Patent Office Re. Application No. 08848869.7.
Office Action dated Aug. 12, 2012 From the Israeli Patent Office Re.: Application No. 172724 and Its Translation Into English.
Supplementary European Search Report and the European Search Opinion dated Aug. 1, 2012 From the European Patent Office Re. Application No. 08848869.7.
Response dated Aug. 30, 2010 to Official Action dated Jul. 13, 2009 From the US Patent and Trademark Office Re.: U.S. Appl. No. 11/660,783.
Response dated Aug. 30, 2010 to Official Action dated Feb. 23, 2010 From the US Patent and Trademark Office Re.: U.S. Appl. No. 12/084,462.
Official Action dated Sep. 2, 2010 From the US Patent and Trademark Office Re. U.S. Appl. No. 10/565,240.
Response dated Sep. 6, 2011 to Notice of Non-Compliant Amendment dated Aug. 24, 2011 From the US Patent and Trademark Office Re. U.S. Appl. No. 10/565,240.
Communication Pursuant to Article 94(3) EPC dated Sep. 6, 2012 From the European Patent Office Re. Application No. 10183774.8.
Official Action dated Aug. 31, 2011 From the US Patent and Trademark Office Re.: U.S. Appl. No. 11/660,783.
Response dated Sep. 19, 2011 to Notice of Non-Compliant Amendment dated Aug. 18, 2011 From the US Patent and Trademark Office Re.: U.S. Appl. No. 12/084,462.
Official Action dated Sep. 10, 2010 From the US Patent and Trademark Office Re.: U.S. Appl. No. 11/646,317.
Official Action dated Sep. 22, 2011 From the US Patent and Trademark Office Re.: U.S. Appl. No. 11/646,294.
Communication Pursuant to Rules 161(1) and 162 EPC dated Aug. 25, 2010 From the European Patent Office Re. Application No. 08865081.7.
Official Action dated Sep. 14, 2010 From the US Patent and Trademark Office Re.: U.S. Appl. No. 11/631,737.
Response dated Sep. 21, 2010 to Communication Pursuant to Rules 161(1) and 162 EPC dated Aug. 25, 2010 From the European Patent Office Re. Application No. 08865081.7.
Official Action dated Sep. 29, 2010 From the US Patent and Trademark Office Re.: U.S. Appl. No. 11/883,028.
Communication Pursuant to Article 94(3) EPC dated Sep. 26, 2012 From the European Patent Office Re. Application No. 04714873.9.
Official Action dated Sep. 23, 2010 From the US Patent and Trademark Office Re.: U.S. Appl. No. 10/492,531.
Official Action dated Sep. 23, 2010 From the US Patent and Trademark Office Re.: U.S. Appl. No. 11/646,294.
Communication Pursuant to Rules 70(2) and 70a(2) EPC and Reference to Rule 39(1) EPC dated Sep. 5, 2011 From the European Patent Office Re. Application No. 10183774.8.
Official Action dated Oct. 18, 2011 From the US Patent and Trademark Office Re.: U.S. Appl. No. 11/631,737.
Official Action dated Oct. 18, 2011 From the US Patent and Trademark Office Re.: U.S. Appl. No. 12/084,462.
Official Action dated Oct. 19, 2011 From the US Patent and Trademark Office Re. U.S. Appl. No. 12/155,643.
Office Action dated Sep. 20, 2012 From the Israel Patent Office Re. Application No. 138314.
Office Action dated Oct. 5, 2010 From the Israel Patent Office Re. Application No. 184818 and Its Translation Into English.
Response dated Oct. 4, 2010 to Official Action dated Sep. 2, 2010 From the US Patent and Trademark Office Re. U.S. Appl. No. 10/565,240.
Official Action dated Sep. 28, 2012 From the US Patent and Trademark Office Re. U.S. Appl. No. 10/561,839.
Response Dated Oct. 10, 2010 to Notice of Reason for Rejection dated Jul. 23, 2010 From the Japanese Patent Office Re.: Application No. 2006-502647.
Partial European Search Report dated Oct. 27, 2011 From the European Patent Office Re. Application No. 11170000.1.
Tixier et al. Catching and Attaching Cells Using an Array of Microholes, Abstract of the 2nd Conference of the Society for Chemistry and Micro Systems, p. 60, 2000.
Communication Pursuant to Article 94(3) EPC dated Nov. 16, 2011 From the European Patent Office Re. Application No. 04744911.1.
Response dated Nov. 1, 2011 to Official Action dated Oct. 19, 2011 From the US Patent and Trademark Office Re. U.S. Appl. No. 12/155,643.
Official Action dated Nov. 14, 2012 From the US Patent and Trademark Office Re. U.S. Appl. No. 13/184,631.
Official Action dated Nov. 16, 2012 From the US Patent and Trademark Office Re. U.S. Appl. No. 12/742,730.
Response dated Nov. 21, 2011 to Communication Pursuant to Article 94(3) EPC dated Aug. 4, 2011 From the European Patent Office Re. Application No. 08865081.7.
Communication Pursuant to Article 94(3) EPC dated Nov. 23, 2012 From the European Patent Office Re. Application No. 01982673.4.
Response dated Nov. 30, 2011 to Office Action dated Jul. 1, 2010 From the Israeli Patent Office Re.: Application No. 172724.
Response dated Oct. 31, 2011 to Official Action dated Jul. 21, 2011 From the US Patent and Trademark Office Re. U.S. Appl. No. 12/712,232.
Communication Pursuant to Article 94(3) EPC dated Dec. 2, 2011 From the European Patent Office Re.: Application No. 04714873.9.
Official Action dated Nov. 22, 2011 From the US Patent and Trademark Office Re.: U.S. Appl. No. 11/646,317.
Official Action dated Nov. 23, 2011 From the US Patent and Trademark Office Re.: U.S. Appl. No. 10/561,839.
Official Action dated Oct. 27, 2010 From the US Patent and Trademark Office Re.: U.S. Appl. No. 12/890,668.
Official Action dated Dec. 16, 2012 From the US Patent and Trademark Office Re. U.S. Appl. No. 13/019,320.
Invitation Pursuant to Article 94(3) and Rule 71(1) EPC dated Jun. 25, 2013 From the European Patent Office Re. Application No. 04744911.1.
Official Action dated Jun. 20, 2013 From the US Patent and Trademark Office Re. U.S. Appl. No. 12/155,643.

(56) References Cited

OTHER PUBLICATIONS

Gelest "Optical Materials", 'Gelest', Enabling Your Technology, Downloaded from Internet, 36 P., 2007.
Restriction Official Action dated Apr. 25, 2013 From the US Patent and Trademark Office Re. U.S. Appl. No. 13/651,522.
Official Action dated May 14, 2013 From the US Patent and Trademark Office Re. U.S. Appl. No. 12/742,730.
Office Action dated Apr. 12, 2011 From the Israel Patent Office Re. Application No. 173170 and Its Translation Into English.
Notice of Allowance dated Apr. 1, 2013 From the US Patent and Trademark Office Re. U.S. Appl. No. 13/184,631.
Official Action dated Mar. 15, 2013 From the US Patent and Trademark Office Re. U.S. Appl. No. 13/019,320.
Official Action dated Feb. 11, 2013 From the US Patent and Trademark Office Re. U.S. Appl. No. 12/742,730.
Official Action dated Mar. 13, 2013 From the US Patent and Trademark Office Re.: U.S. Appl. No. 10/492,531.
Communication Pursuant to Article 94(3) EPC dated Oct. 4, 2013 From the European Patent Office Re. Application No. 04745001.0.
Official Action dated Nov. 21, 2013 From the US Patent and Trademark Office Re. U.S. Appl. No. 13/019,320.
Official Action dated Jul. 15, 2014 From the US Patent and Trademark Office Re. U.S. Appl. No. 10/565,240. (Part I).
Official Action dated Jul. 15, 2014 From the US Patent and Trademark Office Re. U.S. Appl. No. 10/565,240. (Part II).
Advisory Action Before the Filing of an Appeal Brief dated Aug. 29, 2013 From the US Patent and Trademark Office Re. U.S. Appl. No. 13/019,320.
Notice of Allowance dated Jul. 22, 2013 From the US Patent and Trademark Office Re. U.S. Appl. No. 12/742,730.
Official Action dated Sep. 27, 2013 From the US Patent and Trademark Office Re. U.S. Appl. No. 13/651,522.
Official Action dated Jul. 29, 2013 From the US Patent and Trademark Office Re. U.S. Appl. No. 12/712,232.
Official Action dated Sep. 30, 2013 From the US Patent and Trademark Office Re. U.S. Appl. No. 10/561,839.
Summons to Attend Oral Proceedings Pursuant to Rule 115(1) EPC Dated Aug. 14, 2013 From the European Patent Office Re. Application No. 01982673.4.
Summons to Attend Oral Proceedings Pursuant to Rule 115(1) EPC Dated Aug. 14, 2013 From the European Patent Office Re. Application No. 10183774.8.
Office Action dated May 16, 2013 From the Israel Patent Office Re. Application No. 173170 and Its Translation Into English.
Official Action dated Jan. 29, 2015 From the US Patent and Trademark Office Re. U.S. Appl. No. 10/565,240.
Advisory Action Before the Filing of an Appeal Brief dated Apr. 17, 2015 From the US Patent and Trademark Office Re. U.S. Appl. No. 10/565,240.
Applicant-Initiated Interview Summary dated Jun. 11, 2015 From the US Patent and Trademark Office Re. U.S. Appl. No. 10/565,240.
Notice of Allowance dated May 27, 2015 From the US Patent and Trademark Office Re. U.S. Appl. No. 12/712,232.
Office Action dated Jul. 8, 2015 From the Israel Patent Office Re. Application No. 224263 and Its Translation Into English.
Office Action dated Apr. 21, 2016 From the Israel Patent Office Re. Application No. 224263 and its Translation into English.
Official Action dated Nov. 22, 2016 From the US Patent and Trademark Office Re. U.S. Appl. No. 14/840,065. (78 pages).
Office Action dated Apr. 21, 2016 From the Israel Patent Office Re. Application No. 224263.
Restriction Official Action dated Aug. 9, 2017 From the US Patent and Trademark Office Re. U.S. Appl. No. 14/883,659. (7 pages).
Official Action dated Dec. 14, 2017 From the US Patent and Trademark Office Re. U.S. Appl. No. 14/883,659. (85 pages).

* cited by examiner

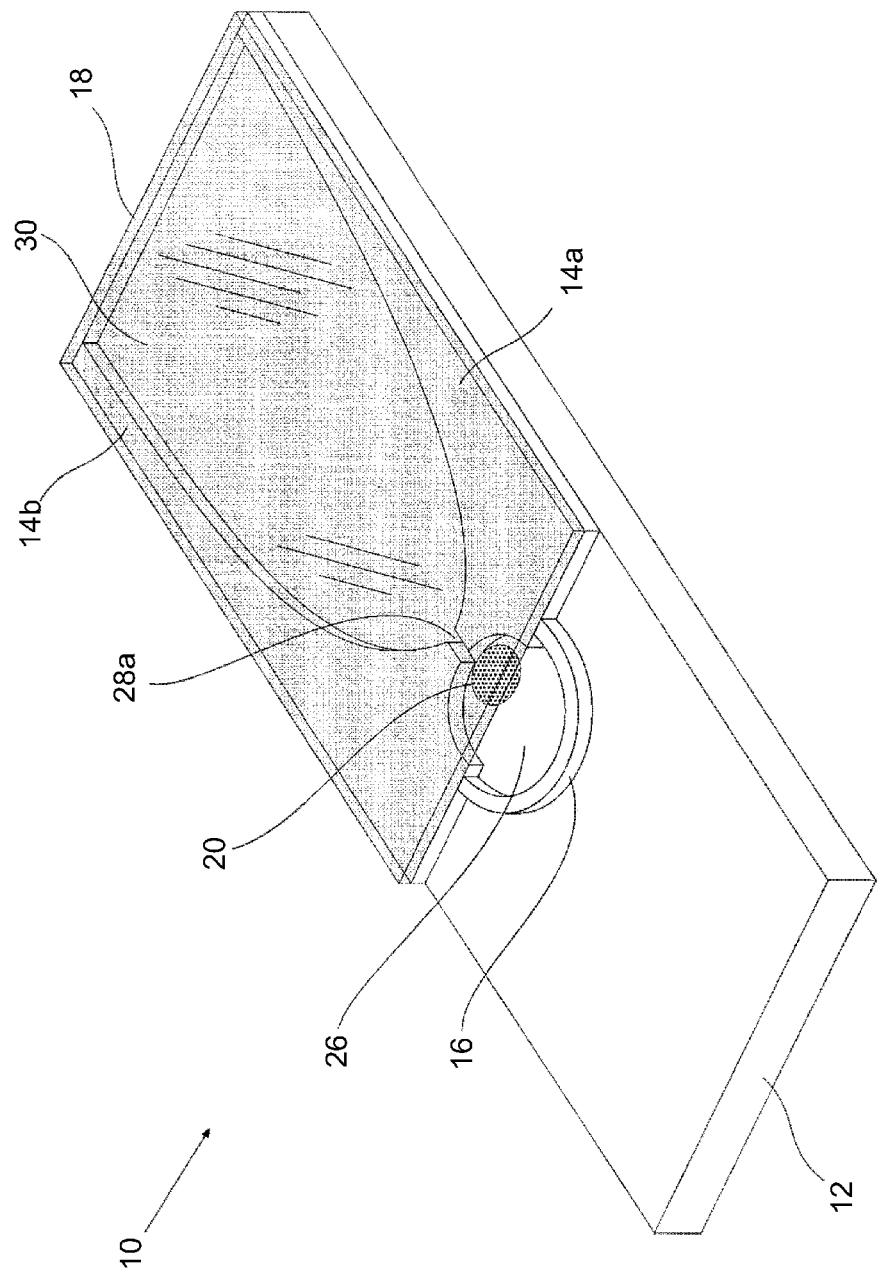

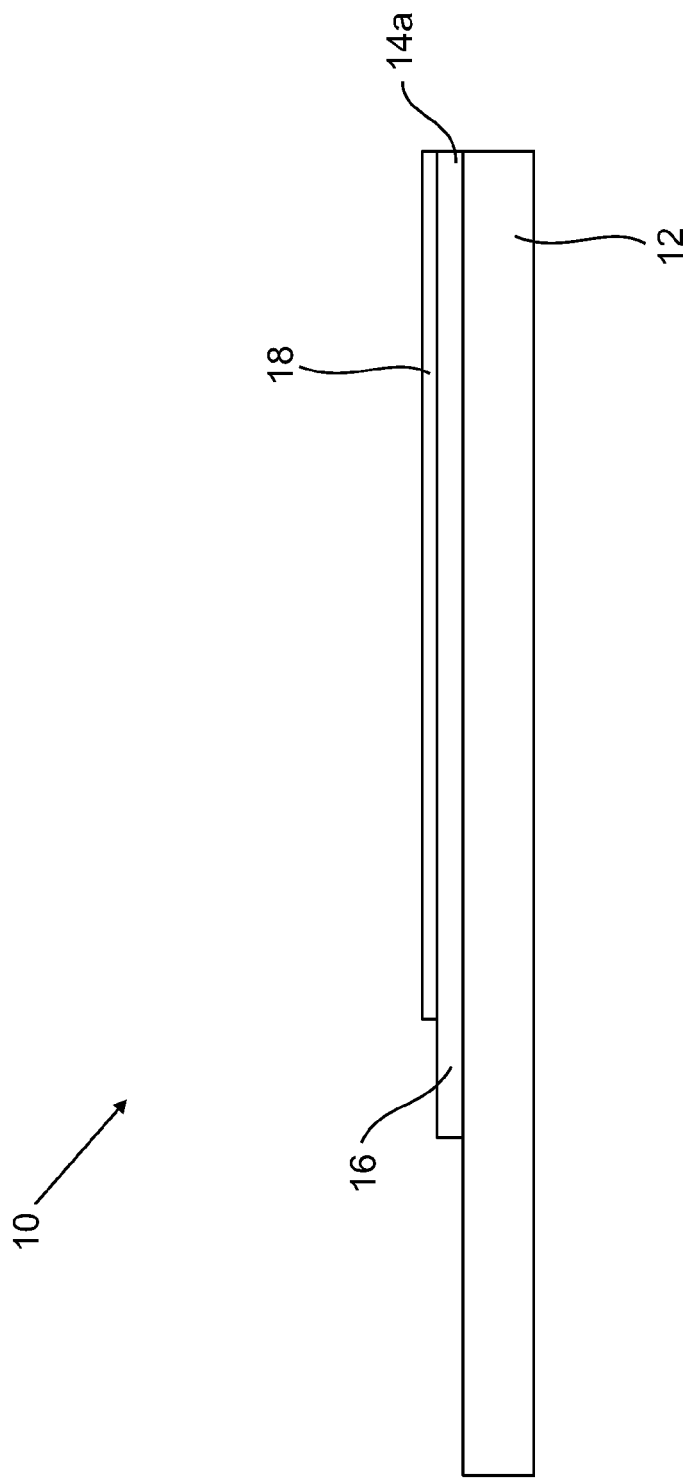

DEVICE FOR THE STUDY OF LIVING CELLS

RELATED APPLICATIONS

This application is a National Phase of PCT Patent Application No. PCT/IL2008/001678 having International filing date of Dec. 25, 2008, which is a continuation-in-part (CIP) of PCT Patent Application No. PCT/IL2008/001492 filed Nov. 13, 2008, which is a continuation-in-part (CIP) of U.S. patent application Ser. No. 11/940,996 filed Nov. 15, 2007.

PCT Patent Application Nos. PCT/IL2008/001678 and PCT/IL2008/001492 both claim the benefit of priority under 35 USC 119(e) of U.S. Provisional Patent Application No. 61/006,130 filed Dec. 26, 2007.

This application is also a continuation-in-part (CIP) of U.S. patent application Ser. No. 12/712,232 filed Feb. 25, 2010, which claims the benefit of priority under 35 USC 119(e) of U.S. Provisional Patent Application No. 61/155,186 filed Feb. 25, 2009.

U.S. patent application Ser. No. 12/712,232 is also a continuation-in-part (CIP) of PCT Patent Application No. PCT/IL2008/001678.

The contents of the above applications are incorporated herein by reference in their entirety.

FIELD OF THE INVENTION

The present invention, in some embodiments thereof, relates to the field of devices for biology, and more particularly, but not exclusively, to devices useful for the study and/or maintenance of a plurality living cells.

BACKGROUND OF THE INVENTION

The study of cell behavior is important in many fields including biology, medicine and pharmacology. Since cell-functions include many interrelated pathways, cycles and chemical reactions and since there is a large variation of cell biochemistry amongst similar cells, the study of a bulk of cells, whether the bulk is homogenous or heterogeneous, does not usually provide sufficiently detailed or interpretable results: rather a comprehensive study of cell biological activity is often advantageously performed by examining single isolated living cells as individuals. The use of single-cell assays is an important tool for understanding biological systems and the influence thereupon of various stimuli such as exposure to active entities.

In order to understand cell behavior, for example, such as the response to stimuli such as various biological modulators, two fundamental research capabilities are often desirable (i) the ability to track temporal behavior of large groups of cells as individuals for periods of minutes, hours and even days and (ii) the ability to identify and study cell heterogenity, a phenomenon existing even in synchronized cell lines.

SUMMARY OF THE INVENTION

Some embodiments of the present invention provide a device including an array of wells and capillary channels to lead fluid form and to the cells, optionally formed on a glass slide and being useful the study of a plurality of cells as individuals. In an exemplary embodiment of the invention, the device is constructed of materials and has a structure selected so that the device has a desired degree of capillary flow. In an exemplary embodiment of the invention, the device is formed of multiple layers with apertures therein, laid one on the other and defining capillary flow in spaces between.

There is provided in accordance with an exemplary embodiment of the invention, a cell study device, comprising:

a base layer;

a planar conduit defining layer, including a conduit cut out of the layer; and a planar cover layer which defines a capillary flow channel in said conduit layer, said conduit layer and said cover layer acting as side walls for said capillary flow channel, wherein said layers are formed of materials that do not interfere with cell behavior over a period of at least 5 hours when loaded with aqueous solution.

In an exemplary embodiment of the invention, the device comprises a cell holding area defined in fluid contact with said capillary flow channel. Optionally, said cell holding area includes at least one orientation mark visible under microscopy. Optionally or alternatively, said cell holding area is masked by a masking layer underlying said conduit layer.

In an exemplary embodiment of the invention, said cell holding area is mounted on said base layer.

In an exemplary embodiment of the invention, said cover layer includes an air hole for air release form said capillary flow channel.

In an exemplary embodiment of the invention, said capillary flow channel defines a substantially sealed waste reservoir with no fluid exit.

In an exemplary embodiment of the invention, said capillary flow channel defines a substantially sealed waste reservoir with an absorbent material as a fluid exit.

In an exemplary embodiment of the invention, said cover defines a fluid inlet area for said capillary flow conduit.

In an exemplary embodiment of the invention, said device is packaged in vacuum.

In an exemplary embodiment of the invention, said conduit layer is permanently adhesive to said cover layer. Optionally, said device is provided with a removable non-stick layer intermediate most of said cover layer and said conduit layer.

In an exemplary embodiment of the invention, said conduit layer is temporarily adhesive to said cover layer.

In an exemplary embodiment of the invention, said device is formed essentially of layered planar layers.

In an exemplary embodiment of the invention, said conduit layer is adhesive on both its faces.

In an exemplary embodiment of the invention, said layers are selected of dissimilar materials with dissimilar contact angles with fluids.

In an exemplary embodiment of the invention, said device has the form factor of a standard microscope slide.

In an exemplary embodiment of the invention, said device has the form factor of a standard microtitter plate.

In an exemplary embodiment of the invention, said materials do not interfere for at least 24 hours.

In an exemplary embodiment of the invention, said cover layer is openable for access to said capillary conduit and removal of cells therefrom.

There is provided in accordance with an exemplary embodiment of the invention, a kit, comprising:

(a) a cell study device including a capillary flow conduit and a cell holding area; and (b) at least an indication of one or both of a capillary flow rate and a cell dislocation rate therein. Optionally, the kit comprises a plurality of different cell study devices, each with different sets of flow rate and dislocation rate. Optionally or alternatively, said indication is per one or both of fluid property and cell type. Optionally or alternatively, said indication comprises a machine input indication. Optionally or alternatively, said indication comprises a human readable indication.

In an exemplary embodiment of the invention, the kit comprises instructions explaining said indications.

In an exemplary embodiment of the invention, the kit comprises software on a computer readable media for using said indications.

There is provided in accordance with an exemplary embodiment of the invention, a pre-assembled and packaged cell study device including:
  a capillary flow conduit;
  a cell holding area; and
  at least one non-adhesive layer, designed for removal and interfering with adhesion of at least two parts of said device, said interfering inactivating said capillary flow conduit. Optionally, said adhesion is permanent, when said non-adhesive interfering layer is removed.

There is provided in accordance with an exemplary embodiment of the invention, a method of assembling a cell study device, comprising:
  (a) selecting desired device characteristics;
  (b) selecting device components from a set of pre-manufactured components, said selected components selected to interact to provide said characteristics; and
  (c) assembling said components to provide said device with said desired characteristics.

In an exemplary embodiment of the invention, said set includes components of difference wettability. Optionally or alternatively, said set includes components defining different capillary flow conduit geometries. Optionally or alternatively, said set includes components defining different cell holding area geometries.

There is provided in accordance with an exemplary embodiment of the invention, a cell study device, comprising:
  a capillary flow conduit having an inlet, enclosed on four sides and sealed on a distal end; and
  at least one air release aperture defined in a top of said conduit.

There is provided in accordance with an exemplary embodiment of the invention, a cell study device, comprising:
  at least one array of cell holders;
  a double sided adhesive layer masking some of said cell holders; and
  a layer defining one or both of capillary channels and walls mounted on said adhesive layer. Optionally, said device comprises a plurality of fluidicly disconnected cell holder arrays. Optionally or alternatively, said adhesive layer is apertured. Optionally or alternatively, said walls are at least 2 mm high.

There is provided in accordance with an exemplary embodiment of the invention, a method of forming a cell study device, comprising adhering a plurality of precut dry or wet layers by applying pressure and defining at least one capillary flow channel between layers, thereby. Optionally, the method comprises:
  annealing said device under heat;
  soaking said device in a solvent matched to said adhering; and
  washing away said solvent.

In an exemplary embodiment of the invention, the method comprises embossing a cell holding area on said device.

In an exemplary embodiment of the invention, the method comprises essentially of said adhering In an exemplary embodiment of the invention, said adhering comprises adhering, or post treatment, in a low atmospheric pressure condition.

There is provide din accordance with an exemplary embodiment of the invention a method of studying cells, comprising:
  (i) determining one or both of desired flow rates for fluid used during a study and a rate of cell dislocations for a cell type or aggregate used during the study;
  (ii) selecting a cell study device including a capillary flow conduit and a cell holding area to match said determinations; and
  (iii) using said selected device with said cell type in said study.

In an exemplary embodiment of the invention, selecting comprises selecting from a plurality of devices in a kit.

In an exemplary embodiment of the invention, selecting comprises selecting according to a catalog.

In an exemplary embodiment of the invention, selecting comprises recommending by a computer.

In an exemplary embodiment of the invention, selecting comprises a device according to a contact angle between fluid used in the study and said capillary flow conduit.

In an exemplary embodiment of the invention, selecting comprises a device according to a conduit cross-section.

In an exemplary embodiment of the invention, said device has a capillary flow rate of less than 1 micro-liter per second.

In an exemplary embodiment of the invention, said device has a cell dislocation rate of less than 10% per said study.

In an exemplary embodiment of the invention, said device includes at least one baffle to control capillary flow rate.

In an exemplary embodiment of the invention, said device includes a substantially sealed exit reservoir with at least one air hole to control capillary flow rate.

In an exemplary embodiment of the invention, said device includes side walls in said capillary flow conduit which control capillary flow rate.

In an exemplary embodiment of the invention, said device includes one or more changes in geometry at said cell holding area, which changes control cell dislocation rate.

In an exemplary embodiment of the invention, said device allows application of cells directly to said cell holding area without capillary flow.

In an exemplary embodiment of the invention, said selecting comprises selecting according to a desired delivery rate of cells along said capillary flow to said cell holding area.

In an exemplary embodiment of the invention, said cell holding area comprises non-adhesive picowells.

In an exemplary embodiment of the invention, the method comprises modifying a fluid used during a study to maintain said desired rate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE FIGURES

Some embodiments of the invention are herein described, by way of example only, with reference to the accompanying Figures. With specific reference now to the drawings in detail, it is stressed that the particulars shown are by way of example and for purposes of illustrative discussion of some embodiments of the invention. In this regard, the description taken with the Figures makes apparent to those skilled in the art how some embodiments of the invention may be practiced.

In the Figures:

FIGS. 2 and 3 are schematic depictions of a device for the study of cells, in accordance with an exemplary embodiment of the invention;

DESCRIPTION OF SPECIFIC EMBODIMENTS OF THE INVENTION

Figure 1A:
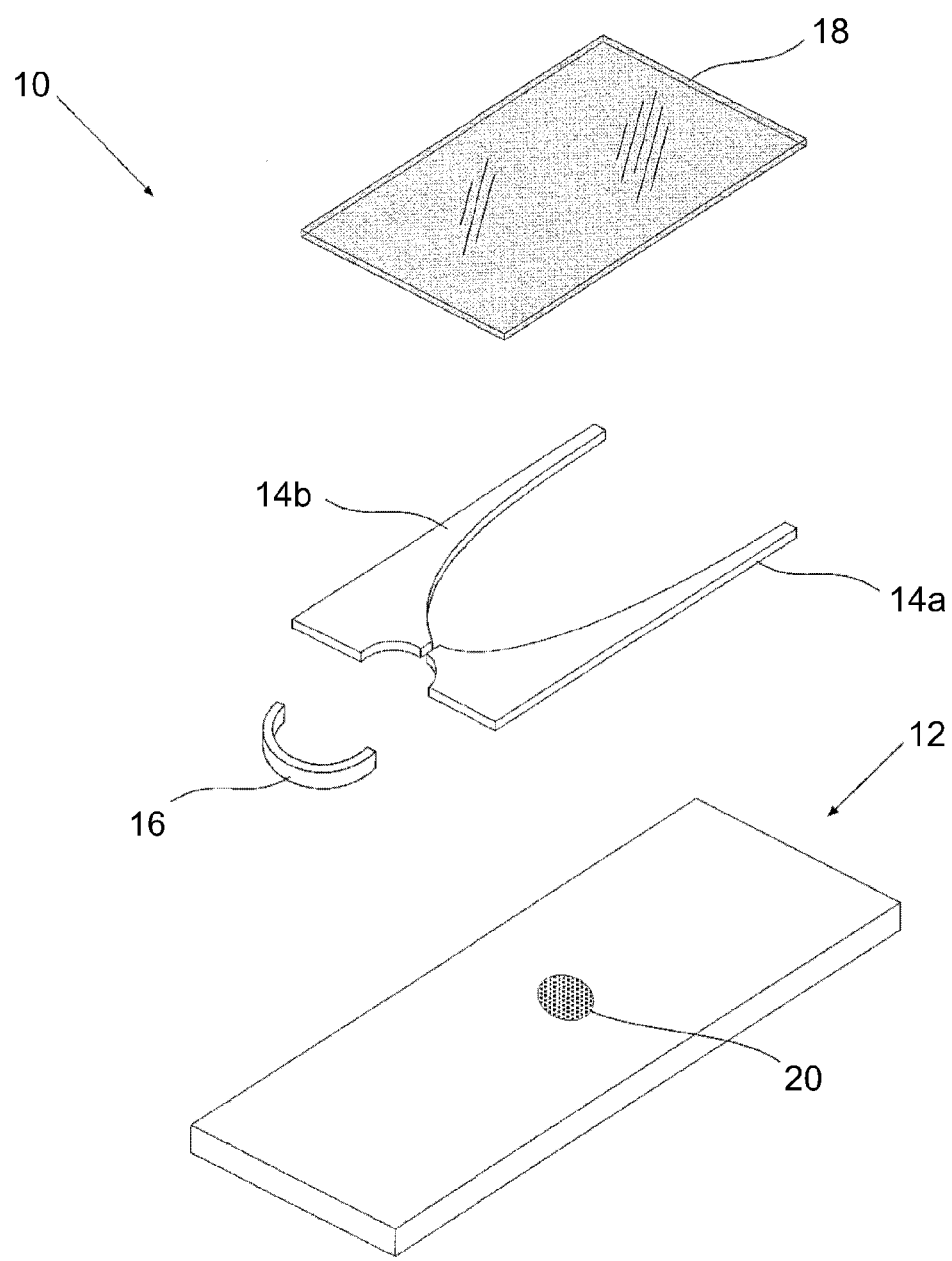
FIG. 1A is a schematic depiction of a device useful for the study of cells, disassembled to show components thereof, in accordance with an exemplary embodiment of the invention.

The present invention, in some embodiments thereof, relates to the study of living cells and, more particularly, but not exclusively, to a device including an array of wells, the device useful the study of a plurality of cells as individuals. In an exemplary embodiment of the invention, what is provided is means and methods and methods of manufacture, of a support system including capillary flow to and from a cell study area.

In an exemplary embodiment of the invention, what is provided is a microscope slide including a picowell array and using capillary action to provide fluid to and from the well array. Optionally, the rate of flow is controlled by design methods and/or by user selection. Optionally, the device is pre-assembled. Optionally or alternatively, the device is formed of a plurality of planar layers with apertures formed therein. Optionally, one of the apertures serves to mask an underlying cell holding array. Optionally or alternatively, the apertures define one or more capillary flow channels. Optionally or alternatively, the apertures define an air release opening.

In an exemplary embodiment of the invention, the device is designed to be a single piece device with a cover which can seal to underlying layers and define capillary conduits therewith. Optionally, a separating layer is provided between the cover and underlying layers, at least over part of their interface, and is selectively removed by a user, during use.

In an exemplary embodiment of the invention, at least some of the layers are adhesive layers.

In an exemplary embodiment of the invention, what is provided is a high-content single live cell assay device which allows the study of real-time responses to stimuli in large and heterogeneous cell populations at an individual cell level. Such a device may be used to one or more of:

study each cell from a plurality of cells as an individual, observing the real-time response of the cells to intervention using probes to monitor morphological responses, intracellular and extra-cellular parameters, as well as cell-cell interaction;

perform long-term, non-intrusive, repeated measurements on intact, living, adherent or non-adherent cells, including bone marrow cells;

perform multiple functional assays on living cells, followed by immuno-staining and chromatic staining on the same cells following fixation;

perform kinetic measurements of non-synchronous activities in individual cells;

analyze and compare actual quantitative measurements of sub-populations and individual cells as opposed to recording the mean values of entire population; and/or perform quantitative measurements on a cellular-to-molecular level, for example, assays, killing cells in situ and then bursting them in situ for further analysis, feeding cells various substrates and/or exposing individual or groups of cells to various stimulus. In some embodiments, the cell holding sections include both individuals cells and groups of cells, for example, in different parts of the cell holding area.

Some devices and methods for multiple single cell study are taught in the PCT Patent Applications published as WO2003/035824, WO2004/113492, WO2005/007796, WO2006/003664, WO2006/080000 and WO2007/052245 which include Inventor Mordechai Deutsch, all of which are included by reference as if fully set forth herein. Features of such devices may be used in accordance with some exemplary embodiments of the invention.

"For example, WO2006/080000 describes "It is important to note that some embodiments of the present invention are related to embodiments of unpublished copending PCT Patent Application No. IL04/00571 of the Applicant filed 27 Jun. 2004. In PCT Patent Application No. IL04/00571 are taught picowell-bearing carriers having a variety of innovative features. One aspect of the teachings of PCT Patent Application No. IL04/00571 is of picowells configured to influence cell proliferation of cells held therein. In one embodiment, carriers having picowells of a changeable size is taught. In another embodiment, carriers configured to delay proliferation of cells held therein, for example by delaying or preventing cell adhesion, are taught. In another embodiment, carriers configured so as to allow cells to grow into or through the carrier are taught. The above-described embodiments are preferably implemented by making the picowells of or coating the picowells with a material with the desired properties. In some embodiments, the inner surface of a picowell with which a held cell makes contact is configured to have the desired property, influence or effect.

Preferred materials from which to make carriers listed in PCT Patent Application No. IL04/00571 include polydimethylsiloxane, elastomers (such as silicon rubber), polymerized para-xylylene molecules, polymerized derivatives of para-xylylene molecules and gels (especially hydrogels). In some embodiments, the inner surface of a picowell with which a held cell makes contact is configured to have the desired property, influence or effect.

An additional aspect of PCT Patent Application No. IL04/00571 is the teaching of a gel cover for picowell-bearing components. The gel cover is configured to prevent cells held in a picowell from exiting the picowell due to jostling, incidental fluid flows or during movement of the carrier.
The advantages of a picowell-bearing carrier made of a gel, of a picowell gel-cover or a gel carrier covered with a gel cover include, depending on the embodiment, that active entities may be integrated into the gel, that active entities may be contacted with the cell by diffusion through the gel, that diffusion of released compounds is slowed down allowing identification of which cell released a given compound, that proliferation of cells held therein is delayed but once cells begin to proliferate, that allows proliferation into and through the gel matrix".

In an exemplary embodiment of the invention, devices for the study of cells include a picowell-bearing component. In some embodiments, a picowell-bearing component is a component having at least one, but generally a plurality of picowells, each picowell configured to hold at least one cell. The term "picowell" is general and refers to a "small well", that is physical feature that localizes a cell (or group of cells) to a specific area on a planar surface of the picowell-bearing component using by physical confinement. In some embodiments, a picowell-bearing component is a "carrier", a substantially planar component such as a chip, plate, sheet or slide. The term "picowell" is generally a discrete cavity of a size and shape suitable for retaining cells therein where the size and shape are defined by some physical features such as walls. The term "picowell" includes physical features such as wells, dimples, depressions, pits, tubes and enclosures.

Since cells (or cell spheroids) typically range in size from about 1 micrometers to about 400 (e.g., oocytes) micrometers diameter there is may not be a single picowell size that is appropriate for holding a single cell of any type. That said, the dimensions of the typical individual picowell in the picowell-bearing components optionally have dimensions suitable for accommodating cells having diameters of between about 1 micrometer up to about 500 micrometers, depending on the exact implementation, for example round or hexagonal picowells having a diameter of from about 1 micrometer up to about 500 micrometers. For example, a picowell-bearing component of a device designed for the study of single isolated 8 to 20 micrometer diameter cells typically has picowells of dimensions of about 20 micrometers. In some embodiments, larger picowells are used to study the interactions of a few cells held together in one picowell. For example, a 200 micrometer picowell is recognized as being useful for the study of cell spheroids or the interactions of two, three or more cells, for example, as discussed in the PCT Patent Application published as WO 2003/035824.

A feature that increases the utility of some embodiments of the picowell-bearing devices is that the picowells are juxtaposed, that is to say the walls separating the individual picowells are thin (relative to the size of the picowells) so that the area occupied by a picowell-array is substantially entirely made up of picowells with little or no inter picowell area. In an exemplary embodiment of the invention, walls separating picowells are less than 1 micrometer wide so that the inter-picowell area of the picowell array makes up only a minor percentage of the total area of the picowell-array. This feature can allow near tissue-density packing of cells, especially in embodiments configured to hold a single cell in each picowell.

In an exemplary embodiment of the invention, at least some of the picowells are not etched or embossed and therefore are full and are optionally used for optical alignment and/or as landmarks.

In an exemplary embodiment of the invention, a 2.2 mm by 2.2 mm picowell-array of hexagonally-packed juxtaposed picowells having a 10 micrometer diameter includes about 61,600 picowells. Optionally or alternatively, this feature allows simple loading of the picowells with cells: a liquid containing suspended cells is introduced in the volume above picowells of the appropriate size. Since there is little inter-picowell area, cells, when they settle, mostly settle in the picowells. After the cells settle, a flow of liquid applied in parallel to the surface of the picowell array either washes away cells resting on a wall separating picowells or leaning on another cell in a picowell, or pushes such a cell into an unoccupied picowell. In such a way, the only cells in the proximity of the picowell array are cells held in a picowell, where each picowell holds only the number of cells for which it is configured, for example, one cell per picowell, two cells per picowell or three cells per picowell.

In an exemplary embodiment of the invention, the picowell-bearing component is a thin, transparent carrier and the cells are observed from below with an inverted microscope or similar device, for example by detection of light emitted by fluorescence or direct optical observation of the cells. In such embodiments, it is important that the bottoms of the picowells on which the cells rest be as coplanar as possible: coplanarity allows for optical observation of many cells (whether by scanning or simultaneously using a wide-angle observation component) without the need for time consuming and difficult-to-implement refocusing. In such embodiments it is also important that the carrier be as flat and planar as possible, be of a uniform thickness and be as homogenous as possible so that the carrier be as optically neutral as possible, to allow observation of the cells with as little distortion as possible.

In an exemplary embodiment of the invention, imaging is form above, for example, if the device is configured as a microscope slide, for example, in size, shape and transparency, or in another standard form factor, such as a microtitter plate or any other common lab substrate.

In an exemplary embodiment of the invention, the use of a device for studying cells including a picowell-bearing component typically involves loading picowells with cells in a physiological medium and then observing the cells as individuals while exposing the cells to various stimuli to study the effect of the stimuli on the individual cells.

In some instances, it is desirable to expose cells to a first stimulus, for example to a first medium containing a first active agent and after a time to expose the cells to a second stimulus, for example to a second medium containing a second active agent. In an exemplary embodiment of the invention, the first medium is preferably entirely replaced with the second medium in proximity with the cells held in the picowell array.

In an exemplary embodiment of the invention, a device is provided where a picowell array is in fluid communication with an inlet reservoir through a capillary inlet and with a waste reservoir through a capillary outlet. Liquid such as a first medium is added in the inlet reservoir and drawn by capillary action to and past the picowell array and to the waste reservoir, optionally without needing pumps or complex interfaces. When the inlet reservoir is empty, a second medium is added to the inlet reservoir and drawn by capillary action to displace the first medium to and past the picowell array and to the waste reservoir. A device including a picowell array in contact with flow is shown in the PCT patent application published as WO2006/080000. In an exemplary embodiment of the invention, a waste reservoir is provided sealed on all sides except for an inlet from the well array and including an air hole to release air. Optionally, a piece of absorbent paper or other suitable material is provided to wick fluid out of the reservoir.

In an exemplary embodiment of the invention, the capillary channels serve to define a flow rate, so that even if medium is supplied at too high a rate, the actual rate reaching the cells is a known controlled rate.

Before explaining at least one embodiment of the invention in detail, it is to be understood that the invention is not necessarily limited in its application to the details of construction and the arrangement of the components and/or methods set forth in the following description and/or illustrated in the drawings and/or the Examples, if any. The invention is capable of other embodiments or of being practiced or carried out in various ways.

In addition it is noted that while the description focuses on picowell arrays, the manufacturing methods and capillary flow methods and/or other features described herein may be used with a cell holding area of a different type, for example, an adhesive cell holding area. In an exemplary embodiment of the invention, a chemical coating or treatment is provided on the surface of the substrate where the cells are about to sediment, e.g. Avidin-Biotin, poly-L-Lysine or Cell-Tack™ cell adhesion agents.

An embodiment of a device of the present invention, device 10, is depicted disassembled in FIG. 1A.

In an exemplary embodiment of the invention, device 10 consists essentially of five discrete components: a base plate 12, two spacers 14a and 14b, an inlet reservoir component 16 and a cover 18. As shown, the components are provided in three planar layers, a base including picowells, a flow conduit defining layer and a cover. In an exemplary embodiment of the invention, the cover defines capillary flow channels together with the flow conduit layer. Also, while the conduit defining layer is shown to be made of multiple components, in some embodiments, it is provided as a single planar component, for example, a stack of adhesive layers as described below.

In an exemplary embodiment of the invention, when provided as a single layer or as components, parts may be formed, for example, by die cutting, knife cutting, laser cutting, sand cutting and/or other cutting method known in the art. Optionally, a single sheet of material or laminate is cut using a die or laser to define multiple conduits and/or apertures, as needed, and then attached onto a large base or arrangement of base parts (e.g., optionally defining multiple devices in one or two dimensions). Optionally, the large base is cut after assembly into smaller parts as needed. Optionally or alternatively, the layers are scored to make cutting and/or separation of individual components, easier.

Base plate 12 of device 10 is substantially a transparent glass (or plastic) microscope slide (e.g., 0.17 mm-1 mm thick, 2.54 cm wide, 7.62 cm long, though other standard sizes may be supported) on which a circular 1 cm diameter well array 20 for the study of cells has been embossed, for example from a UV-curable adhesive such as NOA-61, NOA-63 or NOA-81 (Norland Products Inc., Cranbury, N.J., USA, USA). Embossing is performed, for example, by applying a drop of the fluid precursor of the adhesive and curing the fluid precursor while in contact with a die (made, for example, from a metal such as Teflon-coated metal, glass, PDMS or silicone rubber) having a negative of the well array. The drop of adhesive disperses between the slide and the die and forms a thin layer (e.g., 10-100 micrometers thick). After the adhesive has set, the die is peeled away or otherwise removed.

Optionally or alternatively to embossing, the glass is etched. In an exemplary embodiment of the invention, a layer (not shown) is provided over the glass, but not over the picowells, or not over the active picowells, to match the height of the wells to the conduits. Optionally or alternatively, the thickness of the conduit layers is selected to have desired properties (e.g., of flow rate and/or cell dislocation), taking into account the thickness of the picowell area. In an exemplary embodiment of the invention, the entire glass slide is etched or embossed with picowells, and these are covered over by adhesive tape or adhesive or another layer, except in area of the active picowells.

In an exemplary embodiment of the invention, the final thickness of the device is selected to be the same as a standard thickness of a glass slide. Optionally, the slide is provided with boundaries on one or more side and the layers and components are placed within such boundaries. Optionally, the slide is pre-manufactured to include a recessed region where the picowells and/or components and/or their cover are placed, so that the slide is surrounded on one or more sides by original slide material. Optionally, such a structure provided a more robust device.

Optionally, additional step(s) are carried out to stabilize the structure and its adhesion to the base and/or to extract and remove non-polymerized residues of the adhesive which may harm cells. These steps optionally include one or both of annealing in mild temperature (~60° C.) for at least one hour and then soaking in 90% ethanol for 5 days. This process is optionally shortened if UV curing is longer and/or leave less monomers. Such soaking may be important to extract toxic un-cured agents from the polymerized adhesive. In a final step the slides are optionally rinsed in distilled water or fresh ethanol to wash away debris and/or residues of foreign materials.

Figure 1B:
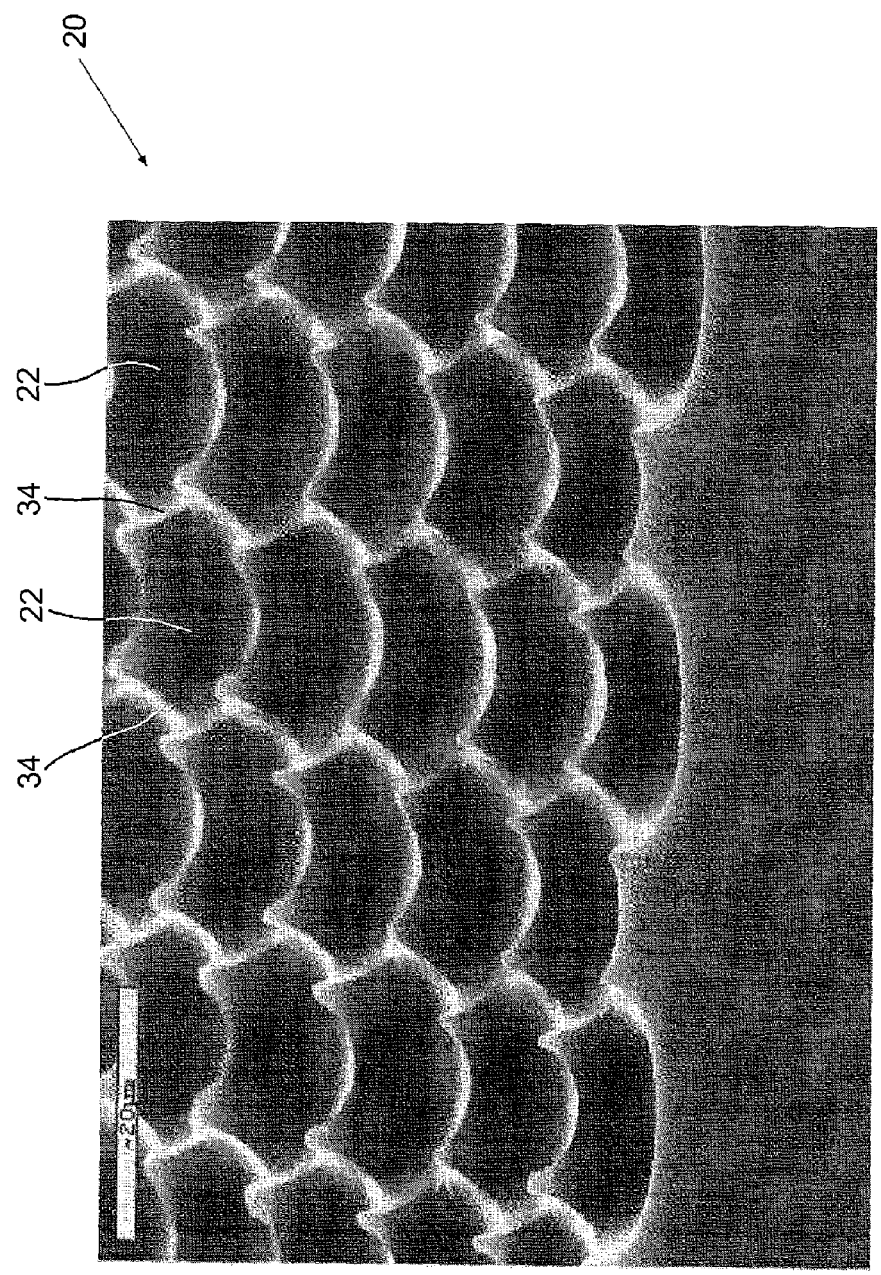
FIG. 1B is a reproduction of a SEM image of a well array of a device for the study of cells, in accordance with an exemplary embodiment of the invention.

FIG. 1B is a reproduction of a photomicrograph of the surface of well-array 20. It is seen that well array 20 is an array 20 micrometer diameter 8 micrometer deep circular wells 22 hexagonally-packed that are juxtaposed so that two adjacent wells 22 are separated by a wall 24 that is less than 1 micrometer wide so that the distance between the two adjacent wells 22 is not more than 110% of the well-dimensions (less than 21 micrometer interwell distance/20 micrometer well width). In an exemplary embodiment of the invention, flat bottomed picowells are manufactured by DRIE (deep reactive ion etching) etching.

Spacer 14 may be made of one contour or created from several parts, such as Spacers 14a and 14b and inlet reservoir component 16. The spacers are optionally about 0.5 mm thick and made of plurality of double-sided adhesive sheets, with or without a strengthening layer in-between. As discussed herein, the spacer height is one of the parameters which can be modified to control the capillary forces and the fluid velocity. An additional such parameter is the materials used for spacer 14 and/or in contact with fluid. As will be discussed below, when device 10 is assembled, spacers 14a and 14b and inlet reservoir component 16 define, at least partially, an inlet reservoir 26, an optional flow regulator 28a, and a waste reservoir 30.

Cover 18 is optionally a thin (0.17 mm) glass cover slip or another transparent material, such as a flexible transparent plastic sheet. Optionally, the cover is preassembled with the device (such as being partly-adhered), prior to provision to an end user and/or prior to use.

Optionally, for assembly, the components are stacked together so that the adhesive of spacers 14a and 14b and inlet reservoir component 16 adheres to base plate 12 and cover 18. Optionally, a separate adhesive layer is provided, for example, being brushed or sprayed on.

Device 10 is depicted assembled in a perspective view in FIG. 2 and in side view in FIG. 3. The assembly of the various components helps define inlet reservoir 26, flow regulator 28a and/or waste reservoir 30.

An exemplary use of device 10 in implementing a method for studying a plurality of cells as individuals is described with reference to FIGS. 4A-4F.

Figure 4A:
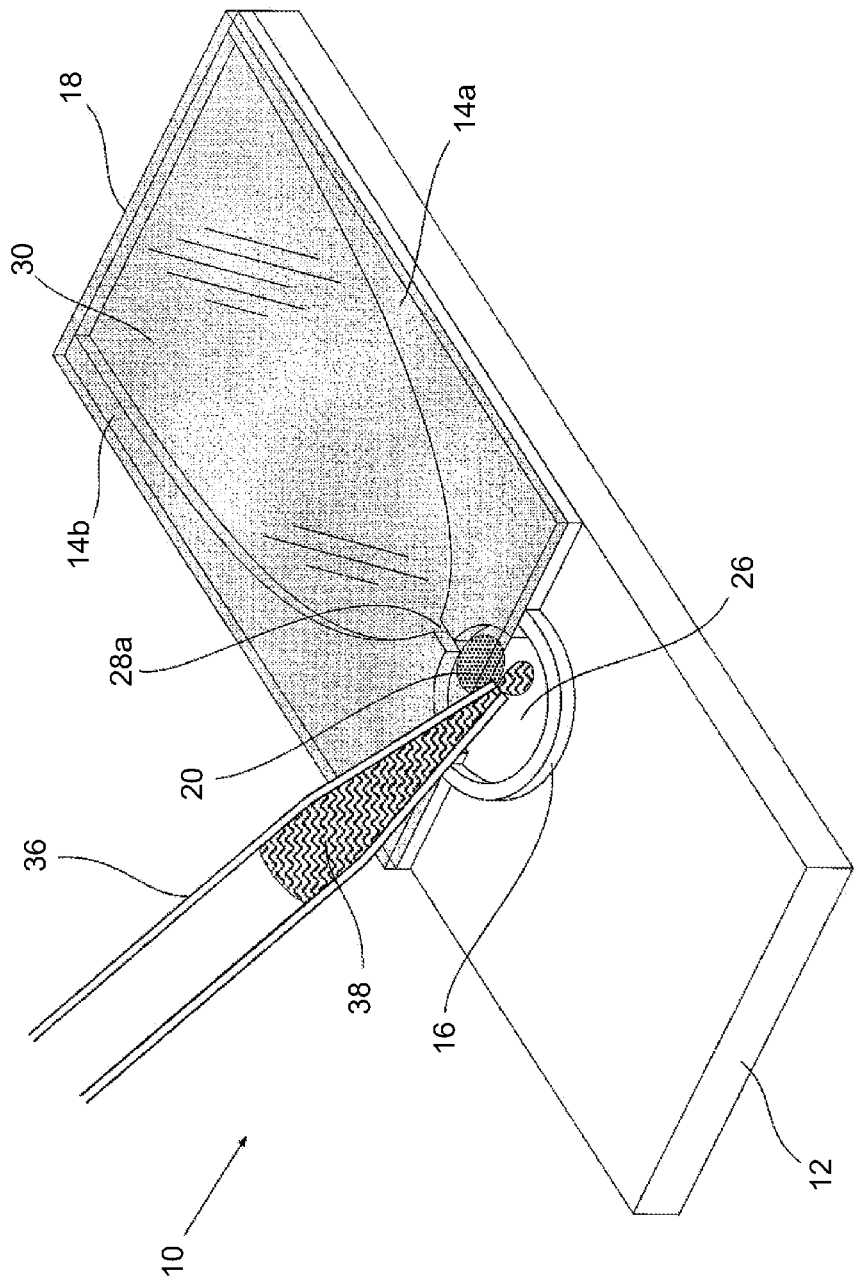
FIGS. 4A-4F depict the use of a device such as depicted in FIGS. 1, 2 and 3 for the study of cells, in accordance with an exemplary embodiment of the invention.

In FIG. 4A, a pipette 36 is used to apply a drop of a first liquid 38 (e.g., a suspension of living cells having a diameter appropriate to picowells size, range e.g. 10 um to 400 um) into inlet reservoir 26 defined by inlet reservoir component 16 and the edge of cover 18. Optionally, the distance between cover 18 and base plate 12 is 0.5 mm as defined by spacers 14a and 14b. Such a distance is sufficient to draw first liquid 38 including cells suspended therein, by capillary action, into proximity of well array 20, through flow regulator 28a and into waste reservoir 30. As the space between base plate 12 and cover 18 is open, air displaced by the introduction of the liquid escapes.

Figure 4B:
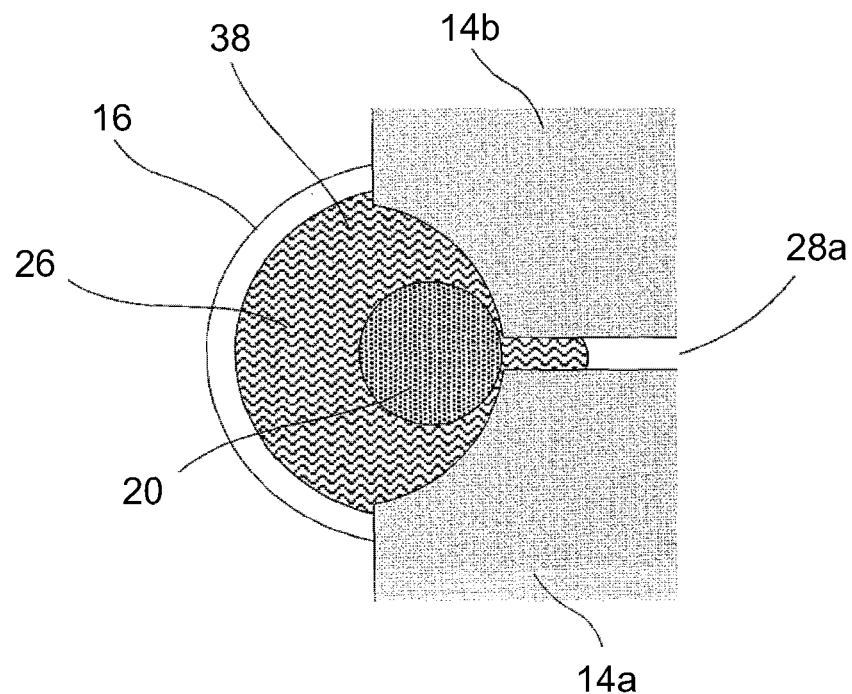
Figure 4C:
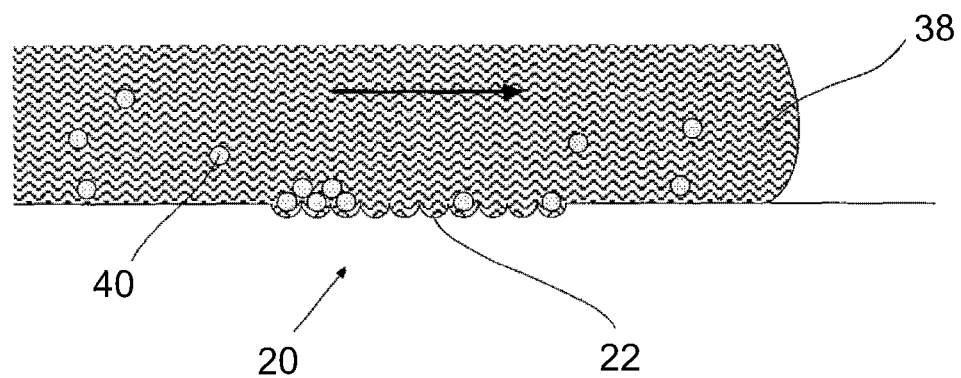

As depicted in FIGS. 4B and 4C, as first liquid 38 passes well array 20, cells 40 settle into individual wells 22. Flow regulator 28a is relatively narrow (2 mm wide) and so acts as a bottleneck, regulating the flow of liquids by slowing the flow of liquid such as first liquid 38 therethrough. The flow-regulating effect substantially ensures that cells 40 have time to settle in wells 22 and are not simply carried away. Cells 40 that do not settle in a well 22 are eventually washed away by the flow of first liquid 38 to waste reservoir 30.

Figure 4D:
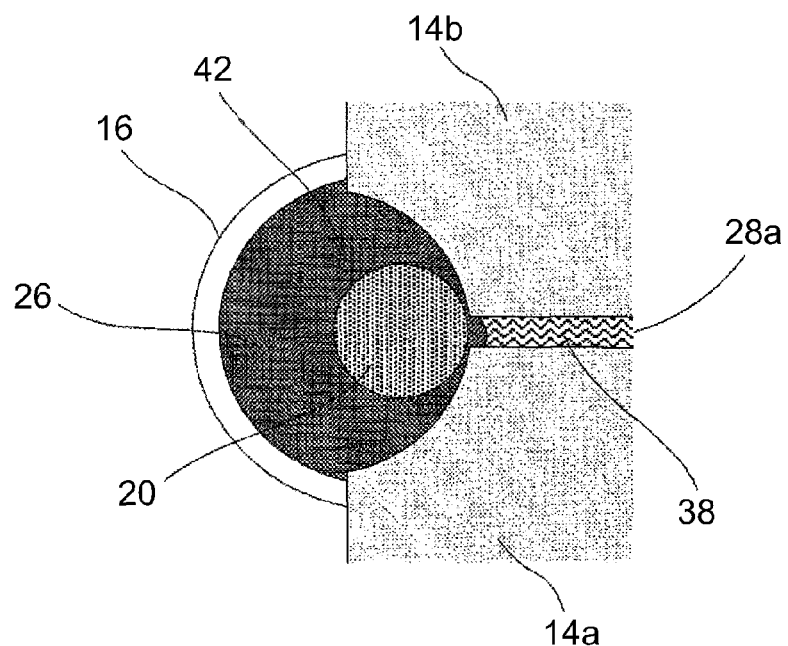
Figure 4E:
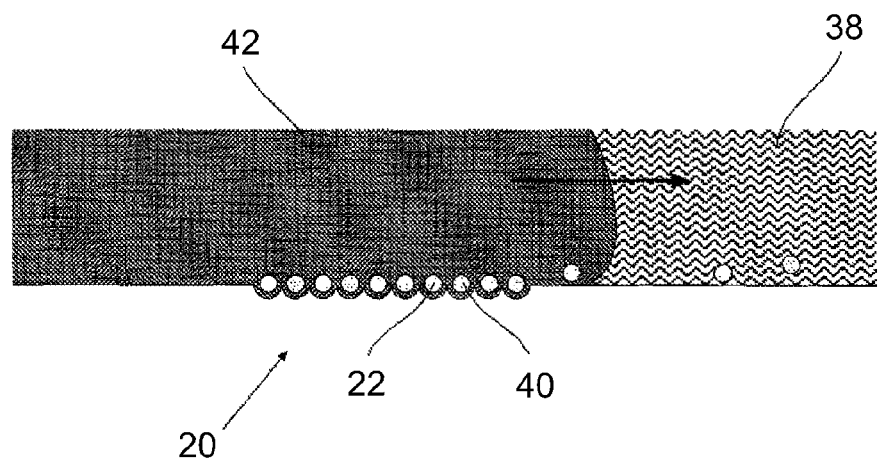

Optionally, after inlet reservoir 26 is empty of first liquid 38 (or while containing some liquid), a second liquid 42 is added to inlet reservoir 26, as depicted in FIGS. 4D and 4E. Second liquid 42 is drawn by capillary action into and past well array 20, through optional flow regulator 28a and into waste reservoir 30, all the while optionally displacing first liquid 38. In an exemplary embodiment of the invention, the flow-regulating effect of flow regulator 28a reduces flow velocity so that cells 40 held in wells 22 are not displaced out of wells 22 and carried away to waste reservoir 30 or move to other wells 22, thereby becoming unidentifiable. In an exemplary embodiment of the invention, the function of flow regulation is carried out by design of a capillary input to the picowells, capillary output form the picowells and/or added baffles in the flow.

Optionally or alternatively, cell dislocation is reduced by controlling a depth of a step from the flow to the picowells, which step may be zero (if wells on same level as inlet flow), negative (if wells above inlet flow) or positive (if wells below inlet flow. Similarly, a step or incline between the picowells and outlet flow into the waste reservoir may be adjusted accordingly. In an exemplary embodiment of the invention, the start of the picowells and/or end of the picowells is spaced from such a step.

In an exemplary embodiment of the invention, such adjustments are made during manufacture and a user selects desired flow properties by selecting a certain slide design.

Figure 4F:
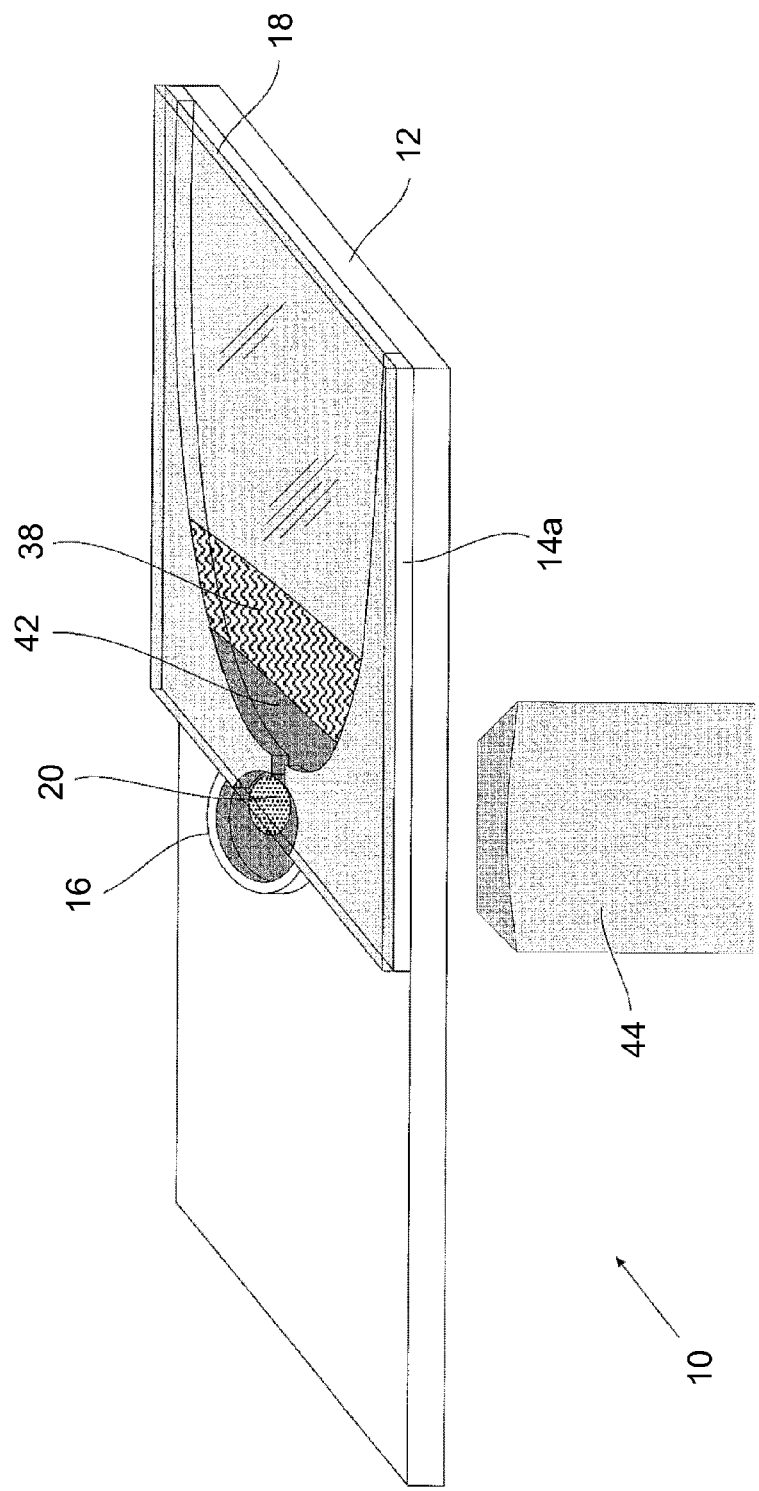

As depicted in FIG. 4F, when desired cells held in well array 20 may be studied, for example by optical observation, with the help of a microscope such as inverted microscope 44. In an exemplary embodiment of the invention, the cells are studies with a non-inverted microscope.

Flow Regulator

In an exemplary embodiment of the invention, a flow regulator, such as flow regulator 28a, is a structure or feature that regulates the flow of liquids such as aqueous liquids past a well array such as well array 20 in order to allow cells to more easily settle in a well array and to prevent cells from being displaced from wells in which held when liquids are added.

In an exemplary embodiment of the invention, flow regulator 28a of device 10 is relatively narrow (2 mm across, 4 mm long) and thereby configured to act as a bottleneck to reduce the rate of flow of liquids across well array 20, so as to assist in filling wells 22 with cells 40 and assisting in retaining cells 40 in wells 22 when liquids are added to inlet reservoir 26.

Other embodiments of devices have other configurations of flow regulator configured to reduce the rate of flow of liquids past a well-array.

In an exemplary embodiment of the invention, the flow regulator operates by controlling the rate of capillary flow therein. Optionally, these considerations also apply to designs where flow into the picowells is also capillary, for example, as in FIG. 6 below. In an exemplary embodiment of the invention, the rate of flow in the inlet capillary is smaller than in the outlet capillary or larger, as a means of affecting flow rate. Optionally, the capillary force applied by the reservoir is also part of the control of capillary flow rate.

In an exemplary embodiment of the invention, the degree of retaining cells in their picowells during fluid manipulations (e.g., applied for staining, treating with drugs and/or washing) is affected by the structure geometry and the capillary flow characteristics, whereas the flow itself is determined by the conduit geometry and surface parameters.

In an exemplary embodiment of the invention, the flow rate through the flow regulator depends on two variables: the capillary cross section and the angle of wetting of the fluid that flows when confronted with the materials of the flow regulator, in addition to fluid properties, such as viscosity, surface energy and/or specific gravity of cells in fluid relative to rest of fluid. In an exemplary embodiment of the invention, the following estimating formula is used:

$$F = H\sigma_{LG1} \cos\theta_1 + 2W\sigma_{LG2} \cos\theta_2 + H\sigma_{LG3} \cos\theta_3$$

Where
H=height (clearance), W=Width. The indexes denote the different surfaces: #1, 2, 3, which refer to top, sides and bottom which may be made of different materials (e.g., or coated with such) hence possessing different surface tensions and contact angle. Optionally, different sides and/or top and/or bottom are coated and/or made of different materials. This may cause the capillary flow to have an asymmetric leading edge, which may affect cell dislocations.
$\sigma_{LG}$=liquid-gas surface tension
$\theta$=contact angle The capillary pressure P is calculated by dividing the force by the applicable area, HW, hence:

$$P = (1/W)\sigma_{LG1} \cos\theta_1 + (2/H)\sigma_{LG2} \cos\theta_2 + (1/W)\sigma_{LG3} \cos\theta_3$$

In one example, if a same conduit was made from two glass surfaces the resulting flow velocity is too high due to the excellent wettability of the glass. If, however, the same flow conduit is made of Teflon, the hydrophobicity of Teflon could result in there being no capillary flow at all.

In an exemplary embodiment of the invention, a user can temporarily modify the flow rate by changing the properties of the injected fluid. In an exemplary embodiment of the invention, some fluids, for example for staining and/or washing may be manipulated to have contact angles and/or viscosities and/or otherwise have a different flow rate that matches the desired flow rates in the device, for example, by adding serum, glycerine or glucose.

In an exemplary embodiment of the invention, the slide to be used is selected base don the properties of the fluid and cells to be used and the desired flow rate.

Figure 5A:
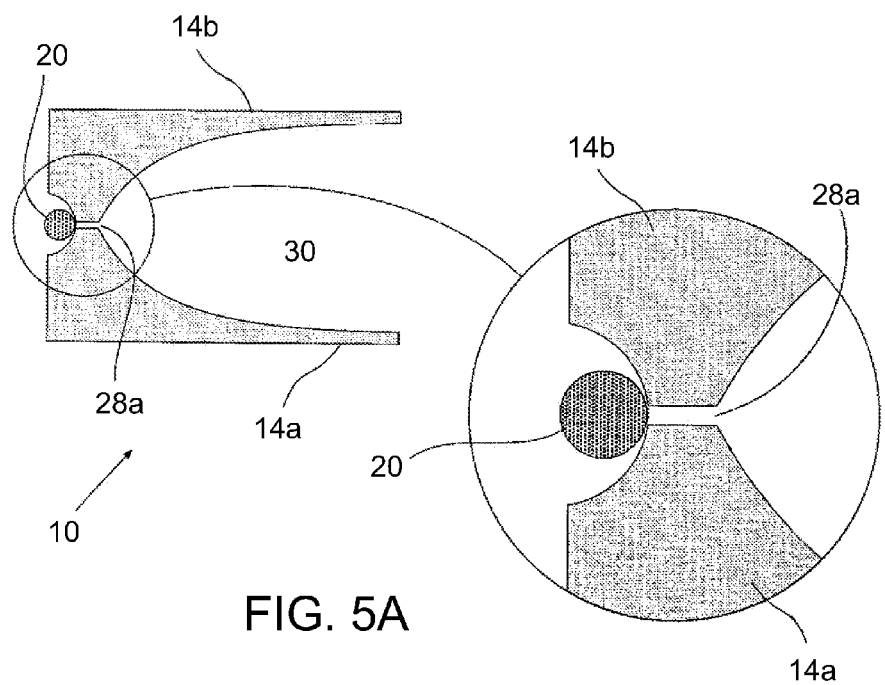
FIGS. 5A-5G schematically depict various devices useful for the study of cells, in accordance with exemplary embodiments of the invention.

In FIG. 5A is depicted device 10 where flow regulator 28a is relatively narrow (e.g., depending on fluid, height and/or desired flow rate), that is 2 mm across.

Figure 5B:
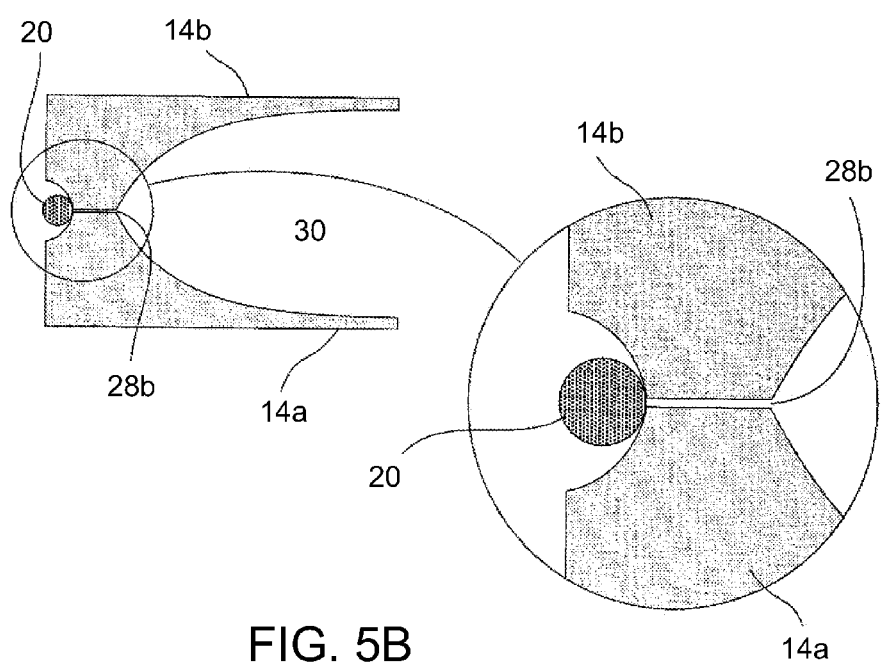

In FIG. 5B is depicted a device where a flow regulator 28b is longer (8 mm) and narrower (0.5 mm) so as to have a greater reduction of flow rate than flow regulator 28a.

Figure 5C:
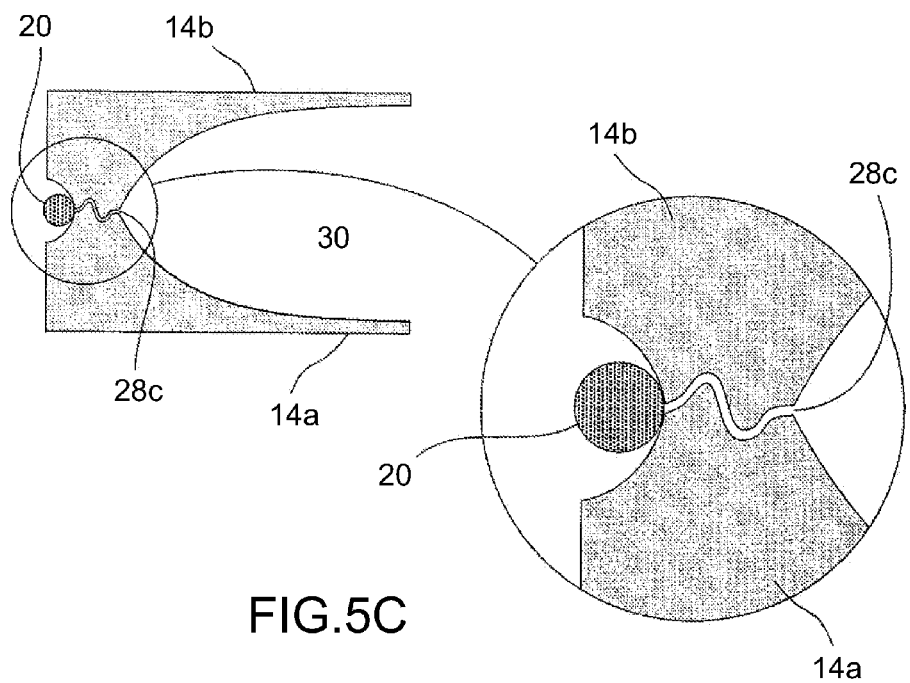

In FIG. 5C is depicted a device where a flow regulator 28c is narrow (0.5 mm) and serpentine (path length of 16 mm) so as to have a greater reduction of flow rate than either flow regulator 28a or 28b.

Figure 5D:
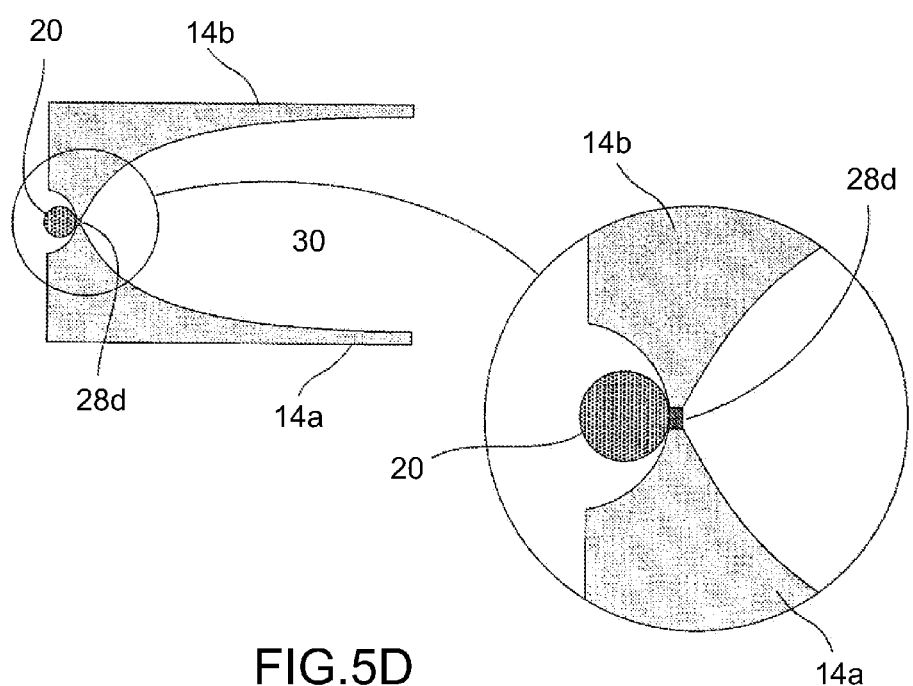

In FIG. 5D is depicted a device where a flow regulator 28d is 2 mm across and 1 mm long, but is coated with a very thin layer of a hydrophobic material. The hydrophobic material reduces the rate of flow of aqueous liquids through flow regulator 28d.

Optionally or alternatively, the regulator is higher than the rest of the flow conduit, thereby narrowing a cross-section of flow. Optionally or alternatively, such added height may keep the main flow higher than the cell layer, possibly reducing cell dislocations. Optionally, cells are placed in locations not expected to be affected by eddies in the flow caused by the change in height. Optionally or alternatively, the cells are close enough so that some flow-induced mixing between the flow and fluids near the cells, is supported.

Optionally or alternatively, a plurality of baffles, for example, obstruction are placed in the flow conduit. Optionally or alternatively, to baffles, other obstacles, such as traverse (to flow) scratches, are provided, which scratches may cause slowing-down eddies and/or reduce capillary force.

Optionally or alternatively, a plurality of flow conduits are provided, for inlet and/or outlet form the picowells. Optionally, a user can select which inlet conduit to use for a given pipettation, for example, based on expected flow rate characteristics of the added fluid in that conduit.

Figure 5E:
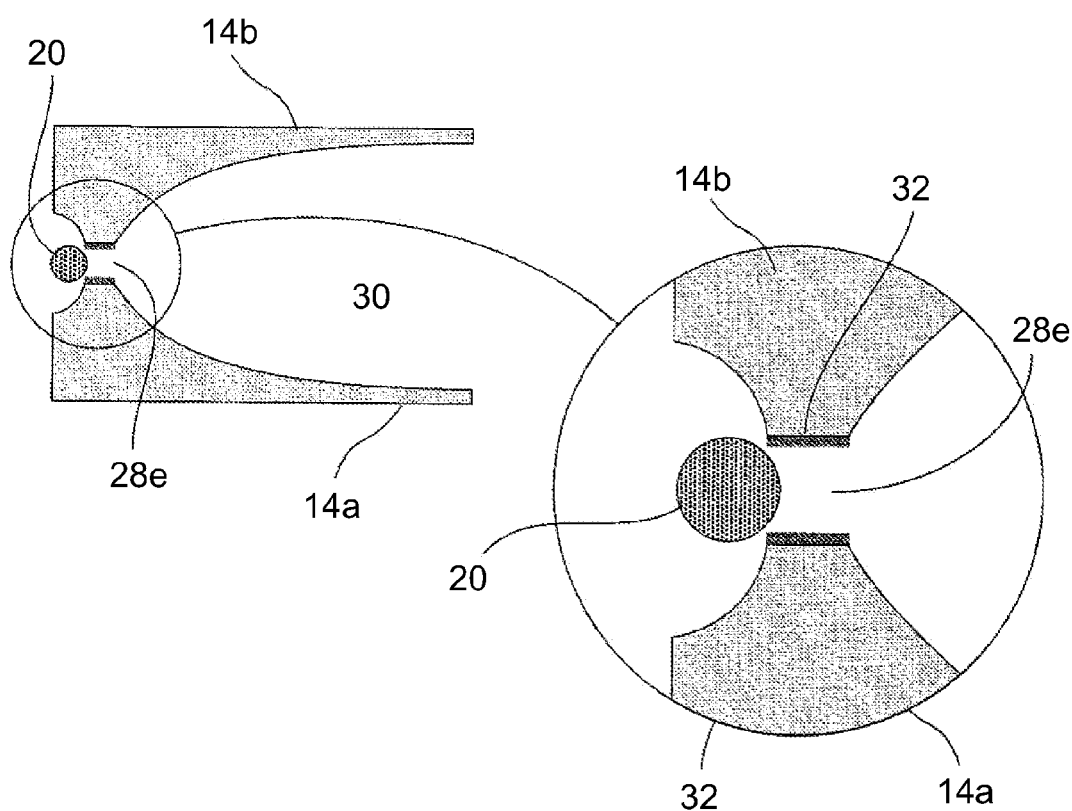

In FIG. 5E is depicted a device where a flow regulator 28e is as wide as well array 20 but includes edges 32 (at the interface between spacers 14a and 14b with base plate 12 coated with a very thin layer of a hydrophobic material. The hydrophobic material reduces the rate of flow of aqueous liquids through flow regulator 28e. At the same time, the width of flow regulator 28e allows a more homogenous unidirectional flow across well array 20, with relatively fewer eddies or stagnation points.

Figure 5F:
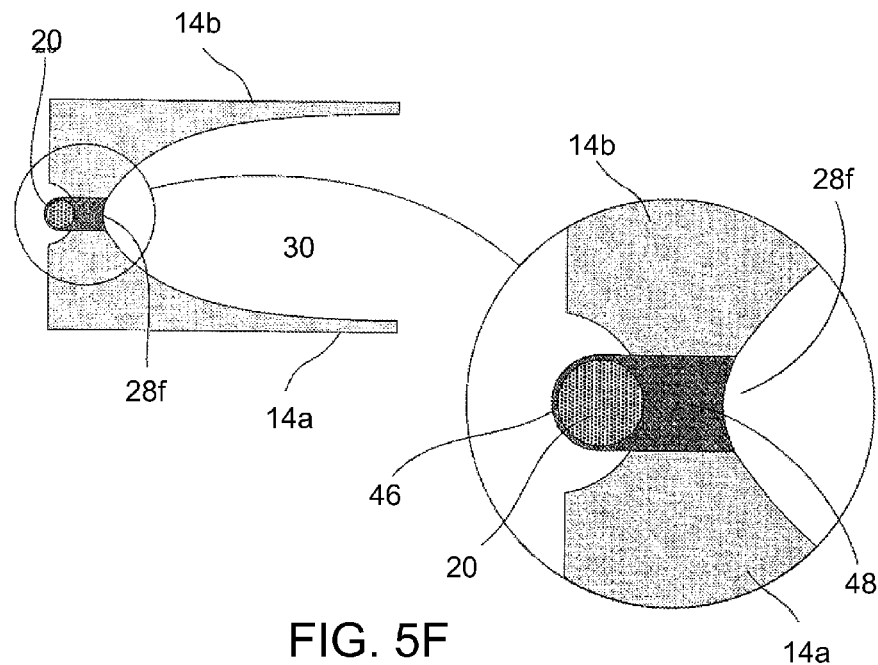

In FIG. 5F is depicted a device where a flow regulator 28f is as wide as well array 20 but the entire width of flow regulator 28f is coated with a very thin layer of hydrophobic material as in FIG. 5D. In FIG. 5F, a relatively large region of base plate 12 is coated with a very thin layer of (relatively) hydrophobic material (e.g., a UV-curable adhesive such as NOA-61 or NOA-81) where an upstream portion 46 is embossed with a well array 20 while a downstream portion 48 is left smooth.

Figure 5G:
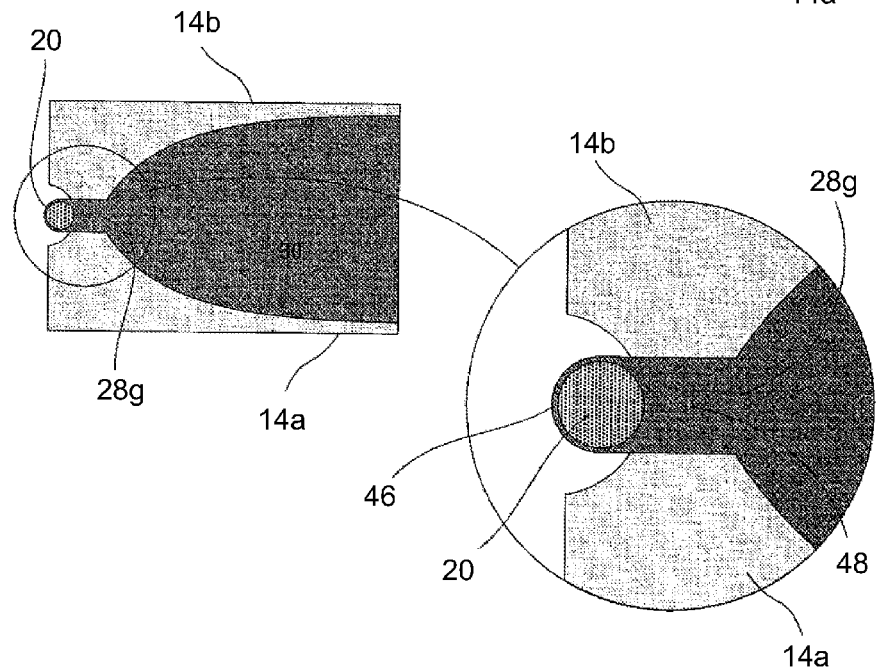

In FIG. 5G is depicted a device related to the device depicted in FIG. 5F. The device is fashioned by placing a thin (20-100 micron) layer of a (relatively) hydrophobic material (e.g., a UV-curable adhesive such as NOA-61 or NOA-81) on substantially the entire surface of a base plate. Then, spacers 14a and 14b as well as inlet reservoir component 16 are placed on top of the layer of hydrophobic material and a die including a negative of a well array is also appropriately placed. When the hydrophobic material is cured, not only is well array 20 produced around the die, but spacers 14a and 14b as well as inlet reservoir component 16 are fixed (by adhesion) to the base plate and all of flow regulator 28g and waste reservoir 30 include a layer of hydrophobic material.

In some embodiments, a combination of two or more of the above elements is provided in one or more flow regulators (e.g., inlet and/or outlet).

Picowell Socket

In some embodiments of the invention, and as noted above, the picowells may be on a level lower than (e.g., be in a socket) or higher than (e.g., be on a pedestal) the flow conduits which lead to and/or from the wells. In some designs, the size and shape of such a difference in level and/or distance of an edge of such pedestal or socket from the picowells can have an effect on one or more of initial cell deposition and cell repositioning during later flow. In many applications it is desirable that the cells settle slowly after an initial application and that the cells not move during later flow. Optionally, the flow parameters discussed above are selected so the initial flow will be fast enough to carry all cells into the picowell area. Optionally or alternatively, it is desired that at least by diffusion later flow will exchange food stuff, stimulants, assay materials and/or waste products with the fluid in the picowells. Optionally or alternatively, it is desired that later flow will wash any cells not in wells away from the wells.

In an exemplary embodiment of the invention, when the picowell is in a socket, a flow conduit is wider (e.g. is 4 mm wide) than the socket (e.g. diameter is 3 mm) and the extra width is selected to have desired flow effects. Other relative widths that may be provided are 0.1 mm wider, 0.5 mm wider, 0.9 mm wider, 1.2 mm wider and 2 mm wider, or intermediate or greater widths. The socket and/or cell arrays may lie symmetrically or asymmetrically in the flow conduit.

As cells typically adhere to the wells with some force, there can be a "sweet spot" within which flow is fast enough but not too fast. In an exemplary embodiment of the invention, one or more of the following are varied and/or taken into account:

(i) socket dimensions;
(ii) socket diameter (if round) vs. conduit width;
(iii) specific gravity of cells with regards to specific gravity of the fluid; and
(iv) picowells depth and wall geometry.

It should be noted that in some embodiments of the invention, the picowells are mounted in the socket using a layer of double sided tape underlying a picowell chip.

Exemplary Design Process

In an exemplary embodiment of the invention, at least some of the above considerations are too complex and/or expensive to calculate or simulate and instead empirical design is used. In some cases, software is used for modeling and/or simulating a whole device or a part thereof, for example, CFD-microfluidics software such as flow-3D by flow science inc, USA.

In an exemplary embodiment of the invention, the following process is carried out:

(a) select some or all of picowells geometry, number of cells to be explored (e.g., giving total number of picowells and cell chamber area) and/or cell sample volume (e.g., giving cell chamber height).

(b) select initial materials/coating. Materials involved in the structure must first be proven as biologically inert (e.g., not to affect the cell's life cycle) and optionally express low fluorescence (so as not to bias fluorescence measurements).

(c) modify sizes, materials and/or fluids to be used (e.g., using search techniques known in the art), until desired results are achieved. In an exemplary embodiment of the invention, such results are published in a book or database (e.g., stored on a computer readable media and/or available by network connection and/or via a computer with a CPU and a memory with instructions for an interface to the database) which can be consulted as needed to select a proper set of slide, cells and fluid properties and/or effects of incorrect fluid properties.

In some cases, a stable performance is not easy to achieve since the device must perform under various fluids types which are common on the biology lab—water, buffers (e.g. PBS), wide range of cell growth media (with and without Serum, etc.), etc.

In an exemplary embodiment of the invention, the design process takes into account other issues as well, for example, void volume and/or eddies caused when adding fluid. Typically, during the operation of the device fluids are added using a pipette. When the new drop of fluid touches the fluid already in the fluid conduit, the fluids suddenly connect and a sudden "violent" fluid movement occurs. If this happen too close to the cells—cells might be shocked and dislodged. If, however the contact point between the fluids is far from the picowells, this can result in a larger dead volume from the pipettation point until a drop of reagent reaches and affect the cells. This can be a problem with respect to one or both of time and final concentration of the reagent reaching the cells. Optionally, multiple pipettation points are provided. Optionally or alternatively, a baffle is provided to absorb such violent movements, for example, in the form of one or more obstructions or transverse scratches in the inlet flow.

In an exemplary embodiment of the invention, when adding fluid, more fluid than fits in the picowell socket is provided, for example, 8-9-10 microliter for a 7 microliter socket. This can ensure overflow and/or avoid voids. In an exemplary embodiment of the invention, for example as shown in FIG. 6, overflow material which cannot flow fast enough into the device can flow back via a channel that reaches away form the picowells and pipettation location and towards an edge of the device, where it may be stored in a reservoir or drip out.

Base Plate

When a base plate is present, any suitable material or method may be used, optionally contingent on the above considerations.

In some embodiments, a base plate such as base plate 12 is an optically transparent material to allow observation of cells held in the wells. By transparent is especially meant transparent to one or more frequencies of electromagnetic radiation in the visible, ultraviolet or infrared spectra.

Suitable materials from which a base plate is made include glasses (e.g., sodalime glass and borosilicate glass, especially optical grade glass) and plastic materials (e.g., polyethylene terephthalate, polycarbonate, polyester, polystyrene).

In some embodiments of the invention, the substrate is solid and flat. In others, a hole may be formed therein (socket) for placing a picowell or other cell holding chip or section.

In some non-depicted embodiments, a base plate such as base plate 12 is thinner, for example is a 0.17 mm thick glass cover slip, allowing higher resolution observation, because lens can be closer to the cells. Optionally, the cells are in a socket which is depressed and therefore thinner than the base plate.

Spacers and Inlet Reservoir Components

In exemplary embodiments of the invention, spacers and inlet reservoir components allow liquids to pass through device 10 by capillary action. In some embodiments, the thickness of the components is between 0.1 and 1 mm. An inlet reservoir component such as 16 is the same height, thicker or thinner than corresponding spacers such as 14a and 14b, depending on the embodiment. Spacers and inlet reservoir components may be fashioned according to any suitable method with which one skilled in the art is familiar. For example, in some embodiments, spacers and/or inlet reservoir components are discrete components secured (for example by adhesion) to a base plate (as depicted for device 10). In some embodiments, spacers and/or inlet components are molded (e.g., integrally formed with a corresponding base plate) or embossed in a layer of material, for example, from a UV curable adhesive (e.g., NOA-61 or NOA-81) in a manner similar to the manner in which well-array 20 is fashioned as described above.

In some embodiments, the opening of inlet reservoir which is open to the environment is at least partially covered, for example so as to be exposed only through a narrow slit or hole to reduce evaporation. In some embodiments, the opening (e.g., narrow slit or hole) is such to allow introduction of liquids (e.g., is of a size allowing entry of a pipette tip).

Cover Slip

In some embodiments, a cover such as cover 18 functions as a part of the inlet reservoir, flow regulator and waste reservoir of a device, helping to define these components as capillary channels, allowing the device to function without the need for external flow generators such as pumps or syringes. In some embodiments, a cover is transparent, allowing observation of cells held in a well array therethrough and/or allowing the passage of light therethrough to illuminate the well array. Although cover 18 discussed above is of glass, other suitable materials may be used. In some embodiments, plastics or polymers (e.g., polycarbonate) are used and are optionally processed to desired shapes and/or contours.

Exemplary Well-Arrays

Exemplary well-arrays such as well-array 20 are generally as described in the PCT patent application of the Inventor referenced above. In some embodiments the array of wells is disposed on a surface and comprises a plurality of wells having a dimension on the surface of no more than about 500 micrometers, no more than about 400 micrometers and even no more than about 200 micrometers, the wells of a size and shape suitable for retaining at least one cell therein.

Well-arrays may be fashioned using any suitable method from any suitable material, for example as described above or in any of the referenced PCT patent applications of the Inventor.

In some embodiments, the wells of a well-bearing component are round or hexagonal, although in some embodiments, wells are triangular, square, pentagonal or any other suitable shape. Although wells of a well array of a well-bearing component may be arranged in any suitable arrangement, in some embodiments wells are hexagonally packed, allowing a high loading of cells per unit area.

In some embodiments, two adjacent wells of a well-bearing component are juxtaposed and separated by a well-wall, for example as disclosed in the cited PCT patent applications of the Inventor. In some embodiments, the distance between two adjacent wells is not more than 150%, not more than 130%, not more than 120%, not more than 110% and even not more than 105% of the well-dimension.

The wells of a well-bearing component are optimally of any size so as to hold at least one cell or cell spheroid of a certain type. In some embodiments that are directed to the study of cells as individuals, it is generally preferred that the wells be small so as to avoid having a large number of cells held in any one well.

For example, in some embodiments, a cell well-bearing component is configured for study of lymphocytes having a typically diameter of about 6 micrometers. In some such embodiments a well-bearing component has wells of about 6 to 10 micrometer dimension on the surface of the well-bearing component so that the lymphocytes enter and are held in the wells, one in each well.

For example, in some embodiments, a cell well-bearing component is configured for study of oocytes or single-cell spheroids having a typically diameter of about 400 micrometers. In some such embodiments a well-bearing component has wells of about 400 to 500 micrometers dimension on the surface of the well-bearing component so that the oocytes or spheroids enter or grow/assemble and are held in the wells, one in each well.

Typically, the dimensions of the wells are generally less than about 500, 400, 200, 100, 50, 25 or even less than about 10 micrometers. By dimensions is meant the usual meaning of the word and is dependent on the shape of the wells. For example, for hexagonal or circular wells, the term dimension refers to diameter. For square or triangular wells is meant the longest dimension of the square or triangle, respectively. The exact size of wells of any given well-bearing component is determined by the type of cells or alternately or additionally by the amount of cells to be studied using the carrier. Since different types of cells have different sizes, generally a carrier of the present invention will have wells of a size to accommodate one or more cells of the type to be studied. Most preferred is that a well be of a size so as to hold no more than one cell of the type to be studied at any one time. In other embodiments, a well size is determined by the size of a predetermined number of a certain type of cells, so as to allow holding of that predetermined number of that type of cell, for example two cells, three cells, or even four cells.

To ensure that no more than a limited number of cells are held in a given picowell, and that a held cell is able to efficiently absorb nutrients and release waste, the depth of a picowell is optionally not more than the order of the size of the cell (or cell spheroid) which the well is configured to hold.

In some embodiments, the wells have a depth no more than about 150%, no more than about 120% and even no more than about 100% of the dimension of the well on the surface. According to some embodiments, the depth of the wells is less than the dimension of the well on the surface. In some embodiments, the depth of a well is no more than about 500, not more than about 200, not more than about 100, not more than about 50, not more than about 30, not more than about 20 and even not more than about 10 micrometers deep.

In some embodiments of the present invention, wells are dimples, depressions, or pits on the surface of well-bearing component. In other embodiments, the wells are substantially enclosures of dimensions such that substantially an entire cell of a certain type is containable within the enclosure, each enclosure having an opening at the surface, the opening defined by a first cross section of a size allowing passage of a cell of the certain type.

In some embodiments, in or near a well array of smaller wells is located a significantly larger well, serving as a collection enclosure. Selected cells held in a specific well of the well array are moved, for example with the help of laser tweezers or the like, to a collection enclosure.

In some embodiments, a single device includes wells of different sizes, interspersed or in distinct regions whether in a single well array or on two or more well arrays. For example, in some embodiments one device includes wells having 2, 3, 4 or even more distinct sizes. For example, in an embodiment, a single device includes wells having a diameter of 15 micrometers, 20 micrometers, 100 micrometers as well as 250 micrometers. In some embodiments, such a combination allows the user to study individual cells as wells as clusters of cells on a single device. In some embodiments, such a combination allows the user to purchase a device configured to study cells of different sizes and the user studies a region having a well array including wells configured to hold cells having the size of the cells of interest. Optionally, the sizes and/or distance or other geometry of the picowells define areas where cells will be located as individuals and where cells may conglomerate, multiply and/or communicate with nearby picowells.

Assembly and Packaging

In an exemplary embodiment of the invention, assembly and/or packaging is under vacuum, this can prevent and/or reduce formation of air bubbles during storage and/or use. Optionally or alternatively, the surfaces to be adhered are optionally sprayed with distilled water.

Such gas bubbles may be formed by gasses dissolved in the raw materials. Optionally, the above described annealing and/or washing are under vacuum, to remove gasses.

Exemplary Alternative Slide Design

Various devices useful for microscopy can be built based on an embossed microscope slide, for example a slide 0.17-1 mm thick. The glass is then covered with a spacing layer which has a hole just above the embossed area. The diameter of the hole may be smaller than the embossed area. This structure creates an open chamber, which can be useful for accommodating a cell suspension. This structure may be covered by a cover slip and cells can be observed by an upright and/or inverted microscope.

In another example, a slide structure supports one or more of exchanging cells media, staining, and/or other manipulations of the cells within their picowells. In such an embodiment, an additional "flow" layer is cured to form a flow channel above the cells chamber and a reservoir. This flow layer is sticky on both surfaces, and can optionally be bonded to the spacer layer beneath it, and to the cover layer above. Optionally, a flexible transparent cover, such as made of polycarbonate film, is bonded only on the distal edge of the flow channel. Optionally, a pinhole (or larger hole) is provided, for example, to drain air when liquids are added during the work with the device. A non-sticky removable liner is optionally provided keeps the cover from bonding to the rest of the flow channel. In an exemplary embodiment of the invention, the channels are bordered on either side, rather than open.

Figure 6A:
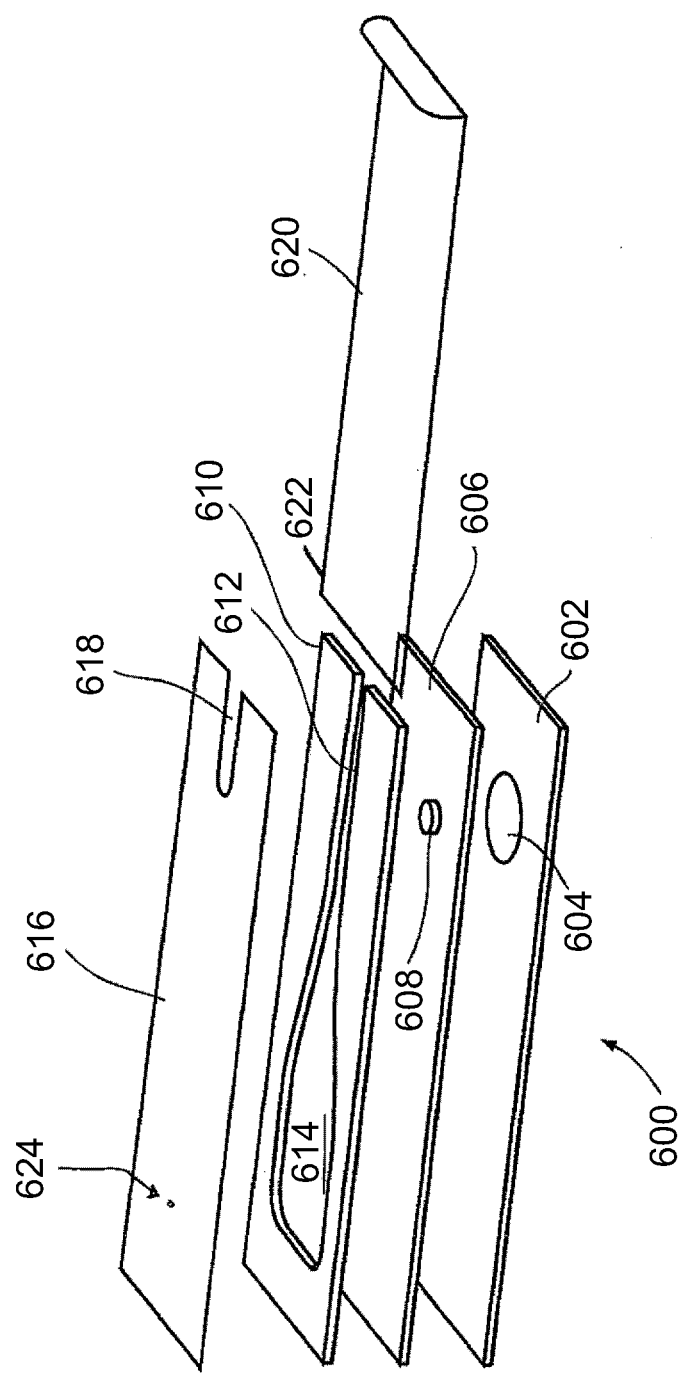
FIGS. 6A and 6B illustrate an alternative cell study device, in accordance with an exemplary embodiment of the invention.
Figure 6B:
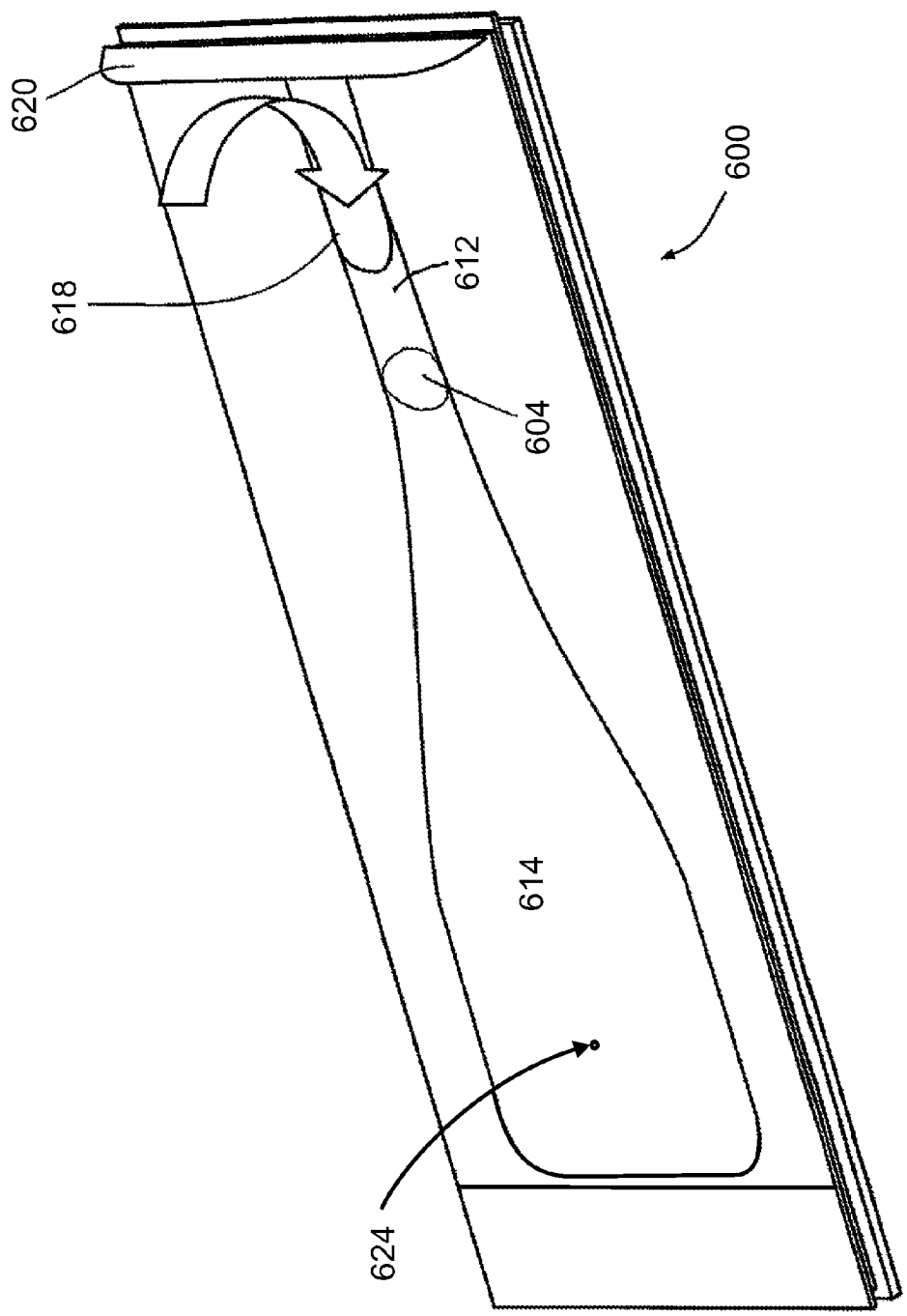

An exemplary such device 600 is shown in FIGS. 6A and 6B, with FIG. 6A being a blow-apart view. A glass slide 602 has embossed (or otherwise attached) thereon a picowell array 604. A spacer layer 606 with an aperture 608 is attached above, for example, layer 606 being a two sided adhesive layer. A flow layer 610 including a flow channel 612 and a reservoir 614 is provided above, optionally as a two sided adhesive layer. A cover layer 616 with an optional air hole 624 and slot 618 are provided above. Optionally, a non-adhesive layer 620 is provided between layers 616 and 610 and includes a tip 622 which is temporarily attached to layer 610.

Optionally, as shown in FIG. 6B, the length of layer 620 is shorter than layers 616 and 610, so layers 616 and 610 can be adhered to each other at their tip.

Other structures may also be built up by layering shaped layers of double-sided adhesive, on microscope slides and/or other bases.

In use, flexible covers 620 and 616 are pulled back and expose the chamber formed by aperture 618 and wells area 604. Cells are loaded into the chamber and removeable liner layer 620 is peeled off. Flexible cover 616 is released and bonds to the rest of upper surface of flow layer 616. Layer 610 optionally defines a capillary channel between layers 616 and 606. Aliquots of fluid can be presented to the capillary slit 618 created between the cover and the opening of the flow channel. Capillary force pulls the fluid into the channel, the fluid replaces and/or flows over the cell media, and the excessive fluid is gradually accumulated in the reservoir 614. Additional fluid can be presented to the flow channel, basically until the reservoir is full. Optionally, fluid can be removed from reservoir 614

Double sided adhesive tapes, optionally medical grade, or other adhesive agents, may be used to bond the layers and/or to form the layers.

If double sided tapes are used, the layers are optionally bonded while wet. This can eliminate air and prevent such air from being trapping between the layers, possibly minimizing the appearance of air bubbles in the suspension along incubation time. Optionally, the devices are manufactured and/or packed under vacuum, to prevent repeated air penetration between the layers before the device is used.

FIGS. 6C-6H are engineering drawings showing exemplary sizes of features of device 600.

Figure 6C:
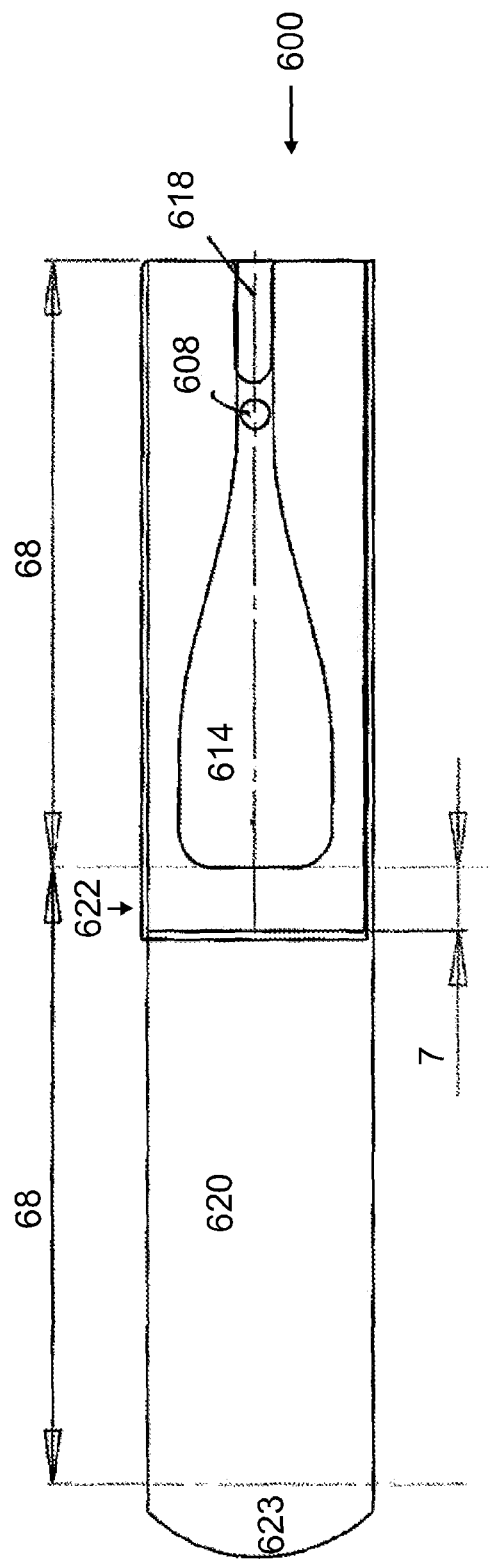
FIGS. 6C-6H illustrate exemplary sizes for parts of the device of FIGS. 6A-6B.

FIG. 6C is a top view of device 600, showing layer 620 folded back over the other layers.

Figure 6D:
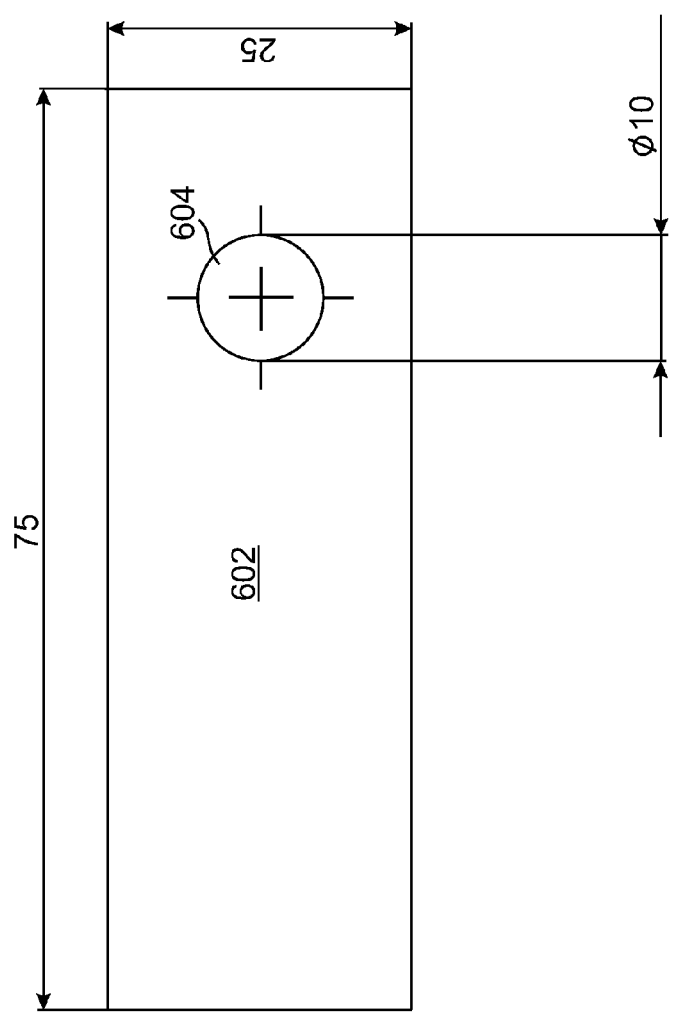

FIG. 6D is a top view of a slide layer 602, optionally formed of glass, including active picowell area 604 which may have picowells engraved, embossed and/or adhered thereto.

Exemplary materials for spacers (e.g., between layers of double sided tape) include:
By Rogers corp. CT, USA: Silicon rubber or polyurethane rubber, e.g. MC-300, MC-600, MS-6000, MS-SOFT, HT-200, HT-1200, HT-1500, HT-6135, HT-6200, HT-6360 series, MS series
By Du-Pont-Kapton®, Mylar®, Neoprene.
By Silex, Hampshire, UK: Silicon rubber sheeting grades GP40, 50, 60 & 70
By Kleerdex LLC (PA, USA): Kydex®
By GE plastics (see below): Lexan Exemplary materials for double sided tapes include:
By 3M, MA, USA: adhesive tapes #1504, 1509, 1510, 1513, 1517, 1522, 1524, 1524A, 1577, 1772, 1773, 1774, 9500, 9731, 9776, 9874, 9877, 9887, 9889, 9917, 9960, 9971

Exemplary materials for the cover include:
By General Electric plastics (MA, USA): Lexan (8010, 8020, 8030, 8040, 8A13, 8A23, 8A35, 8A37, 8B25, 8B26, 8B35, 8B36, FR25, FR60, FR63, FR65, FR66, FR700, FR83),
By SKC inc, GA, USA: Skyrol (SH71, SH81, SH82) and other Polyester (PET, PET-G etc.) films.

In an exemplary embodiment of the invention, the combination actually used depends on desired flow rates and actual geometries. Optionally, a set of materials and geometries is chosen to have a set of properties suitable/acceptable for a plurality of situations, even if not optimal for all.

Figure 6E:
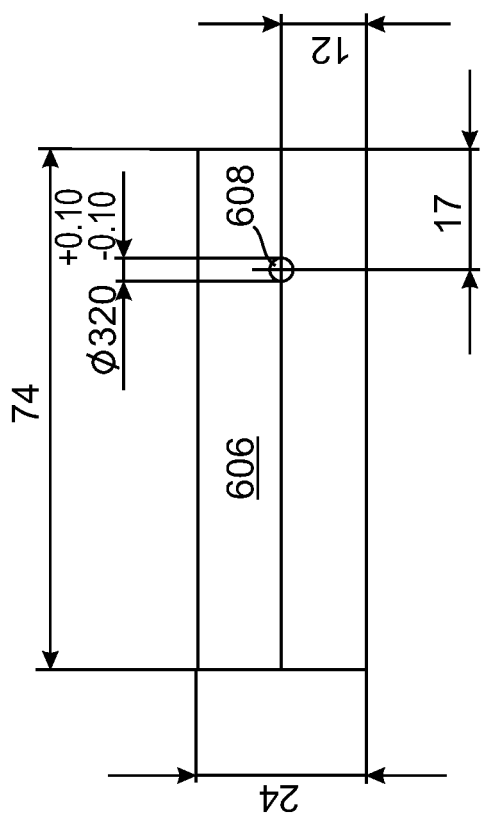

FIG. 6E is a top view of a base layer 606 including an aperture 608 which optionally expose sonly some picowells to the rest of the device and/or which serves to attach a picowell chip in place. Layer 606 is optionally formed of spacer material with double sided tape laminated thereon, above. In an exemplary embodiment of the invention, layer 606 has a thickness of between 0.2 mm and 2 m, for example, 1 mm.

Figure 6F:
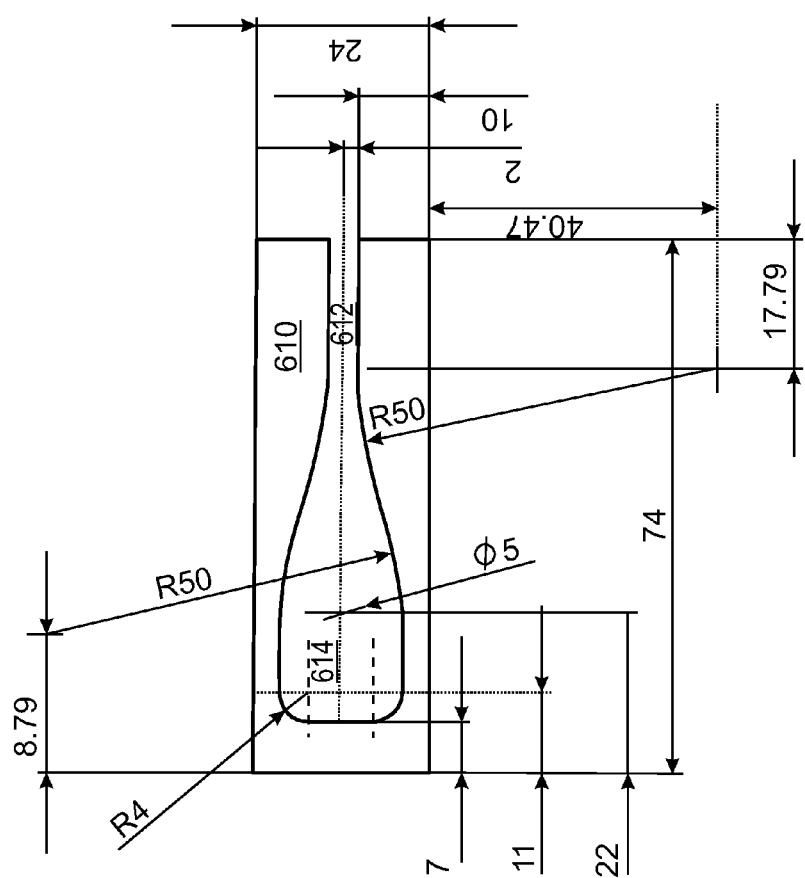

FIG. 6F shows a conduit layer 610, with exemplary dimensions for reservoir (e.g., 300 micro liters) and inlet conduit. Optionally, this layer is formed of a sandwich (e.g., by laminating) of double sided tape, 175 micron thick spacer and a third layer of 1522 above. Optionally, trapped air is avoided using a distilled water spray and all residues are removed.

Figure 6G:
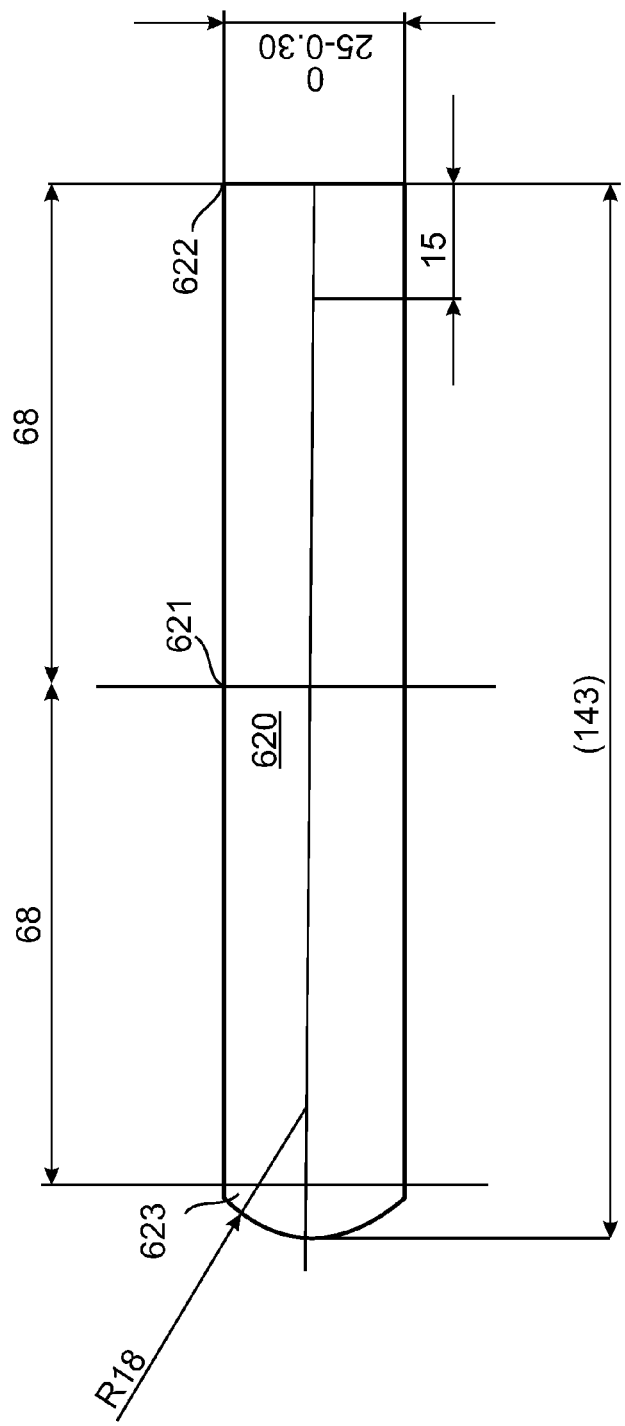

FIG. 6G shows a temporary sticking avoiding layer 620, with a handle 623 and a fold point 621. Optionally, this allows the layer to be folded over, adhered to underlying layers only at a side far from where a cover layer is attached and then easily removed. Optionally, the layer is made of HDPE coated with silicone at points where it is not to stick to 1522 layer below.

Figure 6H:
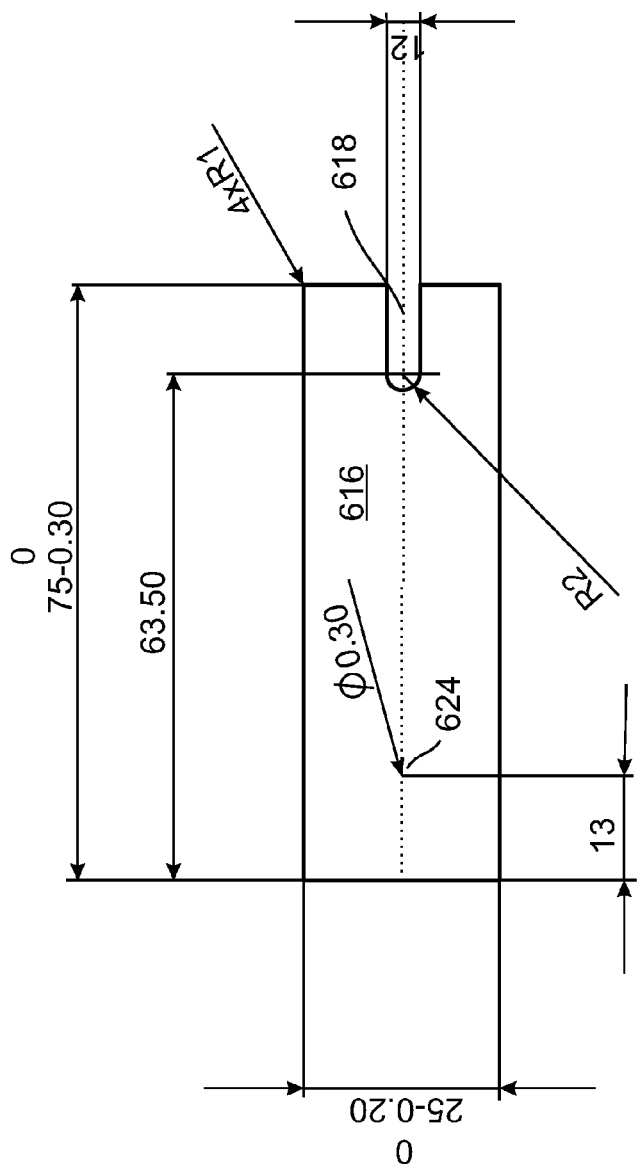

FIG. 6H shows a cover layer 616, with air hole 624. This layer is optionally formed of 0.175 mm thickness.

In an exemplary embodiment of the invention, device 600 is configured so that an initial flow (first 10 micro liters) is about 48 seconds for cell growth media (RPMI 1640). And 30 seconds for Buffer (PBS).

In an exemplary embodiment of the invention, the average flow rate of the succeeding aliquots is about 0.5 μl/sec in media and about 0.75 ul/sec in PBS. In an experiment using molt4 cells (e.g., which appear to be more prone to dislodging), this resulted in total cell movement (after repeating adding 6 aliquots of 10 ul) of up to 10% in RPMI cell media and up to 2% PBS buffer.

In an exemplary embodiment of the invention, device 600 has an active area and working volume of 3.2 sq. mm. (Approximately 18,000 wells of 20 microns), containing 7.5 micro liters of cells suspension. The length width and/or thickness are of a standard microscope slide. Optionally, the total device volume is 300 micro liters. Optionally, there are no moving parts in use and the device is in one piece when unpackaged, possibly simplifying packaging.

Figure 7:
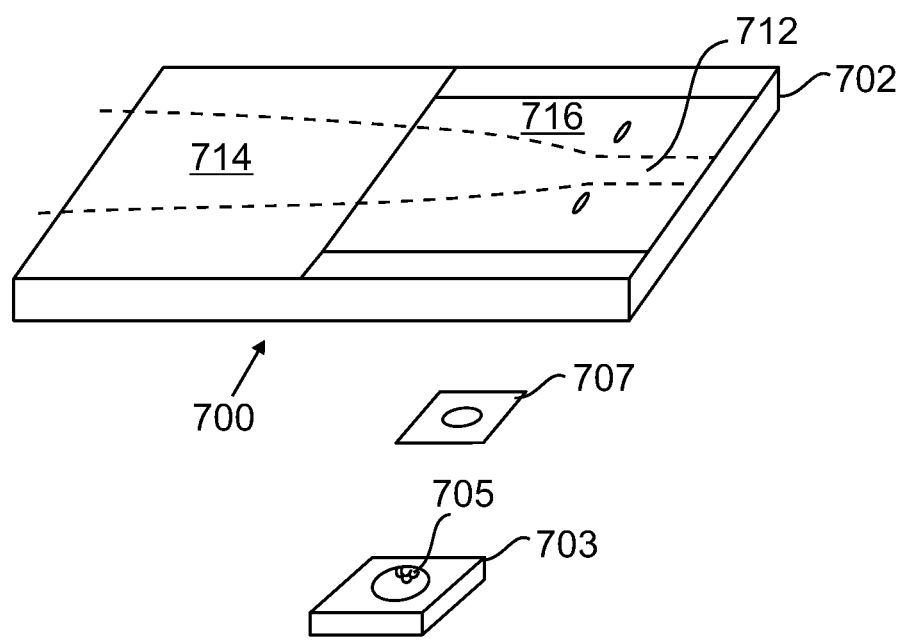
FIG. 7 illustrates an alternative design of a device for studying cells, in accordance with an exemplary embodiment of the invention.

FIG. 7 illustrates an alternative slide design 700, in which a chip or other element 703 with a picowell area 705 formed thereon (part or all) is mounted on a base layer 702. In an exemplary embodiment of the invention, a layer of double sided tape 707 having an aperture formed therein acts as a mask to expose only some of the picowells to the rest of the device and/or to attach chip 703 to layer 702. Optionally, as shown a cover 716, reservoir 7614 and capillary conduit 712 are provided as above.

Exemplary Usage Process

Figure 8:
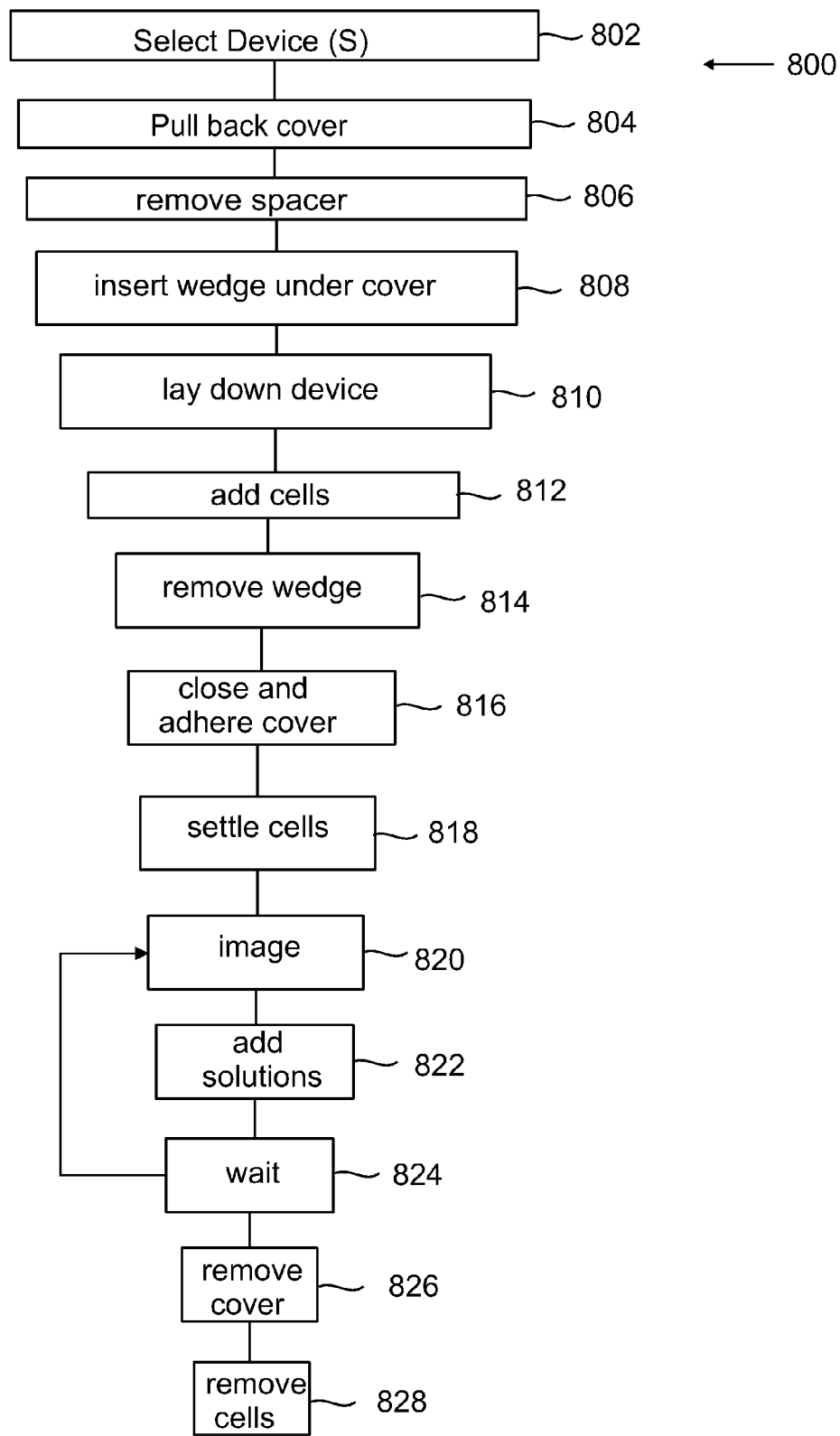
FIG. 8 is a flowchart of a method of using the device of FIGS. 6A-6H, in accordance with an exemplary embodiment of the invention.

FIG. 8 is a flowchart of a method of using device 600, in accordance with an exemplary embodiment of the invention.

At 802 a device is selected form a set of devices, according to desired cell holding characteristics and/or flow characteristics, taking in to account, for example, cell size, cell adhesion, fluids used and/or fluid contact angle with materials in device/

At 804, cover 616 is pulled back.

At 806, spacer layer 620 is removed. As noted above, spacer 1620 may folded and at the side opposite of where cover 616 is adhered to device 600, include a handle 623 and a portion adhered to layer 610.

At 808, cover 616 is prevented from falling down on layer 610, by inserting a wedge at the point where the previously adhered section of layer 616 meets the previously unadhered portion thereof. Optionally, the wedge is a small cylinder having a length of the slide width and a diameter of 2 mm to 5 mm, optionally made of a material, e.g., Teflon or a silicone which is not prone to adhere to the adhesive layer. Other means of preventing the fall of cover 616 can be used as well.

At 810, the device can be laid down on a flat surface, leaving both hands free.

At 812, cells are added to the exposed aperture 1608, optionally with no capillary movement. This may also preload the device, cell area and/or flow inlets with fluid.

At 814, the wedge is removed.

At 816, cover 616 is adhered to layer 610, optionally with care that no air bubbles are formed, optionally, with wetting of cover 616 beforehand. Optionally, this is carried out by one or more of manual pressure or a roller or a hand held stamp.

At 818, or before cover closure, the cells are allowed to settle in wells.

At 820, the cells are imaged and/or otherwise tested. Optionally, such imaging includes adding various reagents and/or stimulants, into slot 618 (822). In some cases, some time is waited so such added fluids have a desired effect (824). Acts 820-824 may be repeated several times and/or for a period of time, for example, minutes, hours, days or weeks.

Optionally, at 826, the cover is removed, so the cells can be retrieved and further tested/processed (828). In an exemplary embodiment of the invention, cover 616 includes a tear line above conduit 612, which is torn manually. Optionally or alternatively, a knife is used to cut cover 616. Optionally, a jig is provided which positions a cutting edge relative to a standard microscope slide, for such cutting. Optionally or alternatively, the adhesive layer of the top conduit is made of a non-permanent adhesive, which can be separated and reattached.

Embossing

In an exemplary embodiment of the invention, a cell holder is formed by embossing. In an exemplary embodiment of the invention, a base is covered with an optionally liquid substrate, contacted with a die and the substrate is at least partially hardened. Optionally, the die defines a plurality of pico liter wells in the substrate. Optionally, the substrate is adhesive to the base, but not to the die, optionally in spite of the substrate being smooth and the die having small features. Optionally, the die and adhesive and base materials are selected to afford such differential adhesion. Optionally, the die is removed before the substrate hardens.

In an exemplary embodiment of the invention, at least two areas on the substrate are patterned, each with a different final pattern of cell holding regions.

In an exemplary embodiment of the invention, one or more walls or barriers are added to the cell holder before, during or after embossing.

In an exemplary embodiment of the invention, the base is not mechanically prepared for the substrate.

In an exemplary embodiment of the invention, there is provided a holder device having at least one cavity for receiving a sample of cells in a medium, wherein the at least one cavity includes a substrate having refractive index substantially equal to that of water, includes a multiplicity of pico liter wells (also called "picowells", herein) formed therein and has a generally inert wall.

In an exemplary embodiment of the invention, there is provided a method of making a holding device having a substrate characterized by an index of refraction essentially equal to that of water, which is adhered to a carrier plate, wherein the substrate is formed into a multiplicity of pico liter wells.

In an exemplary embodiment of the invention, there is provided a method of making a holding device having at least one cavity for receiving a medium, wherein the at least one cavity has a multiplicity of pico liter wells formed in a substrate having a refractive index substantially equal to the medium in which the cells are carried.

In an exemplary embodiment of the invention, there is provided a method of making a die for forming an array of picowell arrays. Optionally, the die is assembled from individual well forming die elements. Optionally, a handle with a plurality of clamps to hold the die elements is used. In other embodiments, other means to hold die elements together into a template are used. Optionally, the die also serves as a template for non-well embossed elements.

In an exemplary embodiment of the invention, there are provided cell holding devices including a plurality of picowell arrays, on each one, optionally in the form of a macroscopic array of picowell arrays. Optionally, the picowell arrays are separated by barriers which may have selected blocking ability, for example, being fluid blocking or cell blocking or fluid passing.

A holding device for studying cells in a medium in accordance with an exemplary embodiment of this invention comprises at least one cavity defined by generally inert wall surrounding a substrate. The substrate has a surface in which a plurality of pico liter wells is formed. The substrate is translucent and has a refractive index substantially equal to the refractive index of the medium.

An exemplary holding device for studying cells in accordance with an exemplary embodiment of this invention comprises a substantially transparent substrate having a refractive index of 1.33. The substrate has a multiplicity of pico liter wells formed in an upper surface and a wall structure attached thereto.

In another embodiment, an exemplary embodiment of the present invention includes a holding device for studying cells comprising a substantially transparent carrier plate having a plurality of cavities surrounded by walls formed in a first surface of the carrier plate, a layer of adhesive, which is known to those skilled in the art, disposed on a bottom surface of each cavity, a layer of substantially transparent substrate material having a refractive index of 1.33 and having a multiplicity of pico liter wells formed in an upper surface thereof disposed on the adhesive layer. While MY-133 is known to have a refractive index close to that of water, heretofore MY-133 has apparently not been considered suitable for use as an inert substrate for holding live cells in a medium. In other embodiments, other adhesive materials, possibly with other refractive indexes are used for embossing.

In an exemplary embodiment of the invention, the embossing methods described herein are applied on fragile bases so little temperature and/or pressure changes are applied. Rather the embossing is optionally at low pressure and at room temperature (e.g., 15-35 degrees Celsius). In an exemplary embodiment of the invention, the embossed substrate is non-reversibly deformed by the embossing. In an exemplary embodiment of the invention, the embossed substrate is set by one or more of chemical setting, light setting, radiation based setting and/or other cross-linking or hardening or setting methods known in the art and as appropriate for the specific materials used.

In an exemplary embodiment of the invention, the thickness of the embossed layer is minimal, for example, being 15, 5%, 20%, 60%, 100%, 300%, 100% or intermediate percentages of the depth of the picowell and/or other embossed feature. Optionally or alternatively, the additional thickness below the well is 1, 10, 20, 30, 100 microns or intermediate amounts. Variations of the embossing methods described herein, which may be variously referred to as "stamping", "micro-stamping", "replicating" or "soft-lithography" may also be practiced in accordance with some embodiments of the invention.

In an exemplary embodiment of the invention, embossing can include modification of the picowells in addition to changing the geometry. For example, the template can have attached thereto patterns for the walls between the picowells, medicaments and chemicals for attachment to the picowells or walls between them, small beads for such transfer and/or electrode wires. In portions that are not for picowells, electronics, valves and/or other items may be impressed on the substrate during embossing.

In an exemplary embodiment of the invention, embossing is carried our using a rolling die (e.g., a cylinder). Optionally, the glass slides are cut after embossing. Optionally, unneeded picowells are masked by a layer with an aperture defining the active picowells.

While the above description has focused on forming picowells, other structures can be formed as well in like manner, instead of picowells and/or to support picowell operation. For example, such structures can include landmarks to assist in user orientation (e.g., patterned clusters of non-etched areas or other singularities or markings to enhance user's orientation when the array is used). Optionally, some such markings are particularly visible under a microscope (e.g., pico well address and/or a well address). In another example, micro-fluidics structures, such as reservoirs, channels, mixers, filters and flow regulators are embossed (e.g., with the embossing defining 3D structures that affect flow. Optionally or alternatively, preparation for various structures is embossed (and/or additional elements mounted on the die), f or example, pumps, electronics, conductors, sensor mountings and/or valves.

The embossing process may change in accordance with the specific material or precursor used for the substrate. For example, some materials require the application of a primer layer to strengthen the bonding to the base layer, whereas, additionally or independently, other materials require a detoxification process in order to extract biologically toxic residues such as un-cured monomers in the embossed layer.

For example, a typical precursor may be a UV-curable adhesive such as NOA-61 or NOA-81 or the low self-fluorescence NOA-63 (Norland Products Inc., Cranbury, N.J., USA, USA). Embossing is performed, for example, by applying a drop of the fluid precursor of the adhesive on glass or plastic base, and curing the fluid precursor while in contact with a die (made, for example, from a metal such as nickel, glass, PDMS or silicone rubber) having a negative geometry of the well array. The drop of adhesive disperses between the slide and the die and forms a thin layer (e.g., 10-100 micrometers thick). After the adhesive has set, the die is peeled away or otherwise removed.

Additional acts are optionally made to stabilize the structure and its adhesion to the base and/or to extract and/or remove non-polymerized residues of the adhesive which may harm cells. Such acts can include annealing at a mild temperature (~60° C.) for at least one hour. Optionally or alternatively, the bases are soaked in 90% ethanol (or other suitable solvent, depending on materials used for construction) for 5 days. This can extract toxic un-cured agents from the polymerized adhesive. Optionally or alternatively, the slides are rinsed in distilled water to wash away debris and/or residues of the extracted undesired foreign materials. Optionally or alternatively, the materials chosen and/or washing are selected to allow long term life of biological cells without toxic effects form the cell holder. Optionally, the cells reside 1 hour, 10 hours, 24 hours, 2 days, 4 days, 1 week, 1 month or more in the cell holder without such toxic effects.

Exemplary base plates for any of the embossing methods described herein include any substantially transparent glass (or plastic) surface, such as a microscope slide (e.g., 0.17 mm-1 mm thick, 2.54 cm wide, 7.62 cm long), a Petri dish (either monolithic plastic dish or a plastic dish with a thin glass or polymer sheet bottom, designed for high resolution microscopy) or the bottom of microtitter plates (either monolithic plastic plate or plate having a thin glass or polymer sheet bottom, designed for high resolution microscopy).

Embossing can take place on essentially whole bottom area, or in certain areas. The size of the embossed area is determined by the applied volume of the precursor and the actual size of the die.

In some embodiments, the Petri dish or any other pico liter wells bearing device may include a partitioning element, such as a plastic or fabric barrier, to distinguish between several areas in the same device. The partitioning element, single or plural, if made or include mesh, slits or perforated parts can also act as a flow regulator, to damp and control (by selecting proper size and pitch of the openings) fluid transfer between partitions. For example, such a barrier can block or reduce fluid flow or block or reduce cellular or particle flow (e.g., of certain sizes), for example, acting as a filter. In some embodiments, the barrier serves to reduce flow rates to levels which would not remove cells/particles from picowells. Such barriers may be attached by any method known in the art. Optionally, the barriers are attached by dipping in a UV curable adhesive as used herein. Optionally, such barriers include a base ring for mechanically aligning said barriers on said substrate.

In this and other embodiments, the coverage of the carrier by picowell and/or other embossed regions can be, for example, 1%, 5%, 10%, 20%, 50%, 70%, 90%, 100% or intermediate amounts, for example, depending on the application.

In an exemplary embodiment of the invention, multiple sizes and/or types of pico liter wells are provided on a same substrate, for example, 2, 4, 6, 10, 20 or intermediate numbers of types of pico wells may be provided.

In those cases where plate consists of an upper structure and a bonded bottom, a precursor is optionally uniformly applied to the transparent bottom prior to placing the die and irradiating. Optionally, pico liter wells are created on the whole bottom area (e.g., using a flat and uniform die). The bottom plate is then bonded to the upper structure as it is usually done in this type of plates (for example, based on utilizing NOA as a cementable adhesive). Optionally or alternatively, pico liter wells may be created only at desired locations, such as those areas which will become the bottom of wells, excluding inter-wells areas. This can be controlled, for example, by applying aliquots of precursor instead of a uniform layer.

Embossing, using MY-133 or NOA or materials may be practiced on a microscope slide, either on the whole glass or selected parts and may serve as a base plate for various single or multi cavity devices. For example, the embossed glass can be covered with adhesive spacers and covers already used in laboratory practice, such as those made by Grace Biolabs (Bend, Oreg., USA) www.gracebio.com/ Products/Imaging_Microscopy/CoverWell_Perfusion_ Chambers and enhance the practice to include pico liter wells bottoms instead of a plain glass surface. For example, these covers can form a water-tight, multiwell cell incubation or cytochemistry chamber when pressed to coverslips or microscope slides. In some embodiments, reagents can be quickly added and removed through access ports without disturbing or cross-contaminating specimens in adjacent wells, while cells remain in their picowells.

Exemplary Non-Slide Devices

Figure 9A:
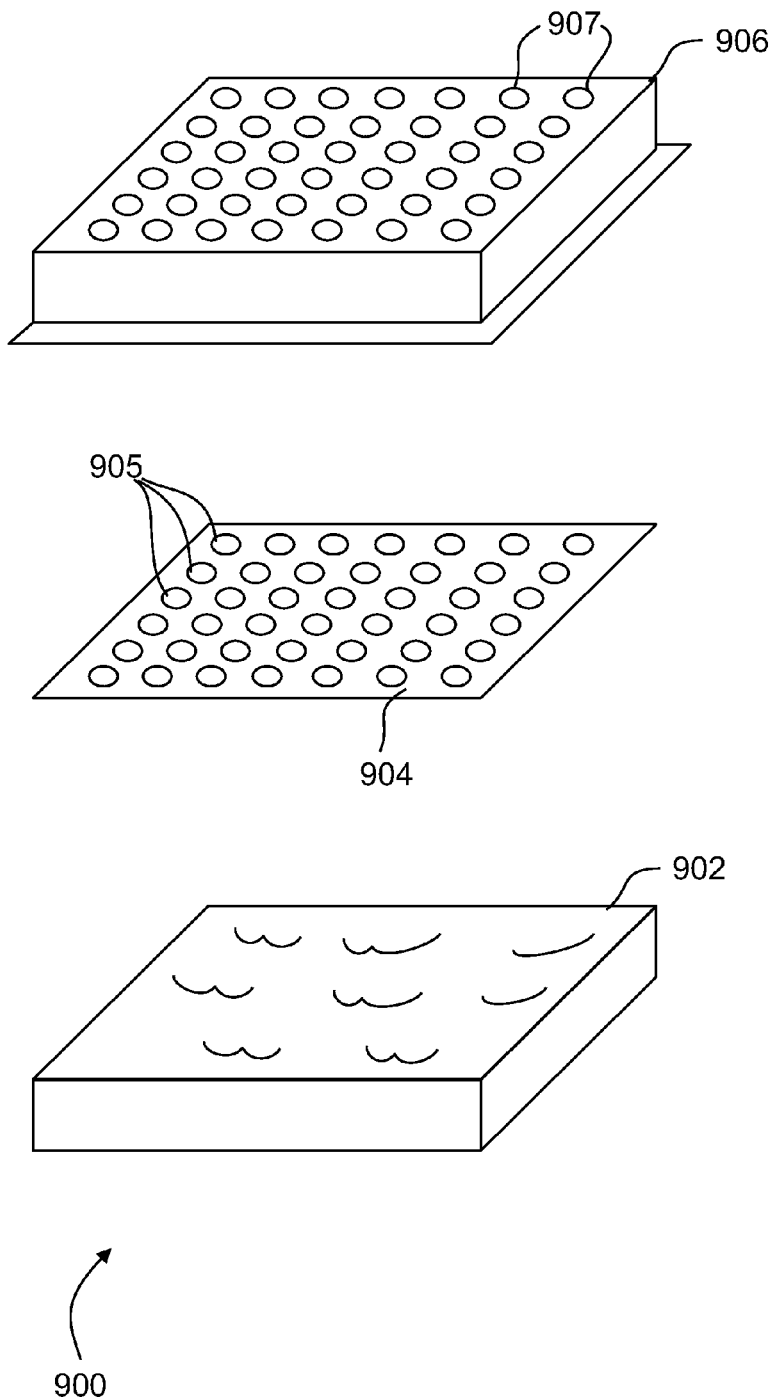
FIGS. 9A and 9B illustrate devices manufactured using double-sided tape, in accordance with exemplary embodiments of the invention.
Figure 9B:
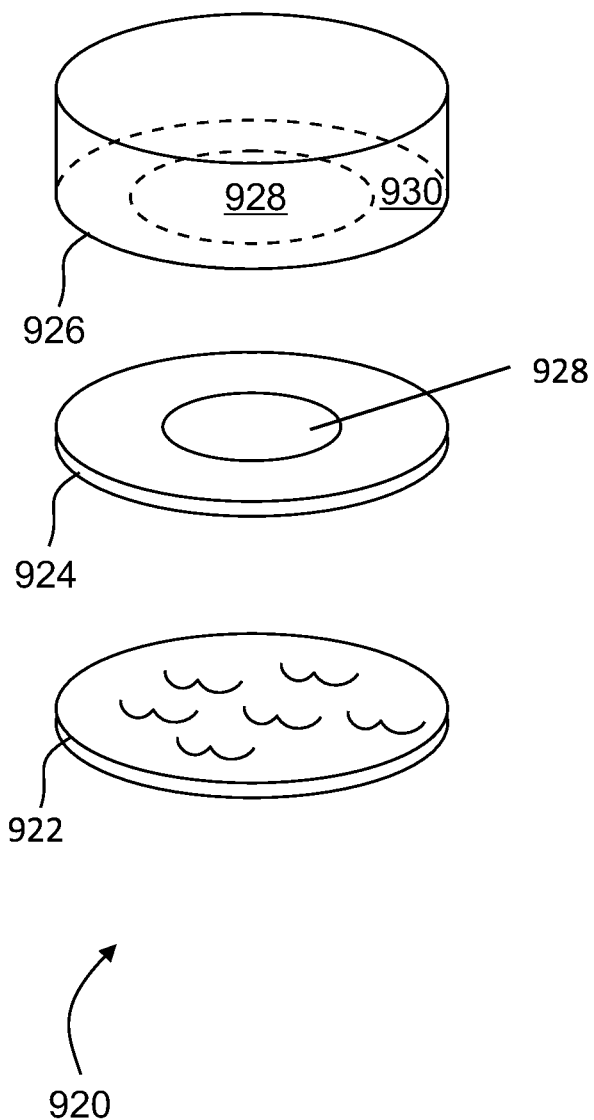

FIGS. 9A and 9B illustrate non-slide devices using masking and/or double sided table to build up walls, in accordance with exemplary embodiments of the invention. In an exemplary embodiment of the invention, such double sided tape serves to bond a wall onto a substrate and/or fill in unused picowells so fluid does not flow therein.

FIG. 9A shows a multi-well device 900, optionally of the standard size of a microtitter plate (e.g., ~127 mm×85 mm), with for example, 24, 48 or 96 wells, constructed using a base layer 902 having picowells formed over substantially its entire surface. On base 902, a double sided adhesive layer 904 is provided, with apertures 905 matching desired well areas. An upper layer 906 defines the well walls for a plurality of wells 907.

FIG. 9B shows a Petri dish 920 formed using a base layer 922 with picowells defined thereon. A double sided adhesive layer 924 is used to define active picowells and to mount a wall layer 926 above. Optionally, as shown, layer 924 includes an aperture 928 for accessing some picowells and also includes a cover portion 930 which mounts on layer 924 and also prevents cells from adhering to layer 924. Optionally, the outer diameter of adhesive layer 924 is smaller than an outer diameter of cover portion 930. If larger, excess is optionally trimmed, for example, with a knife.

Multi-Channel Slide

In an exemplary embodiment of the invention, a slide is provided with multiple picowell areas. While such areas may be provided in series (each one down flow of the other), in other embodiments, such picowell areas are provided to have parallel fluid pathways. Optionally, the design of FIG. 6 is made narrower and/or smaller and two or more such designs provided on a single slide. Optionally or alternatively, multiple such fluid pathways can share an input inlet and/or waste reservoir (but not the cell area itself or capillaries leading to and from), so two or more sets of cells can receive same treatments. Optionally or alternatively, one or more input inlets lead to two cell holding areas, while at least one input inlet is provided for only one of the cell areas, allowing both same and different treatment of multiple cell areas.

Figure 10A:
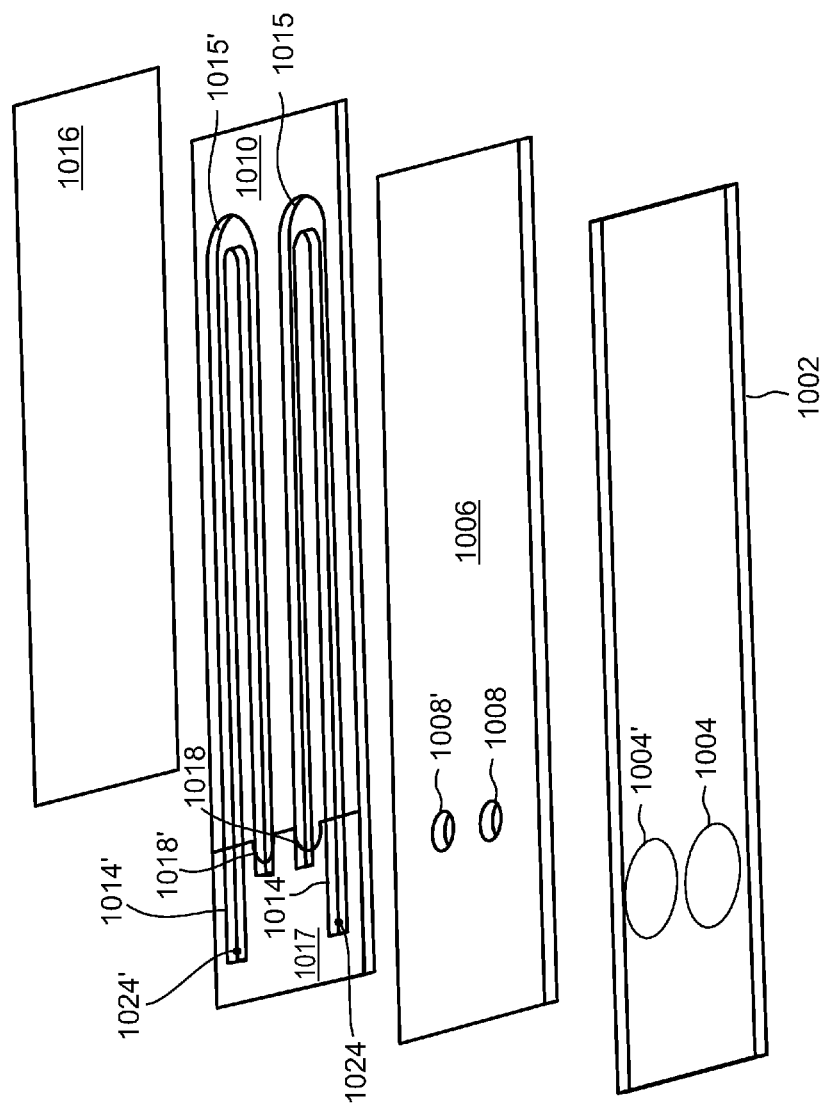
FIG. 10A illustrates a dual-array slide design, in accordance with an exemplary embodiment of the invention.

FIG. 10A shows a multi-picowell design in which the waster reservoirs (or alternatively, input reservoirs) are implemented as elongated convoluted channels, rather than as wide areas. IN a different device design, such a waste channel may be defined as a spiraling channel surrounding or extending form a pico cell area.

As shown, a base layer 1002 has two picowell areas 1004 and 1004' defined thereon, for example, by embossing, engraving and/or adhering. A masking and/or filling and/or matching layer 1006 has defined therein aperture 1008 and 1008' which define which picowells will be active. A next, conduit, layer 1010 defines two waste reservoir channels 1015 and 1015' which end at covered sections 1014 and 1014' including a fixed cover 1017 with air holes 1024 and 1024, for air release. As noted above, the size of air holes can be used to affect capillary flow rate.

A cover 1016 (for example flexible, e.g. polycarbonate, or rigid e.g. glass) may operate as cover 616 above and a pair of fluid adding ports 1018 and 1018' may be coupled to picowells by capillary or non-capillary flow.

Figure 10B:
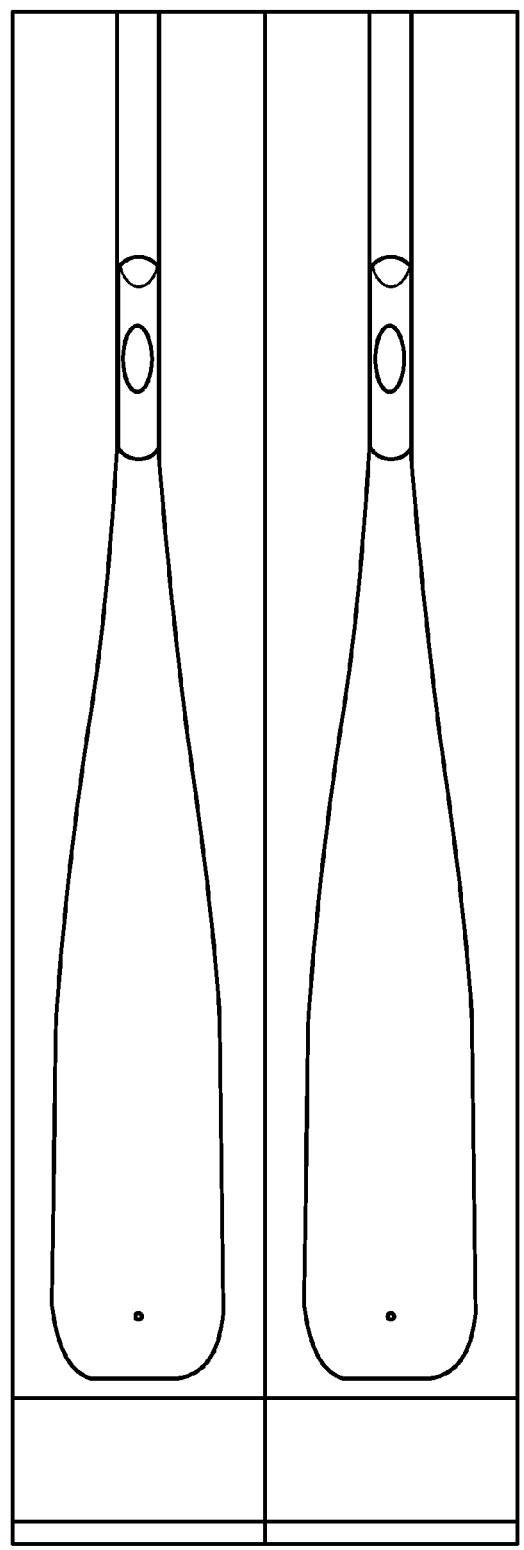
FIGS. 10B-10D illustrate additional multi-array slides, in accordance with exemplary embodiments of the invention.

FIG. 10B shows an alternative embodiment with two side by side cell holders and conduits, in which the design of FIG. 6, for example, is narrowed, so two will fit n a standard slide, side by side. In an exemplary embodiment of the invention, the reservoir is made narrower, but the capillaries are not, so as to maintain flow rates. Optionally or alternatively, multiple design changes are made, for example, narrowing capillaries while using more wettable materials in the capillaries, to maintain desired flow characteristics.

In an exemplary embodiment of the invention, different ones of the capillaries of different fluid systems on a same base have different flow rates. Optionally or alternatively, different ones of the cell holders are adapted for holding different cells and/or have different cell position disruption rates.

In an exemplary embodiment of the invention, the reservoirs and/or inlets associated with the two cell holders are shared and/or linked, allowing, for example, to provide same treatments to two sets of cells and/or provide a larger reservoir.

Figure 10C:
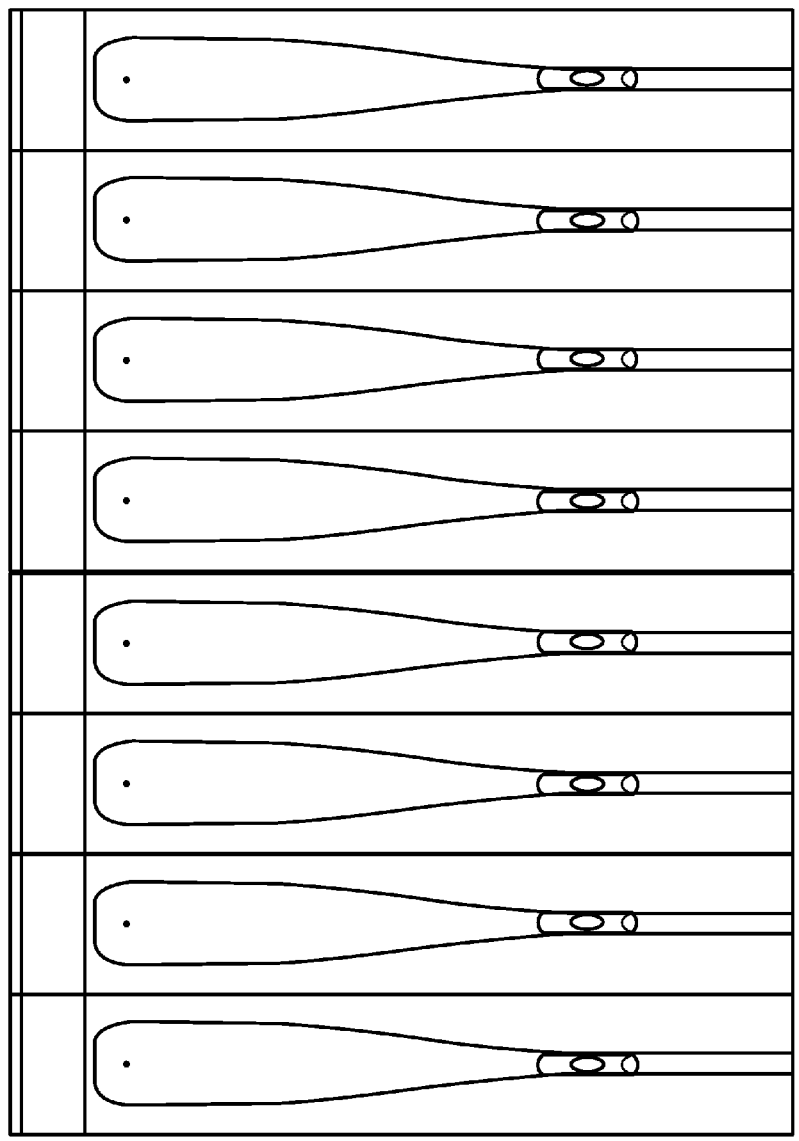

FIG. 10C shows an eight section cell holding device, with eight side by side cell holders and conduits. Optionally, the device is of a size of a standard microtitter plate. Other numbers of cells holders and conduits may be provided, for example, 16, as shown in FIG. 10D, 48, 96 or larger or intermediate numbers.

Optionally, two or more reservoirs, or all the reservoirs are linked to form a unitary waste receptacle. Optionally, this receptacle is large enough so that danger if flow back into cell holders is small. Optionally, the widening of the capillary from the cell holder to the reservoir, serves as a one way flow path, wherein flow back is less likely.

Figure 10D:
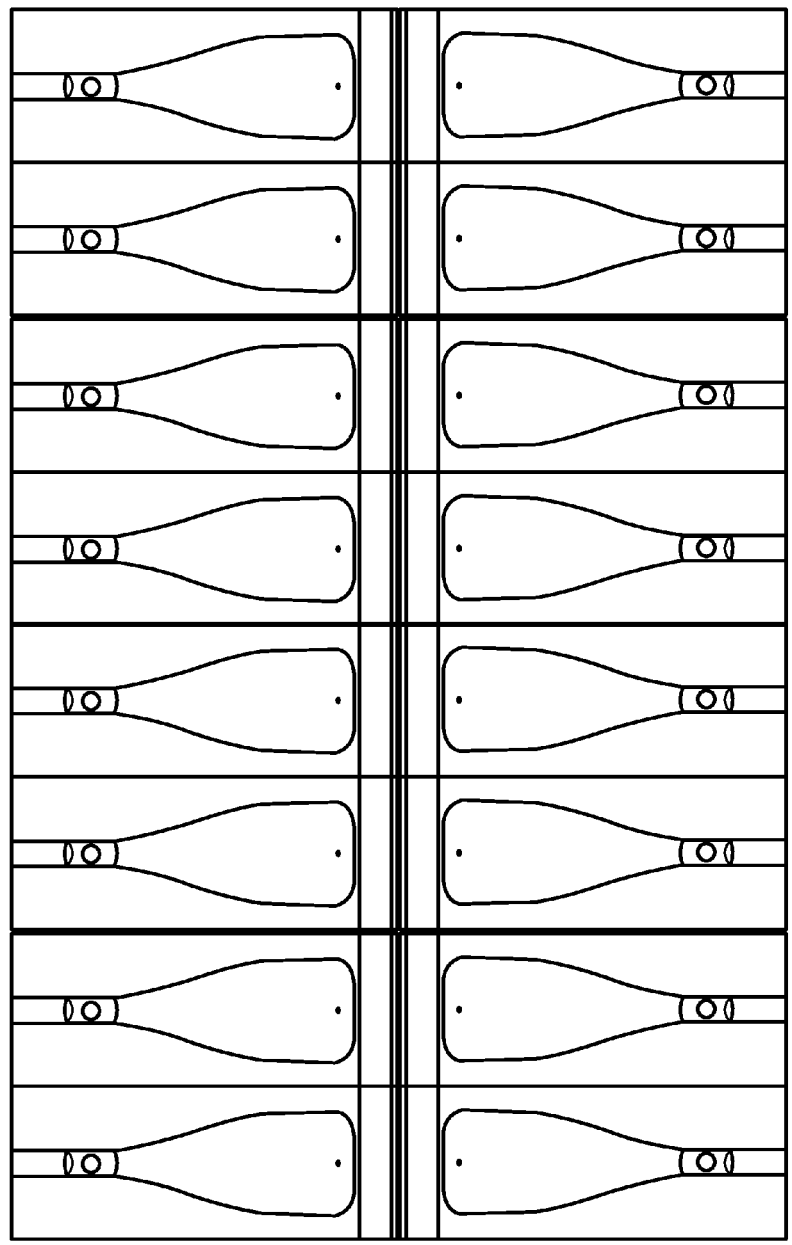

In an exemplary embodiment of the invention, the systems of FIG. 10C and FIG. 10D (and optionally of 10B) are separable into individual slide or groups of slides. Optionally, this is achieved by scoring the upper layers and/or base plate. Optionally, such devices (as in FIGS. 10A-10D) are formed by methods other than the layering methods described herein. Optionally or alternatively, the base layer is pre-cut.

In an exemplary embodiment of the invention, the inlet locations of the individual cell holders are positioned uniformly in a geometry compatible with standard multi-well cell holders. This can allow automatic fluid providing to such cell holders. Optionally, initial loading is manual. Optionally, the cover layer is separated for each cell holder, so that each cell holder can be uncovered, filled and covered (e.g., adhered in place) separately. Optionally, separate nonstick layers sections are provided for each cell holder. In an alternative embodiment, cell filling is into an inlet, and is also performed automatically. This may be facilitated by a design such as that of device 10.

Potential Advantages and/or Features

Potential advantages and/or features of device 10 and 600 and other embodiments described herein, which may be utilized in accordance with exemplary embodiments of the invention, include one or more of the following. It is noted that some of the advantages and/or features can be provide din other device designs in accordance with exemplary embodiments of the invention, for example the shapes and flow control can be achieved in devices not formed of layers as in FIG. 6. In addition, not all features and/or advantages are provided in every device in accordance with exemplary embodiments of the invention.

(a) Devices that are relatively simple to manufacture and assemble at low cost and in high volumes, for example, by providing simple parts optionally cut from sheets to assemble with optionally reduced need for alignment and/or processing of details on a part or assembled parts.

(b) Devices which support high-resolution imaging by both upright and inverted microscopes.

(c) Devices over a range of desirable flow rates, cell sizes, array size and/or other properties, which are optionally made from modules, which are interchangeable and/or which are for this reason and/or others amenable for construction on a single assembly line.

(d) Devices which are formed only of thin planar layers, optionally with limited breakability, with capillary channels defined by cutting out of layers, rather than cutting away into layers. Optionally, the thickness of the channel is controlled by varying the number of sub layers that laminate to form a conduit layer.

(e) Devices which do not require assembly of discrete parts by a user, but which are optionally substantially protected from air and/or fluids except at very limited portion thereof. Optionally, the devices allow additional manipulation prior to sealing of such a device by a user.

(f) Devices which mount walls on a microfluidics device using double sided tape.

(g) Using a layer of double sided tape to mask out a larger cell holding array, for example a pico well array, to define a part of the array to be active.

(h) Controlling capillary flow by a combination of one or more of capillary cross-sectional shape and/or size, capillary materials, air release, baffles and/or surface treatments.

(i) Ability to select a design which has desired flow and/or cell dislodging characteristics, for a particular need and/or experimental setup.

(j) Devices with capillary channels including reservoirs which are sealed on all sides except for an inlet and air release or absorbing media.

(k) Preventing contamination and/or reusability by adhering a cover on top of a device, while optionally distancing a cell holding area from an inlet port so such area is reachable only by capillary flows and cannot be washed out. Adhesive can be, for example, permanent or multi-use (enabling repeated opening and closing).

(l) Setting a cover on a device using an adhesive attachment between the cover and the conduits, so that the cover defines the conduits, initiates and/or supports capillary action and is optionally unbreakable (unlike thin glass covers).

(m) Provide sets of devices (e.g., 2, 3, 4, 5, 10, 15, 20, or more or intermediate numbers or an array of different devices connected together) as a kit for a range of experimental settings (e.g., desired flow rate) conditions, cells and/or reagents and/or provide devices packaged with instructions or at least an indication of expected performance under different conditions.

(n) Provide devices with flow regulation at both inlet and outlet from cell holding area.

(o) Allow overflow to leave device without compromising the cell holding area.

(p) Provide devices which have unique identification mark or product code—barcode or RFID—to enable automatic upload of device characteristics.

(q) By including an opening to the atmosphere near the cell holder, diffusion of gasses in and out of the cells are supported. Optionally, such diffusion is reduced or prevented by taping or otherwise placing a cover over the inlet. Optionally, the distance between the inlet port and the cell holders is selected to have a desired gas diffusion rate.

In an exemplary embodiment of the invention, sides are marked with a marking or instructions which indicate various properties thereof, for example, flow rate under one or more conditions, cell/well size, cell disruptability, size and/or picowell arrangement and/or diversity.

In an exemplary embodiment of the invention, there is provided an experimental design software which includes a table indicating various characteristics of such devices and which can be used to select devices that have desired flow, etc. characteristics for certain experiments. Such software can be provided, for example, on computer readable media such as a CD, diskette, hard-disk, ROM and/or RAM. Optionally, the markings include a computer readable marking such as a barcode or RFID.

In an exemplary embodiment of the invention, software (e.g., local or at a network location/server) is used by a user to order particular device designs and such devices are assembled according to the request, from modular components.

Optionally, the parts of the device are sold separately, optionally in sets of various properties and a user or manufacturer can assemble such devices, as needed.

While the description has focused on manual manipulation, a plurality of slides can be managed by computerized/robotic means. Optionally, the use of a capillary to control flow rates, simplifies handling of such slides and allows nutrients, etc. to be provided as a drop at an inlet port, which drop will then be "pumped" at a desired rate. This allows rapid treatment of multiple wells and cell holding areas without individually controlling the flow at each of a plurality of cell arrays using individual pumps or in serial manner.

General

The terms "comprises", "comprising", "includes", "including", "having" and their conjugates mean "including but not limited to".

The term "consisting of means "including and limited to".

The measurements described herein for, inter alia, sizes, volumes and/or rates, while exemplary, may be modified depending on the application, and are intended to include, for example, measurements that are for example, 10%, 20%, 30%, 50%, 70%, 90% larger or smaller, or 100%, 200%, 300% larger, or intermediate percentages of the above percentages.

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In case of conflict, the patent specification, including definitions, will control.

In addition, citation or identification of any reference in this application shall not be construed as an admission that such reference is available as prior art to the present invention. To the extent that section headings are used, they should not be construed as necessarily limiting.

The invention claimed is:

1. A cell study device, comprising:
a base layer wherein said base layer comprises a socket;
a planar conduit defining layer, separate from said base layer, including an aperture forming side walls of a channel therein;
a planar cover layer, separate from said base and conduit defining layer, which, together with the side walls of said channel and said base layer, forms an enclosed capillary flow channel in said conduit layer in parallel to said base layer and above said base layer, wherein the cross-section of said capillary flow channel is generally perpendicular to said base layer and is sized such that capillary fluid flow results from the attachment of said cover layer to said conduit layer,
wherein fluid flow in said capillary flow channel is capillary fluid flow resulting solely from capillary forces within said capillary flow channel;
and
a cell holding area positioned within said socket comprising an array of cell-holding picowells on said base layer in fluid contact with said capillary flow channel, said picowells being sized and configured to accommodate and immobilize a single cell or a predetermined number of cells for exposure to a sequence of liquid aliquots delivered by the capillary flow channel, thereby permitting study of cells individually, wherein said capillary fluid flow in said capillary flow channel is horizontal and above said picowells and wherein said cover layer is movable to permit access to said cell holding area.

2. A device according to claim 1, wherein said cell-holding area is formed in said base layer.

3. A device according to claim 2, wherein said cell holding area includes at least one orientation mark useful for identification under microscopy.

4. A device according to claim 2, wherein a part of said cell holding area is masked by a masking layer underlying said conduit layer.

5. A device according to claim 1, wherein said cell holding area includes a plurality of cell-holding well arrays in fluid communication with said capillary flow channel.

6. A device according to claim 1, wherein said cover layer includes one or more air holes in communication with said cell holding area for air release.

7. A device according to claim 1, wherein said capillary flow channel terminates at a distal end thereof in a substantially sealed waste reservoir with no fluid exit.

8. A device according to claim 1, wherein said capillary flow channel terminates at a distal end thereof in a substantially sealed waste reservoir with an absorbent material as a fluid exit.

9. A device according to claim 1, wherein said cover layer includes a fluid inlet area for said capillary flow channel.

10. A device according to claim 1, packaged in vacuum.

11. A device according to claim 1, wherein said conduit layer is permanently adhered to said cover layer.

12. A device according to claim 1, wherein said device is provided with a removable non-stick layer between said cover layer and said conduit layer, removal of said non-stick layer permits capillary flow in the channel between said cover layer and the conduit layer.

13. A device according to claim 1, wherein said conduit layer is temporarily adhered to said cover layer.

14. A device according to claim 1, wherein said conduit layer includes an adhesive on both its faces.

15. A device according to claim 1, wherein said layers are selected of dissimilar materials with dissimilar contact angles with fluids.

16. A device according to claim 1, wherein said device has the form factor of a standard microscope slide.

17. A device according to claim 1, wherein said device has the form factor of a standard microtiter plate.

18. A device according to claim 1, wherein said layers are formed of materials that do not interfere with cell behavior for at least 24 hours when loaded with an aqueous solution.

19. A device according to claim 1, further comprising indications of one or both of a capillary flow rate and a cell dislocation rate therein.

20. A device according to claim 19, comprising a plurality of different cell study devices, each with different sets of flow rate and dislocation rate.

21. A device according to claim 19, wherein said indication is per one or both of fluid property and cell type.

22. A device according to claim 19, wherein said indication is machine-readable.

23. A device according to claim 19, wherein said indication is human readable.

24. A device according to claim 19, including instructions explaining said indications.

25. A device according to claim 19, including software on a computer readable medium for using said indications.

26. A device according to claim 1, further including a removable non-adhesive layer that interferes with adhesion of at least two parts of said device, said interfering inactivating said capillary flow channel.

27. A device according to claim 26, wherein said adhesion is permanent, when said non-adhesive interfering layer is removed.

28. A cell study device according to claim 1 comprising: a double-sided adhesive layer masking some of the picowells in said cell holding area, wherein said conduit defining layer is mounted on said double-sided adhesive layer.

29. A cell study device according to claim 28, including a plurality of cell holding areas that are in fluidic isolation from each other.

30. A cell study device according to claim 29 wherein each cell holding area includes a capillary flow channel separate from capillary flow channels associated with the other cell holding areas.

31. A cell study device according to claim 28 wherein said adhesive layer is apertured.

32. A cell study device according to claim 28, wherein said walls are at least 2 mm high.

33. A device according to claim 1, wherein said cover layer is transparent.

34. A cell study device according to claim 1, wherein said cover layer is flexible.

35. A cell study device according to claim 1, wherein said cover layer is partially adherent to said conduit layer.

36. A device according to claim 1, wherein said cell-holding array is defined by a plurality of closely packed pits in a surface of said base layer.

37. A device according to claim 1, wherein said channel walls are at least 2 mm high.

38. A device according to claim 1, wherein said cell-holding well array is comprised of picowells having a diameter of about 1 micrometer or about 500 micrometers.

39. A device according to claim 1, wherein said base layer is comprised in a structure having the form of a Petri dish.

40. A device according to claim 1, wherein the array of cell-holding picowells is located in a recess in said base layer.

41. A cell study device according to claim 1, wherein the picowells comprise non-adhesive picowells configured to prevent adherence of cells and the cell-holding area geometry is configured to control cell dislocation rate.

42. A cell study device according to claim 1, further including a flow regulator to prevent cells from being displaced from the picowells due to fluid flow.

43. A device according to claim 1, wherein said picowells are formed of hydrogel.

44. A cell study device comprising:
a unitary structure including
a base layer, wherein said base layer comprises a socket;
the base layer including a cell holding area positioned within said socket, wherein said cell holding area comprising an array of picowells in which the picowells are sized and configured to accommodate and immobilize a single cell or a predetermined number of cells;
a second layer permanently adhered to the base layer including an aperture that defines a barrier on the base layer and provides fluid access to the picowell array; and
a further layer forming an upwardly extending wall permanently attached to the second layer surrounding the picowell array;
the device further including a cover that is separate from or part of the unitary structure, which together with said unitary structure forms an enclosed capillary flow channel in parallel to said base layer, wherein the cross-section of said capillary flow channel is generally perpendicular to said base layer and is sized such that capillary fluid flow in said capillary flow channel is-in parallel to said base layer, and above and in parallel to said picowells results from the attachment of said cover layer to said unitary structure,
and wherein said cover is moveable to allow access to said picowell array.

45. A cell study device according to claim 44, wherein the base layer includes a structure that surrounds the cell holding area.

46. A cell study device according to claim 45 in which the structure forms a recess in the base layer in which the picowell array is located.

47. A cell study device according to claim 44, in which the cell holding area is comprised of picowells having a diameter of about 1 micrometer or of about 500 micrometers.

48. A cell study device according to claim 44, in which the unitary structure is in the form of a Petri dish.

49. A cell study device according to claim 44, in which the cover and the base layer are transparent.

50. A cell study device according to claim 44, in which the array of picowells is embossed on the base layer.

51. A cell study device according to claim 44, in which the cell holding area includes at least one orientation mark useful for identification under microscopy.

52. A cell study device according to claim 44, including at least one partitioning element providing fluidic isolation between areas of picowells on the base layer.

53. A cell study device according to claim 44, in which the picowell array is defined by a plurality of closely packed pits etched in a surface of the base layer.

54. A cell study device according to claim 44, in which the cell holding area is coated with a chemical or biological material.

55. A cell study device according to claim 44, in which the base layer is glass.

56. A cell study device according to claim 55, in which the second layer, the wall surrounding the second layer, and the cover are formed of a plastic material.

57. A cell study device according to claim 44, in which the cover is moveable and is configured to fit on the top of the upwardly extending wall.

58. A cell study device according to claim 44, in which the picowell array is comprised in a component attached to the base layer as part of the unitary structure.

59. A cell study device according to claim 44, wherein the picowells comprise non-adhesive picowells configured to prevent adherence of cells and the cell holding area geometry is configured to control cell dislocation rate.

60. A cell study device according to claim 44, further including a flow regulator to prevent cells from being displaced from the picowells due to fluid flow.

61. A cell study device according to claim 44, wherein said picowells are formed of hydrogel.

* * * * *